(12) United States Patent
Walker et al.

(10) Patent No.: US 7,135,467 B2
(45) Date of Patent: Nov. 14, 2006

(54) HIV INTEGRASE INHIBITORS

(75) Inventors: Michael A. Walker, Durham, CT (US); Hatice Belgin Gulgeze, Middletown, CT (US); Narasimhulu B. Naidu, Durham, CT (US); Margaret E. Sorenson, Meriden, CT (US); Yasutsugu Ueda, Clinton, CT (US); John Matiskella, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 360 days.

(21) Appl. No.: 10/755,642

(22) Filed: Jan. 12, 2004

(65) Prior Publication Data

US 2004/0204498 A1    Oct. 14, 2004

Related U.S. Application Data

(60) Provisional application No. 60/439,594, filed on Jan. 13, 2003.

(51) Int. Cl.
*C07D 417/04* (2006.01)
*C07D 401/04* (2006.01)
*A61K 31/506* (2006.01)
*C07D 239/60* (2006.01)

(52) U.S. Cl. .................. 514/222.2; 514/235.8; 514/252.14; 514/269; 514/272; 544/3; 544/122; 544/295; 544/311; 544/319; 544/320

(58) Field of Classification Search ............ 544/3, 544/122, 295, 311, 319, 320; 514/222.2, 514/269, 235.8, 272, 252.14
See application file for complete search history.

(56) References Cited

U.S. PATENT DOCUMENTS

| 6,096,753 | A | 8/2000 | Spohr et al. |
|---|---|---|---|
| 2005/0025774 | A1 | 2/2005 | Crescenzi et al. |
| 2005/0075356 | A1 | 4/2005 | Di Francesco et al. |
| 2005/0261322 | A1* | 11/2005 | Naidu et al. ............ 514/269 |
| 2006/0046985 | A1 | 3/2006 | Crescenzi et al. |

FOREIGN PATENT DOCUMENTS

| EP | 1422218 A1 | 5/2004 |
|---|---|---|
| WO | WO 02/06246 A1 | 1/2002 |
| WO | WO 03/035077 * | 5/2003 |
| WO | WO 2003/062211 A1 | 7/2003 |
| WO | WO 2005/061490 A1 | 7/2005 |
| WO | WO 2005/061501 A2 | 7/2005 |
| WO | WO 2005/070901 A2 | 8/2005 |

OTHER PUBLICATIONS

Miles et al., Medline Abstract (The growing of HIV pandemic, Community Pract vol. 78, Issue 8, pp. 292-294) Aug. 2005.*
Johnson et al., CAPLUS Abstract 23:16245, 1929.*
Marcus et al., PubMed Abstract (Intervirology, 45(4-6):260-6), 2002.*
van Heeswijk et al., PubMed Abstract (Antivir Ther 6(4):201-29) Dec. 2001.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, Aug. 2002.*
Silverman, Prodrugs and Drug Delivery Systems, The Organic Chemistry of Drug Design and Drug Action, pp. 352-400, 1992.*
Bundgaard, Design of Produgs: Bioreversible derivatives for various functional groups and chemical entities, pp. 1, 1995.*
Sunderland et al. (2001) Inorganic Chemistry, vol. 40, pp. 6746-6756.
Neamati et al. (1997) Drug Discovery Today, vol. 2, No. 11, pp. 487-498.
T. P. Culbertson, "Synthesis of 5,6-Dihydroxy-2-Phenyl-4-Pyrimidinecarboxylic Acid, Methyl Ester, a Corrected Structure," J. Heterocyclic Chem. 16, pp. 1423-1424, 1979.
S. D. Dreher, et al, "Highly Selective Synthesis of 2-Substituted-5-Hydroxy-6-Oxo-1,6-Dihydropyrimidine-4-Carboxylic Acid Derivatives Using a Novel Protected Dihydroxyfumarate," Tetrahedron Letters, 45, pp. 6023-6025, 2004.

* cited by examiner

*Primary Examiner*—Deepak Rao
(74) *Attorney, Agent, or Firm*—James Epperson; Warren K. Volles

(57) ABSTRACT

Compounds useful for treating HIV are disclosed having the general formula

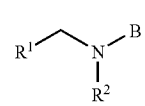

I wherein $R^1$, $R^2$, and B are as defined in the specification. Compositions containing the compounds and methods for using the compounds to inhibit HIV are also disclosed.

29 Claims, No Drawings

HIV INTEGRASE INHIBITORS

CROSS REFERENCE TO RELATED APPLICATION

The non-provisional application claims priority from the provisional application U.S. Ser. No. 60/439,594 filed Jan. 13, 2003.

FIELD OF THE INVENTION

The present invention is generally directed to antiviral compounds, and more specifically directed to compounds which can inhibit the functioning of the human immunodeficiency virus-1 (HIV-1), compositions comprising such compounds and methods for inhibiting the functioning of the HIV-1.

BACKGROUND OF THE INVENTION

HIV-1 infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include, for example, the following nucleoside reverse transcriptase (RT) inhibitors: Retrovir™ zidovudine (or AZT), Videx™ didanosine, Zerit™ stavudine, Epivir™ lamivudine (or 3TC), Hivid™ zalcitabine (or DDC), Ziagen™ abacavir succinate, Viread™ Tenofovir disoproxil fumarate salt, Combivir™ (-3TC plus AZT), Trizivir™ (abacavir, lamivudine, and zidovudine); the following non-nucleoside reverse transcriptase inhibitors: Viramune™ nevirapine, Rescriptor™ delavirdine and Sustiva™ efavirenz, and the following peptidomimetic protease inhibitors: saquinavir, indinavir, ritonavir, nelfinavir, amprenavir, lopinavir, Kaletra™ (lopinavir and rtonavir), and Reyataz™ atazanavir sulfate. Often, these drugs can only transiently restrain viral replication if used alone. However, when used in combination, these drugs can have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options whether used alone or in combination with other drugs.

HIV expresses three enzymes, reverse transcriptase, an aspartyl protease and integrase, all of which are potential antiviral targets for the development of drugs for the treatment of AIDS. However, integrase stands out as being the only viral enzyme not targeted by currently approved therapy. The integrase enzyme is responsible for insertion of the viral cDNA into the host cell genome, which is a critical step in the viral life cycle. There are a number of discrete steps involved in this process including processing of the viral cDNA by removal of two bases from each 3'-terminus and joining of the recessed ends to the host DNA. Studies have shown that in the absence of a functional integrase enzyme HIV is not infectious. Therefore, an inhibitor of integrase would be useful as a therapy for AIDS and HIV infection.

A number of HIV integrase inhibitors have been reported. These include nucleotide-based inhibitors, known DNA binders, catechols and hydrazide containing derivatives (Neamati, N.; Sunder, S.; Pommier, Y., *Drug Disc. Today*, 1997, 2, 487).

Certain pyrimidines and pyrimidinones have been disclosed. WO 02/06246 discloses 2-aryl-4,5-dihydroxy-6-carboxypyrimidines as viral polymerase inhibitors which are proposed for use in treating hepatitis C virus infection. Sunderland, C. J; Botta, M.; Aime, S.; and Raymond, K. N. Inorg. Chem. (2001) 40, 6746–6756 discloses the synthesis of 6-carboxamido-5,4-hydroxypyrimidinones as gadolinium chelating agents.

SUMMARY OF INVENTION

The present invention relates to compounds having the formula

wherein:
$R^1$ is —$C_1$–$C_6$ alkyl, $C_3$–$C_6$ cycloalkyl, -aryl, —$C_1$–$C_6$ alkyl-aryl, or —$C_1$–$C_6$ alkyl-diaryl;
$R^2$ is —H, —OH, —$C_1$–$C_6$ alkyl unsubstituted or substituted with 1–3 $R^3$, or —$OR^4$;
Each $R^3$ is independently selected from the group consisting of —H, -halo, —CN, —$C_1$–$C_2$ perfluoroalkyl, —$C_1$–$C_6$ alkyl, —$C_1$–$C_2$ perfluoroalkoxy, and —$C_1$–$C_6$ alkoxy;
$R^4$ is —$C_1$–$C_6$ alkyl or —$C_3$–$C_6$ cycloalkyl;
B is selected from the group consisting of

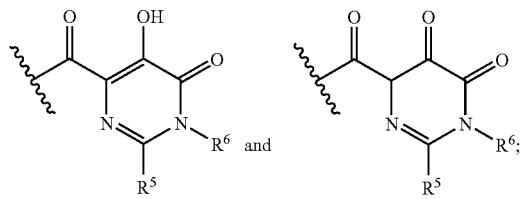

$R^5$ is —$NR^7R^8$; or Het wherein the bond attaching $R^5$ is made to a heteroatom in said Het;
$R^6$ is —H, —$C_1$–$C_6$ alkyl unsubstituted or substituted with 1–3 $R^3$; and
$R^7$ and $R^8$ are independently —H or —$C_1$–$C_6$ alkyl;
or pharmaceutically acceptable enantiomer, diastereomer, salt, solvate or prodrug thereof.

The present invention also includes pharmaceutical compositions comprising the compounds or pharmaceutically acceptable enantiomer, diastereomers, salts, solvates or prodrugs thereof and a pharmaceutically acceptable carrier. The compositions can be useful for inhibiting HIV integrase or for treating patients infected with the HIV virus or suffering from AIDS or ARC (AIDS related complex), which comprises a therapeutically effective amount of one or more compounds of Formula I, including pharmaceutical acceptable enantiomer, diastereomers, salts, solvates or prodrugs thereof, and a pharmaceutically acceptable carrier.

The present invention also provides methods of inhibiting HIV integrase by administering to a patient an effective amount of a compound of Formula I, or a pharmaceutically acceptable enantiomer, diastereomers, salt, solvate or prodrug thereof. The present invention further provides methods of treating patients infected by the HIV virus, or of treating AIDS or ARC, by administering to the patient an effective amount of a compound of Formula I, or a pharmaceutically acceptable enantiomer, diastereomers, salt, solvate or prodrug thereof.

By virtue of the present invention, it is now possible to provide improved drugs comprising the compounds of the invention which can be effective in the treatment of patients infected with HIV. Specifically, the present invention provides compounds that can inhibit the functioning of HIV integrase. Further, the present invention makes it possible to administer combination therapy to a patient whereby a compound in accordance with the present invention, which is effective to inhibit the HIV integrase, can be administered with another compound having anti-HIV activity, e.g., a compound which is effective to inhibit the function of a target selected from the group consisting of HIV protease, a nucleoside reverse transcription, a non-nucleoside reverse transcriptase or HIV entry.

DETAILED DESCRIPTION OF THE INVENTION

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture. With reference to the instances where (R) or (S) is used, it is to designate the absolute configuration of a substituent in context to the whole compound and not in context to the substituent alone.

Unless otherwise specifically noted herein, the terms set forth below will have the following definitions.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445. The compounds of the present invention are useful in the form of the free base or acid or in the form of a pharmaceutically acceptable salt thereof. All forms are within the scope of the invention.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of formula I, and pharmaceutically acceptable enantiomers, diastereomers, salts, and solvates, e.g. hydrates, and prodrugs. Similarly, references to intermediates, are meant to embrace their salts, and solvates, where the context so permits. References to the compound of the invention also include the preferred compounds, e.g. formula II and formula III.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The term "substituted" as used herein includes substitution at from one to the maximum number of possible binding sites on the core, e.p., organic radical, to which the subsitutent is bonded, e.g., mono-, di-, tri- or tetra-substituted, unless otherwise specifically stated.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine or arylalkyl, include all possible stable configurations, unless otherwise specifically stated. Certain radicals and combinations are defined below for purposes of illustration.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents having the specified number of carbon atoms and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specfically stated. This a $C_{4-10}$ alkylcycloalkyl may contain from 1–7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralalkyl" mean an aryl group substituted with one or more alkyl groups. Unless the carbon range of each group is specified, the stated range applies to the entire substituent. Thus, a $C_{7-14}$ alkylaryl group many have from 1–8 carbon atoms in the alkyl group for a monocyclic aromatic and from 1–4 carbon atoms in the alkyl group for a fused aromatic. Similarly, a $C_{1-6}$ alkyl-aryl group would contain a six membered aryl group and a 1–6 carbon alkyl segment. A $C_{1-6}$ alkyl-diaryl group would contain a ten membered aryl group and a 1–6 carbon alkyl segment. The attachment of the group to bonding site on the molecule can be either at the aryl group or the alkyl group. Unless a specific aryl radical is specified, e.g., fluoro-phenyl, or the radical is stated to be unsubstituted, the aryl radicals include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl(alkoxy)amine. Examples of alkylaryl groups include benzyl, butylphenyl and 1-naphthylmethyl.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "alkylamide" as used herein means an amide mono-substituted with an alkyl, such as

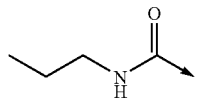

The term "heterocycle", also referred to as "Het", as used herein means 7–12 membered bicyclic heterocycles and 5–9 membered monocyclic heterocycles.

Preferred bicyclic heterocycles are 7–12 membered fused bicyclic ring systems (both rings share an adjacent pair of atoms) containing from one to four heteroatoms selected from nitrogen, oxygen and sulfur, wherein one or both rings of the heterocycle can be saturated, partially saturated or fully unsaturated ring system (this latter subset also herein referred to as unsaturated heteroaromatic or heteroaryl). The nitrogen and sulfur heteroatoms atoms may be optionally oxidized. The bicyclic heterocycle may contain the heteroatoms in one or both rings. Unless a specific heterocycle is specified, e.g., a fluorinated 7–12 membered bicyclic heterocycle, or the heterocycle is stated to be unsubstituted, the heterocycles include those substituted with typical substituents known to those skilled in the art. For example, the bicyclic heterocycle may also contain substituents on any of the ring carbon atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di- halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfonamide, $C_{1-6}$ alkylsulfoxide, di ($C_{1-6}$) alkyl(alkoxy)amine, $C_{6-10}$ aryl, $C_{7-14}$ alkylaryl, and a 5–7 membered monocyclic heterocycle. When two substituents are attached to vicinal carbon atoms of the bicyclic heterocycle, they can join to form a ring, e.g., a five, six or seven membered ring system containing up to two heteroatoms selecting from oxygen and nitrogen.

Examples of bicyclic heterocycles include, but are not limited to, the following ring systems:

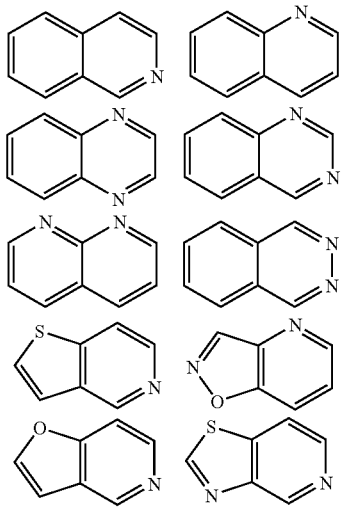

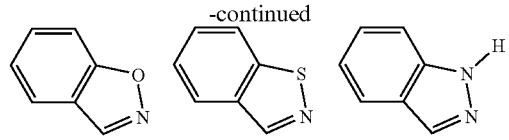

Preferred monocyclic heterocycles are 5–9 membered saturated, partially saturated or fully unsaturated ring system (this latter subset also herein referred to as unsaturated heteroaromatic) containing in the ring from one to four heteroatoms selected from nitrogen, oxygen and sulfur, wherein the sulfur and nitrogen heteroatoms may be optionally oxidized. Unless a specific heterocycle is specified, e.g., a $C_{1-6}$ alkoxy substituted 5–7 membered monocyclic heterocycle, or the heterocycle is stated to be unsubstituted, the heterocycles include those substituted with typical substituents known to those skilled in the art. For example, the monocyclic heterocycle may also contain substituents on any of the ring atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di- halo-$C_{1-6}$ alkoxy, cyano, halo, thioalkyl, hydroxy, alkanoyl, $NO_2$, SH, amino, $C_{1-6}$ alkylamino, di ($C_{1-6}$) alkylamino, di ($C_{1-6}$) alkylamide, carboxyl, ($C_{1-6}$) carboxyester, $C_{1-6}$ alkylsulfone, $C_{1-6}$ alkylsulfoxide, $C_{1-6}$ alkylsulfonamide, di ($C_{1-6}$) alkyl(alkoxy)amine, $C_{6-10}$aryl, $C_{7-14}$ alkylaryl and an additional 5–7 membered monocyclic heterocycle. Suitable heterocycles include, for example, piperidinyl, piperazinyl, pyrrolidinyl, thiazinyl and morpholinyl. Examples of heteroaryl include 2-furyl, 3-furyl, 2-pyridyl, 3-pyridyl, 4-pyridyl, pyrazinyl, 2-thienyl, 3-thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, 1,3,5-triazinyl and 1,3,5-trithianyl.

Further examples of monocyclic heterocycles include, but are not limited to, the following (and their tautomers):

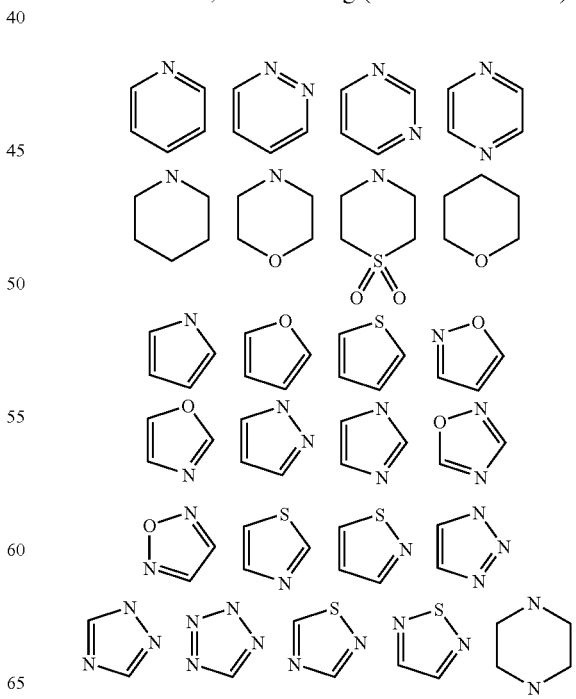

Those skilled in the art will recognize that the heterocycles used in the compounds of the present invention should be stable. Generally, stable compounds are those which can be synthesized, isolated and formulated using techniques known to those skilled in the art without degradation of the compound.

The present invention provides compounds having the following formula:

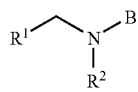
(I)

wherein:
R¹ is —C₁–C₆ alkyl, C₃–C₆ cycloalkyl, -aryl, —C₁–C₆ alkyl-aryl, or —C₁–C₆ alkyl-diaryl;
R² is —H, —OH, —C₁–C₆ alkyl unsubstituted or substituted with 1–3 R³, or —OR⁴;
Each R³ is independently selected from the group consisting of —H, -halo, —CN, —C₁–C₂ perfluoroalkyl, —C₁–C₆ alkyl, —C₁–C₂ perfluoroalkoxy, and —C₁–C₆ alkoxy;
R⁴ is —C₁–C₆ alkyl or —C₃–C₆ cycloalkyl;
B is selected from the group consisting of

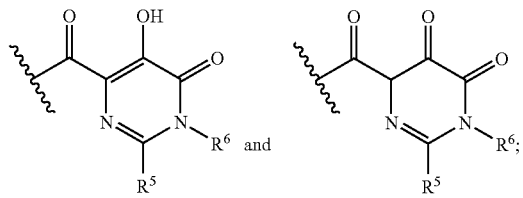

R⁵ is —NR⁷R⁸; or Het wherein the bond attaching R⁵ is made to a heteroatom in said Het;
R⁶ is —H, —C₁–C₆ alkyl unsubstituted or substituted with 1–3 R³; and
R⁷ and R⁸ are independently —H or —C₁–C₆ alkyl;
or pharmaceutically acceptable enantiomer, diastereomer, salt, solvate or prodrug thereof.

Preferably, the aryl is substituted with 1–3 R³. Preferably, R¹ is -aryl, —C₁–C₆ alkyl-aryl, or —C₁–C₆ alkyl diaryl. More preferably, R¹ is -aryl, —C₁–C₆ alkyl-phenyl, or —C₁–C₆ alkyl-diphenyl. Even more preferably, the aryl is selected from the group consisting of phenyl, naphthyl, furanyl, thienyl, indolyl, and benzimidazolyl, and aryl and phenyl are unsubstituted or substituted with 1–3 R³. Still more preferably, R¹ is aryl selected from the group consisting of naphthyl, 2-methyl-5-furanyl, 2-thienyl, 3-indolyl, and 2-benzimidazolyl. In a further preferred aspect, R¹ is phenyl unsubstituted or substituted with 1–3 R³. In a specifically preferred aspect, R¹ is 3-fluorophenyl, 4-fluorophenyl, 2,4-diflourophenyl, 3,4-diflourophenyl, 3-methyl-4-fluorophenyl, 3-chloro-4-fluorophenyl, 3-chlorophenyl, 4-chlorophenyl, 3,4-dichlorophenyl, 3,5-dichlorophenyl, 3-methylphenyl, 4-methylphenyl, or 3,4-dimethylphenyl.

Preferably, R² is —H, methyl, —OH, or methoxy. More preferably, R² is —H.

Preferably, R⁶ is —C₁–C₆ alkyl. More preferably, R⁶ is methyl.

Preferably, R⁵ is heteroaryl. More preferably, R⁵ is selected from the group consisting of fluorooxindole and methyltriazole. Even more preferably, R⁵ is a 4 to 7 membered monocylic heterocycle. Still mor preferably, R⁵ is selected from the group consisting of [1,2]thiazinane 1,1-dioxide and

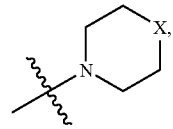

wherein X is a bond, O, S, NH, N-methyl, N-propyl, N-acetyl, N-(2-hydroxyethyl), N-pyridinyl, N-pyrazinyl, N—SO₂Me, CH₂, and CHOH.

Preferred compounds are selected from the group consisting of:
N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3,4-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(4-chlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3-chlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[3-(4-fluorophenyl)propyl]-1,6-dihydro-5-hydroxy-1-methyl-6-oxo-2-(tetrahydro-1,1-dioxido-2H-1,2-thiazin-2-yl)-4-pyrimidinecarboxamide;
N-[3-(3,4-dichlorophenyl)propyl]-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-N-[(4-methylphenyl)methyl]-6-oxo-2-(tetrahydro-1,1-dioxido-2H-1,2-thiazin-2-yl)-4-pyrimidinecarboxamide;
1,6-dihydro-5-hydroxy-1-methyl-N-[(3-methylphenyl)methyl]-6-oxo-2-(tetrahydro-1,1-dioxido-2H-1,2-thiazin-2-yl)-4-pyrimidinecarboxamide;
1,6-dihydro-5-hydroxy-N-[(4-methoxyphenyl)methyl]-1-methyl-6-oxo-2-(tetrahydro-1,1-dioxido-2H-1,2-thiazin-2-yl)-4-pyrimidinecarboxamide;
1,6-dihydro-5-hydroxy-N-[(3-methoxyphenyl)methyl]-1-methyl-6-oxo-2-(tetrahydro-1,1-dioxido-2H-1,2-thiazin-2-yl)-4-pyrimidinecarboxamide;
N-[(3,5-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(4-fluoro-3-methylphenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3-fluoro-4-methylphenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3,4-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[2-(4-fluorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(2,4-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(3-chloro-4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(3,4-dimethylphenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-N-(1-phenylethyl)-2-(tetrahydro-1,1-dioxido-2H-1,2-thiazin-2-yl)-4-pyrimidinecarboxamide;

N-[(4-fluorophenyl)methyl]-1,6-dihydro-5-hydroxy-1-methyl-2-(4-morpholinyl)-6-oxo-4-pyrimidinecarboxamide;

N-[[4-fluoro-3-(trifluoromethyl)phenyl]methyl]-1,6-dihydro-5-hydroxy-1-methyl-6-oxo-2-(tetrahydro-1,1-dioxido-2H-1,2-thiazin-2-yl)-4-pyrimidinecarboxamide;

N-[2-(3-fluorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(2,4-dimethoxyphenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-N-[(5-methyl-2-furanyl)methyl]-6-oxo-2-(tetrahydro-1,1-dioxido-2H-1,2-thiazin-2-yl)-4-pyrimidinecarboxamide;

1,6-dihydro-5-hydroxy-N-[(2-methoxyphenyl)methyl]-1-methyl-6-oxo-2-(tetrahydro-1,1-dioxido-2H-1,2-thiazin-2-yl)-4-pyrimidinecarboxamide;

N-(2,2-diphenylethyl)-1,6-dihydro-5-hydroxy-1-methyl-6-oxo-2-(tetrahydro-1,1-dioxido-2H-1,2-thiazin-2-yl)-4-pyrimidinecarboxamide;

N-[2-(4-chlorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-N-[2-(4-methoxyphenyl)ethyl]-1-methyl-6-oxo-2-(tetrahydro-1,1-dioxido-2H-1,2-thiazin-2-yl)-4-pyrimidinecarboxamide;

N-[(2-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[[3-(trifluoromethyl)phenyl]methyl]-4-pyrimidinecarboxamide;

N-[2-(3-chlorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-N-(2-phenylethyl)-2-(tetrahydro-1,1-dioxido-2H-1,2-thiazin-2-yl)-4-pyrimidinecarboxamide;

1,6-dihydro-5-hydroxy-1-methyl-6-oxo-N-[(1S)-1-phenylethyl]-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[[4-(trifluoromethyl)phenyl]methyl]-4-pyrimidinecarboxamide;

N-[1-(4-fluorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

N-(2-furanylmethyl)-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-(2-thienylmethyl)-4-pyrimidinecarboxamide;

N-(1,2-diphenylethyl)-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-N-(phenylmethyl)-2-(tetrahydro-1,1-dioxido-2H-1,2-thiazin-2-yl)-4-pyrimidinecarboxamide;

N-[(2-chlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-N-[(2-methylphenyl)methyl]-6-oxo-2-(tetrahydro-1,1-dioxido-2H-1,2-thiazin-2-yl)-4-pyrimidinecarboxamide;

1,6-dihydro-5-hydroxy-N-[2-(2-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-N-[2-(3-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-1-methyl-N-[2-(4-methylphenyl)ethyl]-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[(3,4,5-trimethoxyphenyl)methyl]-4-pyrimidinecarboxamide;

N-[(2,5-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-N-[(1R,2S)-2-hydroxy-1,2-diphenylethyl]-1-methyl-6-oxo-2-(tetrahydro-1,1-dioxido-2H-1,2-thiazin-2-yl)-4-pyrimidinecarboxamide;

N-[(2,4-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

N-[[3,5-bis(trifluoromethyl)phenyl]methyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(2,5-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[[2-(trifluoromethyl)phenyl]methyl]-4-pyrimidinecarboxamide;

1,6-dihydro-5-hydroxy-1-methyl-6-oxo-N-(1-phenylpropyl)-2-(tetrahydro-1,1-dioxido-2H-1,2-thiazin-2-yl)-4-pyrimidinecarboxamide, N-[1-(4-chlorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(3,5-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[[3-(trifluoromethoxy)phenyl]methyl]-4-pyrimidinecarboxamide;

1,6-dihydro-5-hydroxy-1-methyl-N-[1-(1-naphthalenyl)ethyl]-6-oxo-2-(tetrahydro-1,1-dioxido-2H-1,2-thiazin-2-yl)-4-pyrimidinecarboxamide;

N-[1-(4-bromophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-N-[1-(2-naphthalenyl)ethyl]-6-oxo-2-(tetrahydro-1,1-dioxido-2H-1,2-thiazin-2-yl)-4-pyrimidinecarboxamide;

1,6-dihydro-5-hydroxy-1-methyl-N-[1-(4-methylphenyl)ethyl]-6-oxo-2-(tetrahydro-1,1-dioxido-2H-1,2-thiazin-2-yl)-4-pyrimidinecarboxamide;

1,6-dihydro-5-hydroxy-N-[1-(3-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-N-[1-(4-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-N-[2-(1H-indol-3-yl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-N-[(1S)-1-phenylpropyl]-2-(tetrahydro-1,1-dioxido-2H-1,2-thiazin-2-yl)-4-pyrimidinecarboxamide;

N-(1H-benzimidazol-2-ylmethyl)-1,6-dihydro-5-hydroxy-1-methyl-6-oxo-2-(tetrahydro-1,1-dioxido-2H-1,2-thiazin-2-yl)-4-pyrimidinecarboxamide;

N-[(4-fluorophenyl)methyl]-1,6-dihydro-5-hydroxy-1-methyl-2-(3-methyl-1H-1,2,4-triazol-1-yl)-6-oxo-4-pyrimidinecarboxamide;

N-[(3,4-dichlorophenyl)methyl]-1,6-dihydro-5-hydroxy-1-methyl-2-(3-methyl-1H-1,2,4-triazol-1-yl)-6-oxo-4-pyrimidinecarboxamide;

N-[(4-fluoro-3-methylphenyl)methyl]-1,6-dihydro-5-hydroxy-1-methyl-2-(3-methyl-1H-1,2,4-triazol-1-yl)-6-oxo-4-pyrimidinecarboxamide;

N-[(3,4-dichlorophenyl)methyl]-1,6-dihydro-5-hydroxy-1-methyl-2-(4-morpholinyl)-6-oxo-4-pyrimidinecarboxamide;

N-[(3-fluoro-4-methylphenyl)methyl]-1,6-dihydro-5-hydroxy-1-methyl-2-(4-morpholinyl)-6-oxo-4-pyrimidinecarboxamide;

N-[(4-fluoro-3-methylphenyl)methyl]-1,6-dihydro-5-hydroxy-1-methyl-2-(4-morpholinyl)-6-oxo-4-pyrimidinecarboxamide;

N-[(3-chloro-4-fluorophenyl)methyl]-1,6-dihydro-5-hydroxy-1-methyl-2-(4-morpholinyl)-6-oxo-4-pyrimidinecarboxamide;

N-[(3,4-dimethylphenyl)methyl]-1,6-dihydro-5-hydroxy-1-methyl-2-(4-morpholinyl)-6-oxo-4-pyrimidinecarboxamide;

N-[(4-fluorophenyl)methyl]-1,6-dihydro-5-hydroxy-1-methyl-2-(5-methyl-1H-1,2,4-triazol-1-yl)-6-oxo-4-pyrimidinecarboxamide;

N-[(3,4-dichlorophenyl)methyl]-1,6-dihydro-5-hydroxy-1-methyl-2-(5-methyl-1H-1,2,4-triazol-1-yl)-6-oxo-4-pyrimidinecarboxamide;

N-[(4-fluorophenyl)methyl]-1,6-dihydro-5-hydroxy-2-[4-(2-hydroxyethyl)-1-piperazinyl]-1-methyl-6-oxo-4-pyrimidinecarboxamide;

N-[(4-fluoro-3-methylphenyl)methyl]-1,6-dihydro-5-hydroxy-2-[4-(2-hydroxyethyl)-1-piperazinyl]-1-methyl-6-oxo-4-pyrimidinecarboxamide;

2-(4-acetyl-1-piperazinyl)-N-[(4-fluorophenyl)methyl]-1,6-dihydro-5-hydroxy-1-methyl-6-oxo-4-pyrimidinecarboxamide;

2-(4-acetyl-1-piperazinyl)-N-[(4-fluoro-3-methylphenyl)methyl]-1,6-dihydro-5-hydroxy-1-methyl-6-oxo-4-pyrimidinecarboxamide;

N-[(4-fluorophenyl)methyl]-1,6-dihydro-5-hydroxy-1-methyl-6-oxo-2-(4-propyl-1-piperazinyl)-4-pyrimidinecarboxamide;

N-[(4-fluoro-3-methylphenyl)methyl]-1,6-dihydro-5-hydroxy-1-methyl-6-oxo-2-(4-propyl-1-piperazinyl)-4-pyrimidinecarboxamide;

N-[(4-fluorophenyl)methyl]-1,6-dihydro-5-hydroxy-1-methyl-6-oxo-2-(1-piperazinyl)-4-pyrimidinecarboxamide;

N-[(4-fluoro-3-methylphenyl)methyl]-1,6-dihydro-5-hydroxy-1-methyl-6-oxo-2-(1-piperazinyl)-4-pyrimidinecarboxamide;

N-[(4-fluorophenyl)methyl]-1,6-dihydro-5-hydroxy-2-(4-hydroxy-1-piperidinyl)-1-methyl-6-oxo-4-pyrimidinecarboxamide;

N-[(4-fluoro-3-methylphenyl)methyl]-1,6-dihydro-5-hydroxy-2-(4-hydroxy-1-piperidinyl)-1-methyl-6-oxo-4-pyrimidinecarboxamide;

2-(6-fluoro-1,3-dihydro-1-oxo-2H-isoindol-2-yl)-N-[(4-fluorophenyl)methyl]-1,6-dihydro-5-hydroxy-1-methyl-6-oxo-4-pyrimidinecarboxamide;

N-[(4-fluorophenyl)methyl]-1,6-dihydro-5-hydroxy-1-methyl-6-oxo-2-[4-(2-pyridinyl)-1-piperazinyl]-4-pyrimidinecarboxamide;

N-[(4-fluoro-3-methylphenyl)methyl]-1,6-dihydro-5-hydroxy-1-methyl-6-oxo-2-[4-(2-pyridinyl)-1-piperazinyl]-4-pyrimidinecarboxamide;

N-[(4-fluorophenyl)methyl]-1,6-dihydro-5-hydroxy-1-methyl-6-oxo-2-[4-(2-pyrimidinyl)-1-piperazinyl]-4-pyrimidinecarboxamide;

N-[(4-fluoro-3-methylphenyl)methyl]-1,6-dihydro-5-hydroxy-1-methyl-6-oxo-2-[4-(2-pyrimidinyl)-1-piperazinyl]-4-pyrimidinecarboxamide;

N-[(4-fluorophenyl)methyl]-1,6-dihydro-5-hydroxy-1-methyl-2-[4-(methylsulfonyl)-1-piperazinyl]-6-oxo-4-pyrimidinecarboxamide;

N-[(4-fluoro-3-methylphenyl)methyl]-1,6-dihydro-5-hydroxy-1-methyl-2-[4-(methylsulfonyl)-1-piperazinyl]-6-oxo-4-pyrimidinecarboxamide;

N-[(4-fluorophenyl)methyl]-1,6-dihydro-5-hydroxy-1-methyl-6-oxo-2-(1-pyrrolidinyl)-4-pyrimidinecarboxamide;

N-[(4-fluoro-3-methylphenyl)methyl]-1,6-dihydro-5-hydroxy-1-methyl-6-oxo-2-[2-(tetrahydro-1,1-dioxido-2H-1,2-thiazin-2-yl)ethyl]-4-pyrimidinecarboxamide;

N-[(4-fluorophenyl)methyl]-1,6-dihydro-5-hydroxy-1-methyl-6-oxo-2-[3-(tetrahydro-1,1-dioxido-2H-1,2-thiazin-2-yl)propyl]-4-pyrimidinecarboxamide;

N-[(4-fluorophenyl)methyl]-1,6-dihydro-5-hydroxy-1-methyl-6-oxo-2-[2-(tetrahydro-1,1-dioxido-2H-1,2-thiazin-2-yl)ethyl]-4-pyrimidinecarboxamide; and N-[(3,4-dichlorophenyl)methyl]-1,6-dihydro-5-hydroxy-1-methyl-6-oxo-2-[2-(tetrahydro-1,1-dioxido-2H-1,2-thiazin-2-yl)ethyl]-4-pyrimidinecarboxamide.

In another aspect of the invention, there is provided a compound having the formula:

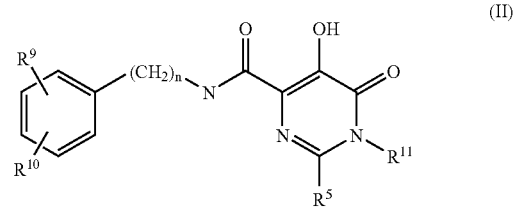

wherein, n is 1 to 4;

$R^5$ is Het wherein the bond attaching $R^5$ is made to a heteroatom in said Het;

$R^9$ and $R^{10}$ are each independently H, halo, $C_{1-6}$ alkyl, $C_{1-6}$ alkoxy or $CF_3$; and $R^{11}$ is $C_{1-6}$ alkyl;

or a pharmaceutically acceptable enantiomer, diastereomer, salt, solvate or prodrug thereof.

Preferably, $R^5$ is a $C_{4-7}$ monocyclic heterocycle. More preferably, the heterocycle is substituted with at least one of $C_{1-6}$ alkyl, $C_{1-6}$ alkoxy, $C_{1-6}$ hydroxyalkyl, $C_{1-6}$ alkyl carbonyl, $C_{6-10}$ aryl, $C_{7-14}$ alkyl, aryl, $C_{1-6}$ alkylsulfonyl, $C_{6-10}$ arylsulfonyl, $C_{1-6}$ alkylurea, $C_{3-7}$ cycloalkylurea, carbonyl, carboxamide or hydroxyl.

In another aspect of the invention, there is provided a compound having the formula:

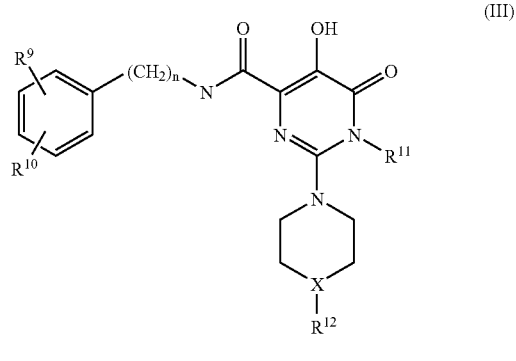

(III)

wherein n is 1 to 4;
$R^9$ and $R^{10}$ are each independently H, halo, $C_{1-6}$ alkyl, $C_{1-6}$ alkoxy or $CF_3$;
X is C, O or N;
$R^{11}$ is $C_{1-6}$ alkyl; and
$R^{12}$ is H, $C_{1-6}$ alkyl, $C_{1-6}$ alkoxy, $C_{1-6}$ hydroxyalkyl, $C_{1-6}$ alkyl carbonyl, $C_{6-10}$ aryl, $C_{7-14}$ alkyl; aryl, $C_{1-6}$ alkylsulfonyl, $C_{6-10}$ arylsulfonyl, $C_{1-6}$ alkylurea, $C_{3-7}$ cycloalkylurea, carbonyl, carboxamide or hydroxyl;
said $R^{12}$ being present only when X is C or N;
or a pharmaceutically acceptable enantiomer, diastereomer, salt, solvate or prodrug thereof.

Preferably, n is 1. Preferably, $R_9$ is halo or methyl. More preferably, $R_9$ is fluoro or chloro. Preferably, $R_{10}$ is methyl. More preferably $R_{10}$ is chloro. Preferably, $R_9$ and $R_{10}$ are not both H. Preferably, X is O or N.

Preferred compounds of the invention have the following structures:

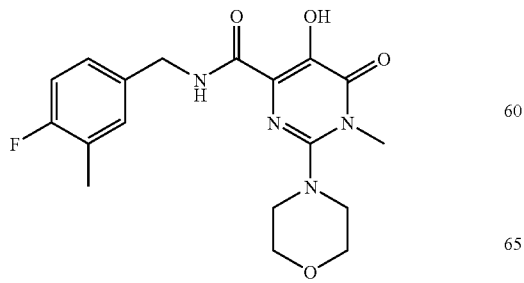

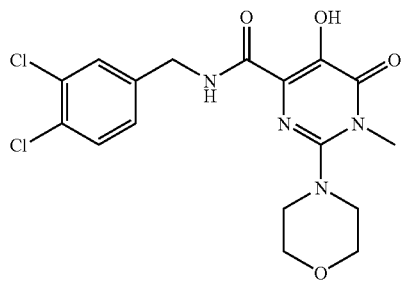

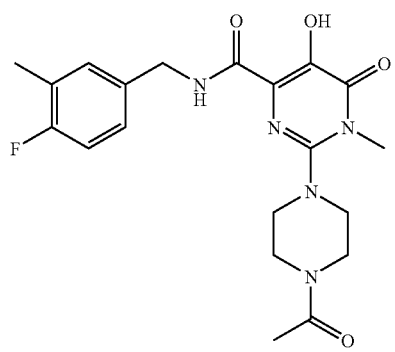

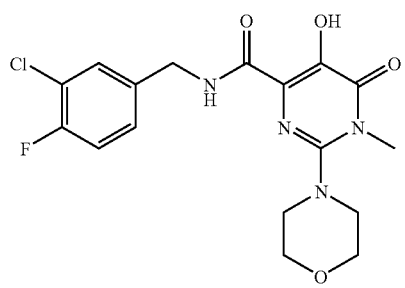

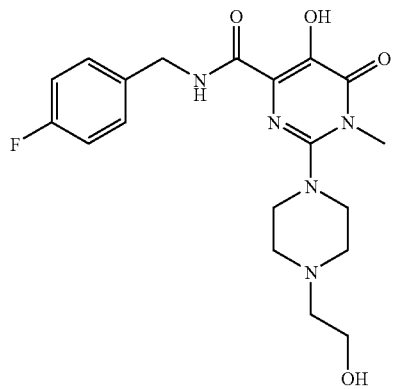

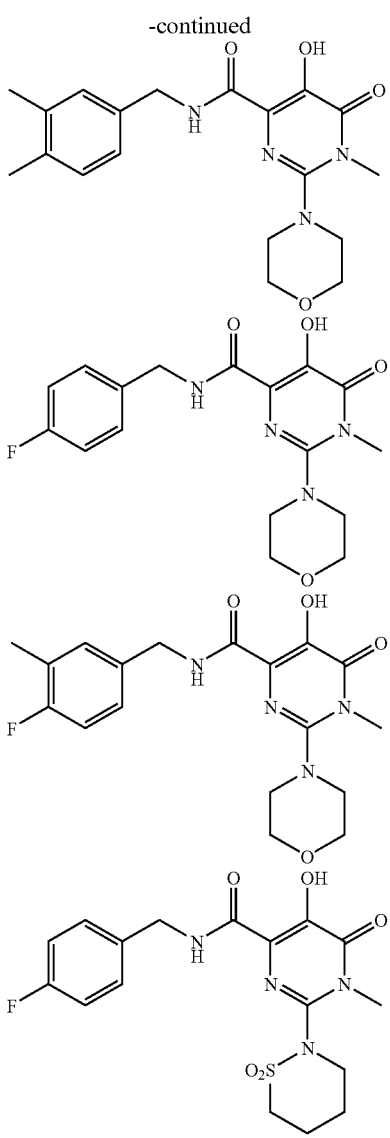

The compounds of the present invention, which are substituted with a basic group, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

The present invention includes both enantiomers and mixtures of enantiomers such as racemic mixtures.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of the present invention may be in the form of a prodrug. Simple aliphatic or aromatic esters derived from, when present, acidic groups pendent on the compounds of this invention are preferred prodrugs. In some cases it is desirable to prepare double ester type prodrugs such as (acyloxy) alkyl esters or (alkoxycarbonyl)oxy)alkyl esters.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The starting materials useful to synthesize the compounds of the present invention are known to those skilled in the art and can be readily manufactured or are commercially available.

The compounds of the present invention can be manufactured by methods known to those skilled in the art, see e.g., (Sunderland, J. S.; Botta, M.; Aime, S.; Raymond, K. N. Inorg. Chem. (2001), 40, 6756–6756). The following methods set forth below are provided for illustrative purposes and are not intended to limit the scope of the claimed invention. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

reductive conditions, oxidative conditions or acidic conditions. Protecting groups, R, useful for the synthesis of compounds such as 1–9 can be found in Greene, T. W. and Wutz, P. G. M. Protective Groups in Organic Synthesis, Second Edition, 1991, John Wiley and Sons, New York. In the alternative pathway, the protecting group is removed from 1–6 to yield 1–9. At elevated temperatures 1–9 reacts with amines to afford 1–10.

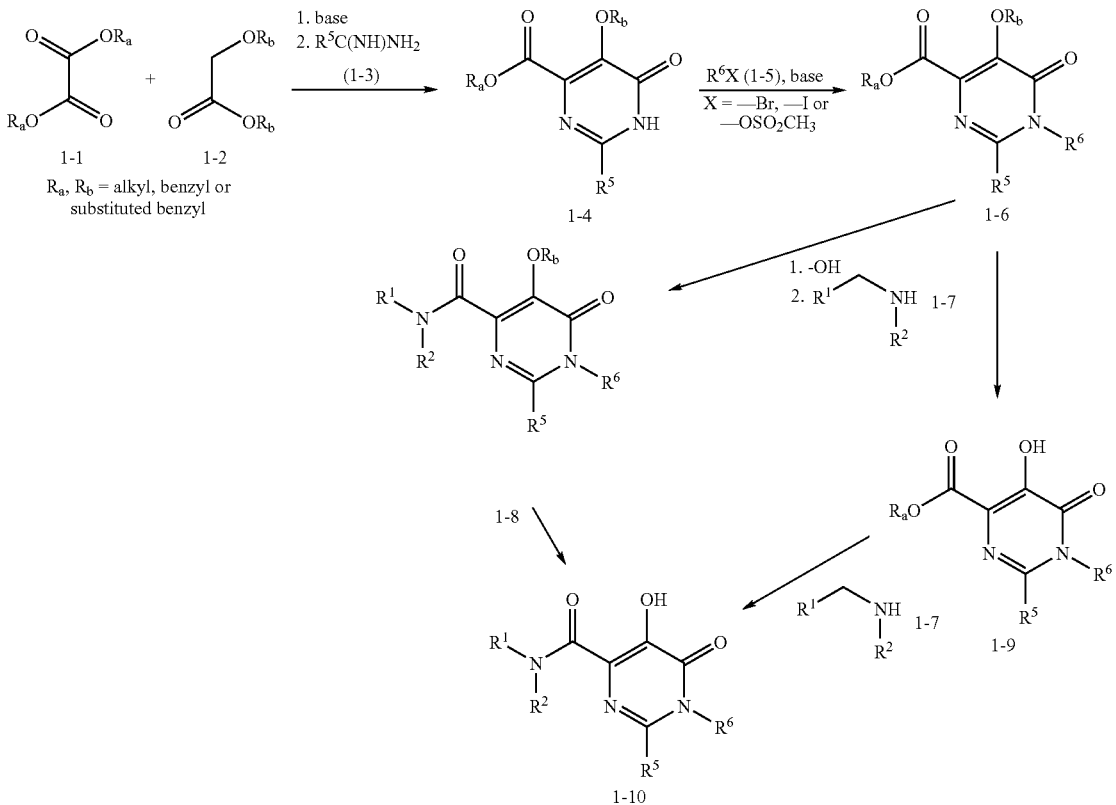

Scheme I

The compounds of the present invention can be synthesized according to Scheme I. In Scheme I, an oxalic acid diester 1—1 is condensed with glycolate 1–2 using sodium hydride or a similar base. The intermediate generated from this reaction can be isolated but more often is reacted in one pot with an appropriately substituted amidine (1–3) to yield the pyrimidinone heterocycle 1–4. This is alkylated with a suitable electrophile, 1–5, under basic conditions. From here there are two alternative pathways to the final product. In one path intermediate 1–6 is treated with base to saponify the ester and the resulting acid coupled with amine 1–7. It will be appreciated by those skilled in the art that the amide coupling reaction can be carried out under a variety of conditions such as those disclosed in Jerry March, Advanced Organic Chemistry, 3$^{rd}$ edition, John Wiley & Sons, 1985. The resulting amide, 1–8 is then treated under conditions appropriate for cleaving the protecting group $R_b$ to yield 1–10. Where $R_b$ is alkyl, this can be accomplished by $BBr_3$ or other conditions familiar to those skilled in the art, such as treatment with LiI. Alternatively when $R_b$ is a benzylic or substituted benzylic group the ether can be cleaved under In Scheme II, an alternative pathway is shown in which the $R^5$ group is introduced at a later stage of the synthesis. Thus, 2—2 is formed from an oxalate ester, protected glycolic acid and S-methyl-thiourea using the same conditions as described in Scheme I. Likewise, this intermediate is carried through the same sequence of reactions described in Scheme I to yield 2–4. The thiomethyl group is then displaced with a nitrogen containing heterocylce, such as those shown in the scheme, under acidic conditions (HCl) similar to those described in Ple, N.; Turck, Heynderick, A.; Queguiner, G. J. Heterocycl. Chem. (1997) 34, 551–556, for example, or after oxidation of the sulphur atom as described in Jacobs, R. T.; Mauger, R. C.; Ulatowski, T. G.; Aharony, D.; Buckner, C. K. Bioorg. Med. Chem. Lett. (1995), 23, 2879–2884. Following the installation of the amine at C2 of the pyrimidine template there are two alternative pathways for introducing the amide group. These are essentially the same as those described in Scheme I

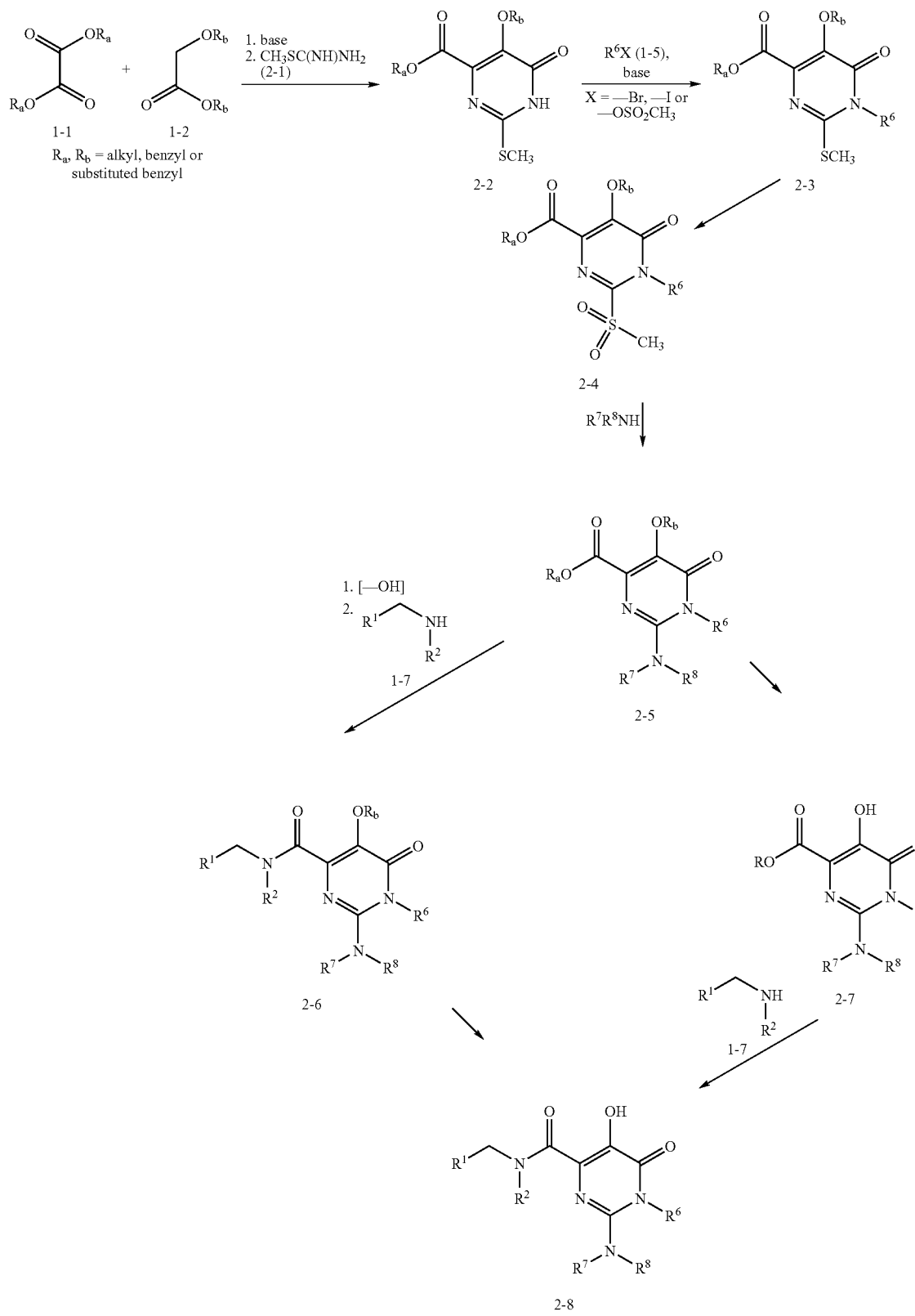

A different route to intermediate 2–3 is shown in scheme III. Methylthiocyanate reacts with appropriately substituted amines to form N-hydroxyl amidines such as 3–2. This intermediate will react with an alkyne-diester to afford a mixture of 3–4 and 3–5. Both of these compounds will rearrange to form the hydroxypyrimidinone template (Culbertson, T. P.; J. Heterocyclic Chem. (1979) 16, 1423–1424.). The in-situ reaction with an appropriate electrophile results in 2–3.

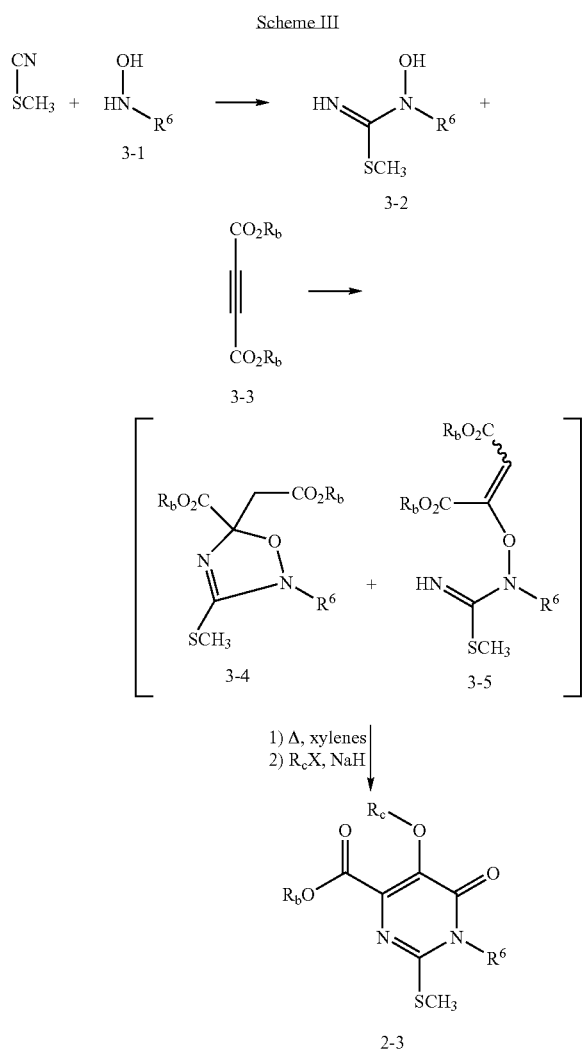

The compounds of the present invention can, for example, be preferably synthesized according to Scheme I. In Scheme I, an oxalic acid diester 1-1 is condensed with glycolate 1-2 using sodium hydride or a similar base. The intermediate generated from this reaction can be isolated but more often is reacted in one pot with an appropriately substituted amidine (1-3) to yield the pyrimidinone heterocycle 1-4. This is alkylated with a suitable electrophile, 1-5, under basic conditions. Intermediate 1-6 is treated with base to saponify the ester and the resulting acid coupled with amine 1-7. It will be appreciated by those skilled in the art that the amide coupling reaction can be carried out under a variety of conditions such as those disclosed in Jerry March, Advanced Organic Chemistry, 3$^{rd}$ edition, John Wiley & Sons, 1985. The resulting amide, 1-8 is then treated under conditions appropriate for cleaving the protecting group R. For alkyl groups, where R is alkyl, this can be accomplished by $BBr_3$ or other conditions familiar to those skilled in the art, such as treatment with LiI. Alternatively when R is a benzylic or substituted benzylic group the ether can be cleaved under reductive conditions, oxidative conditions or acidic conditions. Protecting groups, R, useful for the synthesis of compounds such as 1-9 can be found in Greene, T. W. and Wutz, P. G. M. Protective Groups in Organic Synthesis, Second Edition, 1991, John Wiley and Sons, New York.

A preferred intermediate for use in accordance with the present invention is a compound of the formula:

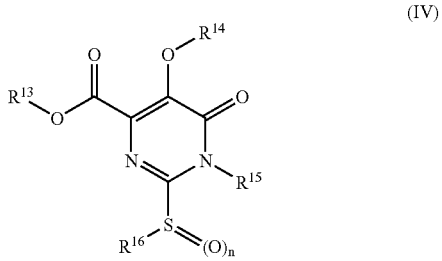

wherein;

n is 0, 1 or 2;

$R^{13}$ is —H, —$C_{1-6}$ alkyl, $C_{1-6}$ cycloalkyl, -aryl, $C_{1-6}$ alkyl-cycloalkyl, —$C_{1-6}$ alkyl-aryl, or —$C_{1-6}$ alkyl-diaryl, $R^{14}$ is —H, —$C_{1-6}$ alkyl, $C_{1-6}$ cycloalkyl, -aryl, $C_{1-6}$ alkyl-aryl, or —$C_{1-6}$ alkyl-diaryl, $R^{15}$ is —H, —$C_{1-6}$ alkyl, $C_{1-6}$ alkyl-cycloalkyl, -aryl, or —$C_{1-6}$ alkyl-aryl, and $R^{16}$ is —H, —$C_1$–$C_6$ alkyl, $C_{1-6}$ cycloalkyl, -aryl, $C_{1-6}$ alkyl-aryl, or —$C_{1-6}$ alkyl-diaryl.

The present invention also provides compositions comprising a compound of the present invention, or a pharmaceutically acceptable enantiomer, diastereomer, salt, solvate or prodrug thereof, and a pharmaceutically acceptable carrier. Pharmaceutical compositions of the present invention comprise a therapeutically effective amount of a compound of the invention, or a pharmaceutically acceptable enantiomer, diastereomer, salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

Thus, in one aspect of the invention, there is provided a composition comprising the compound of formula 1 and a pharmaceutically acceptable carrier. Preferably, the composition further comprises a compound having anti-HIV activity. As used herein, the term "anti-HIV activity" means the compound is effective to inhibit the function of a target selected from the group consisting of HIV protease, a nucleoside reverse transcriptase, a non-nucleoside reverse transcriptase or HIV entry. Often, the other compound having anti-HIV activity is effective to inhibit the function of target in the HIV life cycle other than HIV integrase.

In a preferred aspect of the invention, the compound having anti-HIV activity is a small molecule compound. As used herein, the term "small molecule compound" means a compound having a molecular weight of less than 1,500 daltons, preferably less than 1000 daltons. Preferably, the small molecule compound is effective to inhibit the function of a target selected from the group consisting of HIV protease, a nucleoside reverse transcriptase, a non-nucleoside reverse transcriptase or HIV entry.

Preferred compounds having anti-HIV activity include those selected from the group consisting of HIV protease inhibitors, nucleoside reverse transcriptase inhibitors, non-nucleoside reverse transcriptase inhibitors, HIV-entry inhibitors, immunomodulators, antiinfectives, and vaccines.

Thus the present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

TABLE 1

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| Reyataz ™ atazanavir sulfate | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |

TABLE 1-continued

| Drug Name | Manufacturer | Indication |
|---|---|---|
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |

TABLE 1-continued

| Drug Name | Manufacturer | Indication |
|---|---|---|
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |
| Fuzeon ® (or T-20) | Roche/Trimeris | HIV infection AIDs, viral Fusion inhibitor |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355–1362;

CELL, Vol. 9, pp. 243–246, Oct. 29, 1999; and DRUG DISCOVERY TODAY, Vol. 5, No. 5, May 2000, pp. 183–194.

It will be understood that the scope of combinations of the compounds of this invention with AIDS antivirals, immunomodulators, anti-infectives, HIV entry inhibitors or vaccines is not limited to the list in the above Table 1, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenyl-methyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Other suitable carriers for the above noted compositions can be found in standard pharmaceutical texts, e.g. in "Remington's Pharmaceutical Sciences", 19th ed., Mack Publishing Company, Easton, Penn., 1995.

The pharmaceutical compositions can be prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HIV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable enantiomers, diastereomers, salts, solvates or prodrugs are formulated together with a pharmaceutically acceptable carrier, the resulting composition may be administered in vivo to mammals, such as man, to inhibit HIV integrase or to treat or prevent HIV virus infection.

Accordingly, another aspect of this invention provides methods of inhibiting HIV integrase activity in patients by administering a compound of the present invention or a pharmaceutically acceptable enantiomer, diastereomer, salt or solvate thereof.

In one aspect of the invention, there is provided a method of treating an HIV infection in a patient, comprising administering to the patient a therapeutically effective amount of the compound of the invention, or a pharmaceutically acceptable enantiomer, diastereomer, solvate, prodrug or salt thereof.

Preferably, the method of administering the compound is effective to inhibit the function of the HIV integrase. In a preferred aspect, the method further comprises administering another compound having anti-HIV activity (as described above) prior to, after or concurrently with a compound of the invention.

The compounds of the invention may also be used as laboratory reagents. Compounds may be instrumental in providing research tools for designing of viral replication assays, validation of animal assay systems and structural biology studies to further enhance knowledge of the HIV disease mechanisms. Further, the compounds of the present invention are useful in establishing or determining the binding site of other antiviral compounds, for example, by competitive inhibition.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the invention can be used for the manufacture of a medicament for treating HIV infection in a patient.

EXAMPLES

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents.

The abbreviations used herein are conventional abbreviations widely employed in the art. Some of which are: calcd (calculated); DMSO (dimethylsulfoxide); EtOAc (ethyl acetate); HPLC (high-pressure liquid chromatography); LC/MS (liquid chromatography, mass spectroscopy); LDA (lithium diisopropyl amide); LiHMDS (lithium bis(trimethylsilyl)amide); $SiO_2$ (silica gel); THF (tetrahydrofuran), TFA (trifluoroacetic acid), Me (methyl), Et (ethyl), Ph (phenyl), tBuOK (potassium tert-butoxide), NaOMe (sodium methoxide), NaOEt (sodium ethoxide), Boc (tert-butoxycarbonyl), and DEAD (diethylazo dicarboxylate).

Example 1

Preparation of N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide Compound 1A 5-Methoxy-2-methylsulfanyl-6-oxo-1,6-dihydro-pyrimidine-4-carboxylic acid ethyl ester

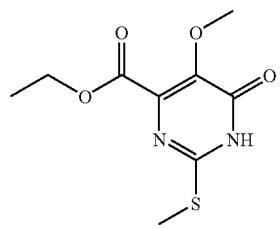

A solution of diethyl oxalate (27.2 g, 0.186 mol) and methyl methoxyacetate (19.38 g, 0.186 mol) in dry tetrahydrofuran (250 ml) was treated at 22° C. with sodium hydride (8.15 g of a 60% dispersion in mineral oil, 0.203 mol) and the resulting mixture was stirred at 22° C. for 18 h. The tetrahydrofuran was then evaporated under reduced pressure and the residual orange syrup was dissolved in a solution of sodium ethoxide (0.189 mol, prepared from 4.35 g of sodium) in ethanol (300 ml). Then powdered 2-methyl-2-thiopseudourea sulfate (25.9 g, 0.093 mol) was added and the resulting mixture was stirred at 22° C. for 1 h and then heated at 60° C. for 2 h. Acetic acid (5 ml) was then added to the gel like reaction mixture and the ethanol was evaporated under reduced pressure. The residual paste was partitioned between water and dichloromethane and the aqueous phase was extracted five times with dichloromethane. The combined organic phases were washed with brine and dried over anhydrous magnesium sulfate. Evaporation of the solvent gave a semi-solid residue which was triturated with ethyl acetate (100 ml). The light yellow solid formed was collected (10.02 g) and chromatographed on silica gel. Elution with a mixture of dichloromethane and ethanol (98:2) gave 6.02 g (13% yield) of the title ester as white needles; mp 171–173° C. (ethyl acetate). $^1$HNMR 400 MHz ($CDCl_3$) δ (ppm): 1.42 (3H, t, J=7.1 Hz, $CH_3$), 2.62 (3H, s, $SCH_3$), 3.99 (3H, s, $OCH_3$), 4.43 (2H, q, J=7.1 Hz, $CH_2$), 11.8 (1H, broad s, NH). Anal. Calcd for $C_9H_{12}N_2O_4S$: C 44.25; H, 4.95; N, 11.47. Found: C 44.22; H, 5.04; N, 11.46.

Compound 1B

5-Methoxy-1-methyl-2-methylsulfanyl-6-oxo-1,6-dihydro-pyrimidine-4-carboxylic acid ethyl ester

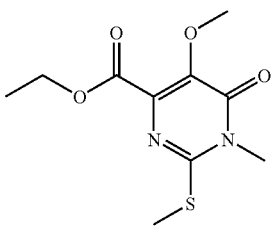

A solution of 5-methoxy-2-methylsulfanyl-6-oxo-1,6-dihydro-pyrimidine-4-carboxylic acid ethyl ester (0.442 g, 1.81 mmol) in dry N,N-dimethylformamide (5 ml) was treated at 10° C. with sodium hydride (0.080 g of a 60% dispersion in mineral oil, 2.0 mmol) and the resulting mixture was stirred for 10 min. Then iodomethane (0.123 ml, 2.0 mmol) was added and the mixture was stirred for another 1 h. The solvent was then evaporated in vacuo and the residue was diluted with ethyl acetate, washed with saturated sodium bicarbonate, brine and dried over anhydrous magnesium sulfate. Evaporation of the solvent and chromatography of the residue on silica gel (elution toluene-ethyl acetate 9:1) gave 0.419 g (89% yield) of the title ester as white needles; mp 74.5–76° C. (ether-hexane). $^1$HNMR 400 MHz (CDCl$_3$) δ (ppm): 1.41 (3H, t, J=7.1 Hz, CH$_3$), 2.62 (3H, s, SCH$_3$), 3.55 (3H, s, NCH$_3$), 3.95 (3H, s, OCH$_3$), 4.43 (2H, q, J=7.1 Hz, CH$_2$). Anal. Calcd for C$_{10}$H$_{14}$N$_2$O$_4$S: C 46.50, H 5.46; N, 10.85. Found: C 46.73; H, 5.21; N, 10.93.

Compound 1C

2-Methanesulfonyl-5-methoxy-1-methyl-6-oxo-1,6-dihydro-pyrimidine-4-carboxylic acid ethyl ester

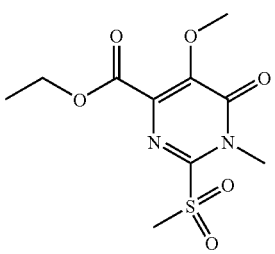

A solution of 5-methoxy-1-methyl-2-methylsulfanyl-6-oxo-1,6-dihydro-pyrimidine-4-carboxylic acid ethyl ester (0.410 g, 1.58 mmol) in dry dichloromethane (30 ml) was treated at 20° C. with 3-chloroperoxybenzoic acid (0.71 g of 85%, 3.5 mmol) and the resulting clear solution was stirred for 3 h. The reaction mixture was then diluted with ethyl acetate, washed successively with 10% sodium bisulfite, saturated sodium bicarbonate, brine and dried over anhydrous magnesium sulfate. Evaporation of the solvent and chromatography of the residue on silica gel (elution toluene-ethyl acetate 9:1) gave 0.340 g (74% yield) of the title ester as white needles; mp 75–76° C. (ethyl acetate-hexane). $^1$HNMR 400 MHz (CDCl$_3$) δ (ppm): 1.36 (3H, t, J=7.1 Hz, CH$_3$), 3.43 (3H, s, SO$_2$CH$_3$), 3.84 (3H, s, NCH$_3$), 4.07 (3H, s, OCH$_3$), 4.37 (2H, q, J=7.1 Hz, CH$_2$). Anal. Calcd for C$_{10}$H$_{14}$N$_2$O$_6$S: C, 41.37; H, 4.86; N, 9.65. Found: C, 41.21; H, 4.64; N, 9.55.

Compound 1D 2-(1,1-Dioxo-1λ$^6$-[1,2]thiazinan-2-yl)-5-methoxy-1-methyl-6-oxo-1,6-dihydro-pyrimidine-4-carboxylic acid ethyl ester

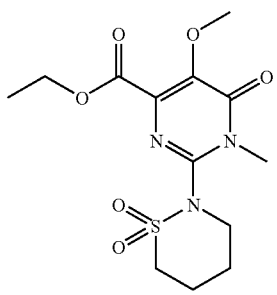

A solution of 2-methanesulfonyl-5-methoxy-1-methyl-6-oxo-1,6-dihydro-pyrimidine-4-carboxylic acid ethyl ester (0.180 g, 0.62 mmol) and [1,2]thiazinane 1,1-dioxide (0.100 g, 0.74 mmol) (W. Dirscherl and K. Otto, Chem. Ber. 89, 1956, 393) in dry N,N-dimethylformamide (2 ml) was cooled to 10° C. and treated under argon with sodium hydride (0.035 g of a 60% dispersion in mineral oil, 0.9 mmol) and the resulting mixture was stirred for 1 h. The solvent was then evaporated in vacuo, the residue was dissolved in ethyl acetate, washed with saturated sodium bicarbonate, brine and dried over anhydrous magnesium sulfate. Evaporation of the solvent and chromatography of the residue on silica gel (elution toluene-ethyl acetate 7:3) gave 0.183 g (86% yield) of the title ester as a clear oil. $^1$HNMR 400 MHz (CDCl$_3$) δ (ppm): 1.41 (3H, t, J=7.1 Hz, CH$_3$), 1.65 (1H, m, CH), 2.3–2.6 (3H, m, CH$_2$ and CH), 3.2 (1H, m, CH), 3.6 (1H, m, CH), 3.64 (3H, s, NCH$_3$), 3.65 (1H, m, CH), 4.04 (3H, s, OCH$_3$), 4.05 (1H, m, CH), 4.41 (2H, q, J=7.1 Hz, OCH$_2$). HRMS (FAB POS) calculated for C$_{13}$H$_{20}$N$_3$O$_6$S [M+H$^+$]: 346.107282. found: 346.107961.

Compound 1E 2-(1,1-Dioxo-1λ$^6$-[1,2]thiazinan-2-yl)-5-methoxy-1-methyl-6-oxo-1,6-dihydro-pyrimidine-4-carboxylic acid

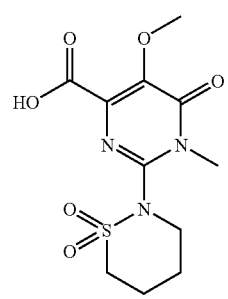

A solution of 2-(1,1-dioxo-1λ⁶-[1,2]thiazinan-2-yl)-5-methoxy-1-methyl-6-oxo-1,6-dihydro-pyrimidine-4-carboxylic acid ethyl ester (0.180 g, 0.52 mmol) in 90% ethanol (10 ml) was treated at 22° C. 1 N with sodium hydroxide (1 ml) and the resulting mixture was stirred for 30 min. Then 1 N hydrochloric acid (2 ml) was added and the ethanol was evaporated under reduced pressure. The residue was dissolved in ethyl acetate, washed with brine and dried over anhydrous magnesium sulfate. Evaporation of the solvent and recrystallization of the solid residue from ethyl acetate gave 0.133 g (81% yield) of the title acid as a white crystals; mp 180–181° C. ¹HNMR 400 MHz (DMSO-$d_6$) δ (ppm): 1.55–1.6 (1H, m, CH), 2.0–2.25 (3H, m, $CH_2$ and CH), 3.43 (2H, m, $CH_2$), 3.44 (3H, s, $NCH_3$), 3.75 (2H, m, $CH_2$), 3.83 (3H, s, $OCH_3$). Anal. Calcd for $C_{11}H_{15}N_3O_6S$: C, 41.64; H, 4.76; N, 13.24. Found: C, 41.84; H, 4.96; N, 12.88.

Compound 1F 2-(1,1-Dioxo-1λ⁶-[1,2]thiazinan-2-yl)-5-methoxy-1-methyl-6-oxo-1,6-dihydro-pyrimidine-4-carboxylic acid 4-fluoro-benzylamide

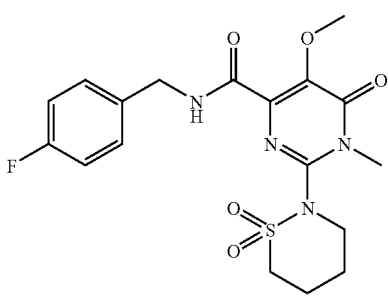

A mixture of 2-(1,1-dioxo-1λ⁶-[1,2]thiazinan-2-yl)-5-methoxy-1-methyl-6-oxo-1,6-dihydro-pyrimidine-4-carboxylic acid (0.235 g, 0.74 mmol) and 4-fluorobenzylamine (0.14 g, 1.13 mmol) in acetonitrile (10 ml) was treated at 22° C. with triethylamine (0.32 ml, 2.3 mmol) followed by benzotriazole-1-yloxy-tris-pyrrolidino-phosphonium hexafluorophosphate (0.42 g, 0.81 mmol) and the resulting mixture was stirred for 3 h. The reaction mixture was then diluted with ethyl acetate, washed with saturated sodium bicarbonate, brine and dried over anhydrous magnesium sulfate. Evaporation of the solvent and chromatography of the residue on silica gel (elution toluene-ethyl acetate 1:1 to ethyl acetate) gave 0.291 g (92% yield) of the title amide as a white solid. ¹HNMR 400 MHz ($CDCl_3$) δ (ppm): 1.6–1.7 and 2.3–2.5 (4H, m, 2×$CH_2$), 3.2 and 3.5 (2×1H, m, $CH_2$), 3.62 (3H, s, $NCH_3$), 3.7 and 3.95 (2×1H, m, $CH_2$), 4.04 (3H, s, $OCH_3$), 4.59 (2H, d, J=5.8 Hz, $NCH_2$), 7.04 (2H, m, aromatics), 7.31 (2H, m, aromatics), 7.75 (1H, broad, NH). HRMS (FAB POS) calculated for $C_{18}H_{22}FN_4O_5S$ [M+H⁺]: 425.129495. found: 425.129040.

Compound 1

N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide

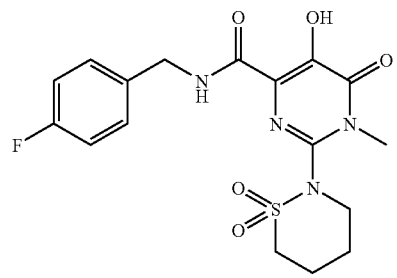

A mixture of 2-(1,1-dioxo-1λ⁶-[1,2]thiazinan-2-yl)-5-methoxy-1-methyl-6-oxo-1,6-dihydro-pyrimidine-4-carboxylic acid 4-fluoro-benzylamide (0.115 g, 0.27 mmol) in 2,4,6-collidine (3 ml) was treated with lithium iodide (0.060 g) and the resulting mixture was heated at 120° C. for 30 min. The collidine was then evaporated in vacuo, the residue was diluted with a small volume of water and the pH was adjusted to a value of 7 with 0.1 N hydrochloric acid. The aqueous phase was extracted three times with dichloromethane and the combined organic extracts were washed with brine, dried over anhydrous magnesium sulfate and concentrated under reduced pressure. The residue was purified by chromatography on reversed phase silica gel (Waters, C-18, 125 A, elution with water-acetonitrile 7:3 to 6:4) to give 0.058 g (52% yield) of the title amide as a white solid; mp 226–227° C. (dichloromethane-ethanol).

Compound 1G

5-Benzyloxy-2-methylsulfanyl-6-oxo-1,6-dihydro-pyrimidine-4-carboxylic acid ethyl ester

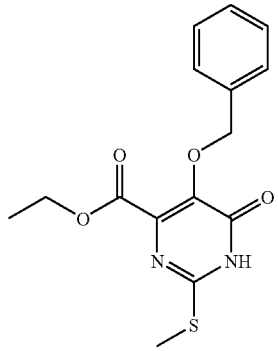

A solution of diethyl oxalate (21.06 g, 0.144 mol) and ethyl benzyloxyacetate (28.0 g, 0.144 mol) in dry tetrahydrofuran (200 ml) was treated at 22° C. with sodium hydride (6.34 g of a 60% dispersion in mineral oil, 0.158 mol). Ethanol (0.05 ml) was added and the resulting mixture was stirred at 22° C. for 18 h. The tetrahydrofuran was then evaporated under reduced pressure and the residual orange syrup was dissolved in a solution of sodium ethoxide (0.072 mol, prepared from 1.65 g of sodium) in ethanol (200 ml).

Then powdered 2-methyl-2-thiopseudourea sulfate (20.1 g, 0.072 mol) was added and the resulting mixture was heated at 60° C. for 6 h. Acetic acid (5 ml) was then added to the gel like reaction mixture and the ethanol was evaporated under reduced pressure. The residual paste was partitioned between water and dichloromethane and the aqueous phase was extracted twice with dichloromethane. The combined organic phases were washed with saturated sodium bicarbonate, brine, dried over anhydrous magnesium sulfate and concentrated under reduced pressure. Chromatography on silica gel (elution with a gradient of ethyl acetate 0–20% in toluene) followed by crystallization from ethyl acetate-hexane gave 8.34 g (18% yield) of the title ester as white needles; mp 109–110° C. $^1$HNMR 400 MHz (CDCl$_3$) δ (ppm): 1.35 (3H, t, J=7.1 Hz, CH$_3$), 2.62 (3H, s, SCH$_3$), 4.37 (2H, q, J=7.1 Hz, CH$_2$), 5.28 (2H, s, OCH$_2$), 7.35–7.52 (5H, m, aromatics), 12.2 (1H, broad s, NH). Anal. Calcd for C$_{15}$H$_{16}$N$_2$O$_4$S: C 56.23, H 5.03, N 8.74. Found: C 56.23, H 4.86, N 8.76.

Compound 1H

5-Benzyloxy-1-methyl-2-methylsulfanyl-6-oxo-1,6-dihydro-pyrimidine-4-carboxylic acid ethyl ester

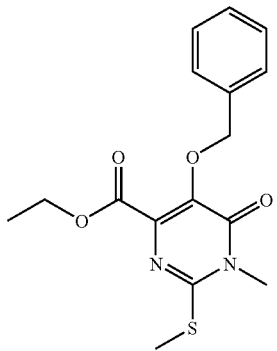

Method 1: 5-Benzyloxy-2-methylsulfanyl-6-oxo-1,6-dihydro-pyrimidine-4-carboxylic acid ethyl ester (6.190 g, 19.32 mmol) in dry N,N-dimethylformamide (60 ml) was reacted at 10° C. with sodium hydride (0.90 g of a 60% dispersion in mineral oil, 22.5 mmol) and iodomethane (1.4 ml, 21.7 mmol) and chromatographed to give first 0.581 g (9% yield) of 5-benzyloxy-6-methoxy-2-methylsulfanyl-pyrimidine-4-carboxylic acid ethyl ester as white crystals; mp 48–49° C. (ethyl acetate-hexane). $^1$HNMR 400 MHz (CDCl$_3$) δ (ppm): 1.32 (3H, t, J=7.1 Hz, CH$_3$), 2.56 (3H, s, SCH$_3$), 4.07 (3H, s, OCH$_3$), 4.36 (2H, q, J=7.1 Hz, CH$_2$), 5.04 (2H, s, OCH$_2$), 7.3–7.45 (5H, m, aromatics). HRMS (FAB POS) calculated for C$_{16}$H$_{19}$N$_2$O$_4$S [M+H$^+$]: 335.106554. found: 335.106641, δ −0.3 ppm. The following fractions then gave 5.836 g (90% yield) of the title ester as white needles; mp 84–85° C. (ethyl acetate-hexane). $^1$HNMR 400 MHz (CDCl$_3$) δ (ppm): 1.33 (3H, t, J=7.0 Hz, CH$_3$), 2.62 (3H, s, SCH$_3$), 3.57 (3H, s, NCH$_3$), 4.35 (2H, q, J=7.0 Hz, CH$_2$), 5.22 (2 H, s, OCH$_2$), 7.3–7.5 (5H, m, aromatics). Anal. Calcd for C$_{16}$H$_{18}$N$_2$O$_4$S: C 57.47, H 5.43, N 8.38. Found: C 57.37, H 5.42, N 8.36.

Method 2: To a stirred solution of methylthiocyanate (91 g, 1.245 Moles) and N-methylhydroxylamine hydrochloride (100 g, 1.197 Moles) in 1:1 ethanol/water (v/v, 500 mL) was carefully added Na$_2$CO$_3$ (63.6 g, 0.6 Moles) over 30 min at room temperature. The resulting reaction mixture was stirred 48 h then cooled in an ice-water bath. To this was slowly added diethyl acetylenedicarboxylate (192 mL, 1.2 Moles) over 10 minutes. After stirring 2 h, the resulting dark-brown reaction mixture was transferred to a separatory funnel and extracted with ethyl acetate (3×250 mL). The combined organic layers were dried (Na$_2$SO$_4$/activated charcoal), filtered and concentrated to give dark-brown residue (310.1 g) which was used in the next step without further purification.

A solution of the above crude intermediate in xylenes (1.2 L) was placed in a pre-heated oil bath (140° C.) and stirred for 48 h. The mixture was then cooled and concentrated to give a dark solid. This crude product mixture was dissolved into anhydrous DMF (1.5 L) to which was added benzyl bromide (119 mL, 1 Mole) followed by K$_2$CO$_3$ (138 g, 1 Mole). After stirring for 72 h at room temperature, the reaction mixture was diluted with hexanes (1 L) and filtered. The filtrate was concentrated under vacuum and the resulting residue was taken up into ether (1 L), washed with water (3×250 mL) and brine (200 mL). The organic layer was dried (Na$_2$SO$_4$/activated charcoal), filtered and concentrated to afford dark paste which was dissolved in ether/hexanes (2:1, 1.5 L). Approximately 1 L of the solvent was removed on a rotary evaporator. The resulting solution was left overnight at room temperature and the brown-crystals which formed were removed by filtration. The filtrate was concentrated then chromatoghraphed (EM Science silica gel 60, column size ~30×10 cm$^2$) using 8:1:1 Hexanes/ETOAc/CH$_2$Cl$_2$ solvent system and collected into 250 mL fractions. The fractions containing the desired compound were combined and concentrated to give a viscous oil which was dissolved into Hex/Et$_2$O (~4:1) and allowed to crystallize (92.3 g). An additional 8.84 grams of product was isolated after the mother liquor was concentrated and allowed to sit for 48 h Resulting in a total yield 101.14 g (25.3% yield).

Compound 1I

5-Benzyloxy-2-methanesulfonyl-1-methyl-6-oxo-1,6-dihydro-pyrimidine-4-carboxylic acid ethyl ester

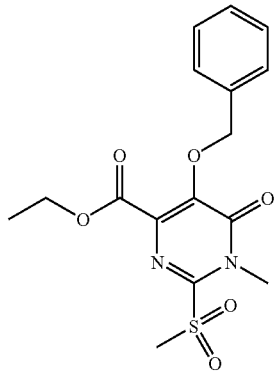

Reaction of 5-benzyloxy-1-methyl-2-methylsulfanyl-6-oxo-1,6-dihydro-pyrimidine-4-carboxylic acid ethyl ester (5.83 g, 17.43 mmol) in dry dichloromethane (250 ml) with 3-chloroperoxybenzoic acid (12.5 g of 85%, 61.6 mmol) gave 5.27 g (82% yield) of the title ester as white needles; mp 65–67° C. (ethyl acetate-hexane). $^1$HNMR 400 MHz (CDCl$_3$) δ (ppm): 1.30 (3H, t, J=7.1 Hz, CH$_3$), 3.45 (3H, s, SO$_2$CH$_3$), 3.87 (3H, s, NCH$_3$), 4.32 (2H, q, J=7.1 Hz, CH$_2$), 5.42 (2H, s, OCH$_2$), 7.3–7.5 (5H, m, aromatics). Anal. Calcd for C$_{16}$H$_{18}$N$_2$O$_6$S: C 52.45, H 4.95, N 7.65. Found: C 52.27, H 4.69, N 7.58.

Compound 1J 2-(1,1-Dioxo-1λ$^6$-[1,2]thiazinan-2-yl)-5-benzyloxy-1-methyl-6-oxo-1,6-dihydro-pyrimidine-4-carboxylic acid ethyl ester

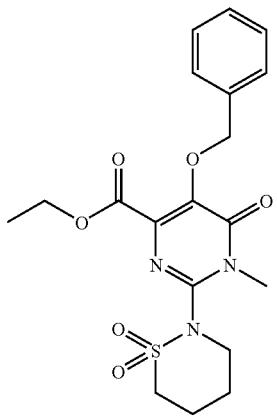

Reaction of 2-methanesulfonyl-5-benzyloxy-1-methyl-6-oxo-1,6-dihydro-pyrimidine-4-carboxylic acid ethyl ester (2.21 g, 6.03 mmol) and [1,2]thiazinane 1,1-dioxide (0.97 g, 7.2 mmol) in dry N,N-dimethylformamide (30 ml) with sodium hydride (0.35 g of a 60% dispersion in mineral oil, 8.8 mmol) gave 2.35 g (92% yield) of the title ester as white needles; mp 109–110° C. $^1$HNMR 400 MHz (CDCl$_3$) δ (ppm): 1.29 (3H, t, J=7.1 Hz, CH$_3$), 1.62 (1H, m, CH), 2.3–2.6 (3H, m, CH$_2$ and CH), 3.15–3.21 (1H, m, CH), 3.5–3.6 (1H, m, CH), 3.64 (3H, s, NCH$_3$), 3.64 (1H, m overlapping with NCH$_3$, CH), 3.97–4.05 (1H, m, CH), 4.32 (2H, q, J=7.1 Hz, OCH$_2$), 5.29 (2H, AB system, J$_{AB}$=10.6 Hz, Δv=62.5 Hz, OCH$_2$), 7.3–7.5 (5H, m, aromatics). Anal. Calcd for C$_{19}$H$_{23}$N$_3$O$_6$S: C 54.15, H 5.50, N 9.97. Found: C 53.88, H 5.40, N 9.91.

Compound 1K 2-(1,1-Dioxo-1λ$^6$-[1,2]thiazinan-2yl)-5-hydroxy-1-methyl-6-oxo-1,6-dihydro-pyrimidine-4-carboxylic acid ethyl ester

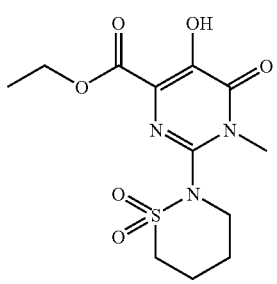

A solution of 2-(1,1-dioxo-1λ$^6$-[1,2]thiazinan-2-yl)-5-benzyloxy-1-methyl-6-oxo-1,6-dihydro-pyrimidine-4-carboxylic acid ethyl ester (4.05 g, 9.61 mmol) in a mixture of ethanol (250 ml) and ethyl acetate (250 ml) was hydrogenated over 10% palladium on activated carbon (0.9 g) and under 1 atmosphere of hydrogen for 1 h. The catalyst was then filtered and the solvent was evaporated under reduced pressure. Recrystallization of the residue from ethyl acetate gave 2.63 g (82% yield) of the title ester as white crystals; mp 186–189° C. $^1$HNMR 400 MHz (CDCl$_3$) δ (ppm): 1.42 (3H, t, J=7.0 Hz, CH$_3$), 1.6–1.63 (1H, m, CH), 2.3–2.6 (3H, m, CH$_2$ and CH), 3.2 (1H, m, CH), 3.55–3.75 (2H, m, CH$_2$), 3.65 (3H, s, NCH$_3$), 3.95–4.05 (1H, m, CH), 4.44 (2H, q, J=7.0 Hz, OCH$_2$). HRMS (FAB POS) calculated for C$_{12}$H$_{18}$N$_3$O$_6$S [M+H$^+$]: 332.091632. found: 332.092342.

Compound 1

N-[(4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide

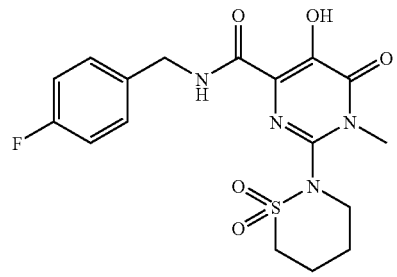

A mixture of 2-(1,1-dioxo-1λ$^6$-[1,2]thiazinan-2-yl)-5-hydroxy-1-methyl-6-oxo-1,6-dihydro-pyrimidine-4-carboxylic acid ethyl ester (1.00 g, 3.02 mmol) and 4-fluorobenzylamine (1.31 g, 10.5 mmol) in a mixture of anhydrous ethyl alcohol (40 ml) and N,N-dimethylformamide (10 ml) was heated under reflux for 10 h. The solvent was then evaporated in vacuo and the residue was diluted with dichloromethane (500 ml). The organic phase was washed with 5% aqueous acetic acid, brine and dried over anhydrous sodium sulfate. Evaporation of the solvent and recrystallization of the white solid obtained from dichloromethane and ethanol gave 1.04 g (84% yield) of the title amide as white crystals; mp 227–228° C. $^1$HNMR 400 MHz (CDCl$_3$) δ (ppm): 1.75 and 2.07 (2×1H, m, CH$_2$), 2.28–2.43 (2H, m, CH$_2$), 3.19–3.31 (2H, m, CH$_2$), 3.64 (3H, s, NCH$_3$), 3.6–3.8 (2H, m, CH$_2$), 4.59 (2H, AB part of ABX system, J$_{AB}$=14.9 Hz, Δv=36.1 Hz, J$_{AX}$=6.6 Hz, J$_{BX}$=5.8 Hz, NCH$_2$), 7.06 (2H, m, aromatics), 7.31 (2H, m, aromatics), 7.52 (1H, broad NH). Anal. Calcd for C$_{17}$H$_{19}$FN$_4$O$_5$S: C 49.75, H 4.67, N 13.65. Found: C 49.67, H 4.63, N 13.77.

Example 2

Compound 2A 2-(1,1-Dioxo-1λ$^6$-[1,2]thiazinan-2-yl)-5-methoxy-1-methyl-6-oxo-1,6-dihydro-pyrimidine-4-carboxylic acid 3,4-dichloro-benzylamide

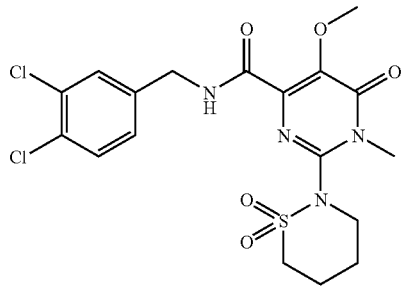

Reaction of 2-(1,1-dioxo-1λ$^6$-[1,2]thiazinan-2-yl)-5-methoxy-1-methyl-6-oxo-1,6-dihydro-pyrimidine-4-carboxylic acid (0.130 g, 0.41 mmol) and 3,4-dichlorobenzylamine (0.105 g, 0.60 mmol) in acetonitrile (10 ml) with triethylamine (0.16 ml, 1.14 mmol) and benzotriazole-1-yloxy-tris-pyrrolidino-phosphonium hexafluorophosphate (0.23 g, 0.44 mmol) 0.195 g (100% yield) of the title amide as a white solid; mp 212° C. (dec.). $^1$HNMR 400 MHz (DMSO-d$_6$) δ (ppm): 1.55–1.6 and 2.1–2.25 (1H and 3H, 2 m, 2×CH$_2$), 3.4–3.5 (2H, m, CH$_2$), 3.46 (3 H, s, NCH$_3$), 3.75–3.85 (2H, m, CH$_2$), 3.84 (3H, s, OCH$_3$), 4.46 (2H, d, J=6.0 Hz, NCH$_2$), 7.32 (1H, dd, J=2.0 Hz and J=8.3 Hz, aromatic), 7.56 (1H, d. J=2.0 Hz, aromatic), 7.63 (1H, d. J=8.3 Hz, aromatic), 9.03 (1H, broad t, NH). HRMS (FAB POS) calculated for C$_{18}$H$_{21}$Cl$_2$N$_4$O$_5$S [M+H$^+$]: 475.060972. found: 475.060157, δ 1.7 ppm.

Compound 2

N-[(3,4-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide

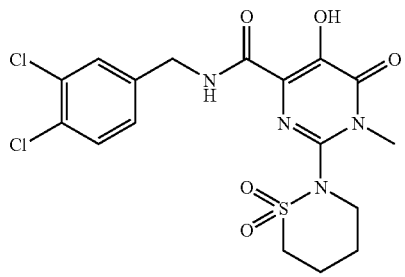

Reaction of 2-(1,1-dioxo-1λ$^6$-[1,2]thiazinan-2-yl)-5-methoxy-1-methyl-6-oxo-1,6-dihydro-pyrimidine-4-carboxylic acid 3,4-dichloro-benzylamide (0.160 g, 0.337 mmol) in 2,4,6-collidine with lithium iodide gave 0.118 g (76% yield) of the title amide as a white solid. $^1$HNMR 400 MHz (CDCl$_3$) δ (ppm): 1.70–1.85 and 2.06–2.15 (2×1H, 2 m, CH$_2$), 2.3–2.4 (2H, m, CH$_2$), 3.2–3.33 (2H, m, CH$_2$), 3.64 (3H, s, NCH$_3$), 3.7–3.85 (2H, m, CH$_2$), 4.58 (2H, AB part of ABX system, J$_{AB}$=15.5 Hz, Δν=49.6 Hz, J$_{AX}$=6.6 Hz, J$_{BX}$=6.1 Hz, NCH$_2$), 7.18 (1H, broad dd, aromatic), 7.42 (1H, broad d, aromatic), 7.45 (1H, d, J=8.1 Hz, aromatic, 7.57 (1H, broad NH). HRMS (FAB POS) calculated for C$_{17}$H$_{19}$Cl$_2$N$_4$O$_5$S [M+H$^+$]: 461.045322. found: 461.045599.

Example 3

Preparation of compounds 3–49

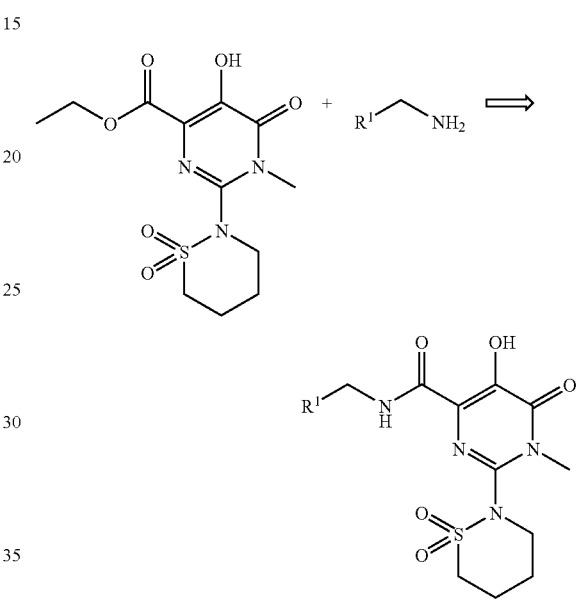

A solution of 2-(1,1-dioxo-1λ$^6$-[1,2]thiazinan-2-yl)-5-hydroxy-1-methyl-6-oxo-1,6-dihydro-pyrimidine-4-carboxylic acid ethyl ester (0.045 mmol) and the selected amine (0.180 mmol) in a mixture of anhydrous ethyl alcohol (0.5 ml) and N,N-dimethylformamide (0.5 ml) was heated in a sealed vial at 85° C. for 8 h. Acetic acid (1 ml) was added and the products were purified on a Shimadzu automated preparative HPLC system (column YMC Pack C-18, 5 μ, 20×100 mm, elution water 0.1% trifluoroacetic acid—acetonitrile). Spectrometry (MS) data were determined with a Micromass ZMD Platform TSQ 7000 LC/MS in positive electrospray mode.

The collected compounds were analysed using the following LC/MS conditions.

| Column: | Premisphere 5μ C-8, 4.6 × 30 mm |
|---|---|
| Solvent A: | 10% CH$_3$CN-90% H$_2$O, 0.05% TFA |
| Solvent B: | 90% CH$_3$CN-10% H$_2$O, 0.05% TFA |
| Gradient: | 100% A/0% B to 0% A/100% B |
| Gradient time: | 2 minutes, hold time 1 minute |
| Flow rate: | 4 ml/min. |
| Detector wavelength: | 220 nm. |

| Compound | R¹ | HPLC Retention time (min) | Formula | MS Data (M+H)⁺ |
|---|---|---|---|---|
| 3 | 3-F-phenyl | 1.71 | $C_{17}H_{19}FN_4O_5S$ | 411 |
| 4 | 4-Cl-phenyl | 1.72 | $C_{17}H_{19}ClN_4O_5S$ | 427 |
| 5 | 3-Cl-phenyl | 1.71 | $C_{17}H_{19}ClN_4O_5S$ | 427 |
| 6 | 4-F-phenethyl | 1.76 | $C_{19}H_{23}FN_4O_5S$ | 439 |
| 7 | 3,4-diCl-phenethyl | 1.93 | $C_{19}H_{22}Cl_2N_4O_5S$ | 489 |
| 8 | 4-CH₃-phenyl | 1.68 | $C_{18}H_{22}N_4O_5S$ | 407 |
| 9 | 3-CH₃-phenyl | 1.69 | $C_{18}H_{22}N_4O_5S$ | 407 |
| 10 | 4-OCH₃-phenyl | 1.57 | $C_{18}H_{22}N_4O_6S$ | 423 |
| 11 | 3-OCH₃-phenyl | 1.58 | $C_{18}H_{22}N_4O_6S$ | 423 |
| 12 | 3,5-diCl-phenyl | 1.84 | $C_{17}H_{18}Cl_2N_4O_5S$ | 461 |
| 13 | 3-CH₃-4-F-phenyl | 1.71 | $C_{18}H_{21}FN_4O_5S$ | 425 |
| 14 | 3-F-4-CH₃-phenyl | 1.72 | $C_{18}H_{21}FN_4O_5S$ | 425 |
| 15 | 3,4-diF-phenyl | 1.66 | $C_{17}H_{18}F_2N_4O_5S$ | 429 |
| 16 | 4-F-benzyl | 1.67 | $C_{18}H_{21}FN_4O_5S$ | 425 |
| 17 | 2,4-diF-phenyl | 1.65 | $C_{17}H_{18}F_2N_4O_5S$ | 429 |
| 18 | 3-Cl-4-F-phenyl | 1.74 | $C_{17}H_{18}ClFN_4O_5S$ | 445 |
| 19 | 3,4-diCH₃-phenyl | 1.76 | $C_{19}H_{24}N_4O_5S$ | 421 |
| 20 | 3-CF₃-4-F-phenyl | 1.80 | $C_{18}H_{18}F_4N_4O_5S$ | 479 |

-continued

[Structure: R¹-CH₂-NH-C(=O)- pyrimidine core with OH, =O, N-methyl, and N-linked thiazinane 1,1-dioxide]

| Compound | R¹ | HPLC Retention time (min) | Formula | MS Data (M+H)⁺ |
|---|---|---|---|---|
| 21 | 3-fluorophenyl | 1.74 | $C_{18}H_{21}FN_4O_5S$ | 425 |
| 22 | 2,4-dimethoxyphenyl | 1.62 | $C_{19}H_{24}N_4O_7S$ | 453 |
| 23 | 5-methylfuran-2-yl | 1.55 | $C_{16}H_{20}N_4O_6S$ | 397 |
| 24 | 2-methoxyphenyl | 1.63 | $C_{18}H_{22}N_4O_6S$ | 423 |
| 25 | diphenylmethyl | 1.89 | $C_{24}H_{26}N_4O_5S$ | 483 |
| 26 | 4-chlorophenyl | 1.77 | $C_{18}H_{21}ClN_4O_5S$ | 441 |
| 27 | 4-methoxyphenyl-CH₂ | 1.62 | $C_{19}H_{24}N_4O_6S$ | 437 |
| 28 | 2-fluorophenyl | 1.61 | $C_{17}H_{19}FN_4O_5S$ | 411 |
| 29 | 3-trifluoromethylphenyl | 1.78 | $C_{18}H_{19}F_3N_4O_5S$ | 461 |
| 30 | 3-chlorobenzyl | 1.76 | $C_{18}H_{21}ClN_4O_5S$ | 441 |
| 31 | benzyl | 1.65 | $C_{18}H_{22}N_4O_5S$ | 407 |
| 32 | 4-trifluoromethylphenyl | 1.80 | $C_{18}H_{19}F_3N_4O_5S$ | 461 |
| 33 | furan-2-yl | 1.44 | $C_{15}H_{18}N_4O_6S$ | 383 |
| 34 | thiophen-2-yl | 1.54 | $C_{15}H_{18}N_4O_5S_2$ | 399 |
| 35 | phenyl | 1.58 | $C_{17}H_{20}N_4O_5S$ | 393 |
| 36 | 2-chlorophenyl | 1.70 | $C_{17}H_{19}ClN_4O_5S$ | 427 |
| 37 | 2-methylphenyl | 1.66 | $C_{18}H_{22}N_4O_5S$ | 407 |
| 38 | 2-methoxybenzyl | 1.68 | $C_{19}H_{24}N_4O_6S$ | 437 |

| Compound | R¹ | HPLC Retention time (min) | Formula | MS Data (M + H)⁺ |
|---|---|---|---|---|
| 39 | 3-H₃CO-C₆H₄-CH₂-* | 1.64 | $C_{19}H_{24}N_4O_6S$ | 437 |
| 40 | 4-H₃C-C₆H₄-CH₂-* | 1.74 | $C_{19}H_{24}N_4O_5S$ | 421 |
| 41 | 3,4,5-(H₃CO)₃-C₆H₂-* | 1.47 | $C_{20}H_{26}N_4O_8S$ | 483 |
| 42 | 2,5-Cl₂-C₆H₃-* | 1.80 | $C_{17}H_{18}Cl_2N_4O_5S$ | 461 |
| 43 | 2,4-Cl₂-C₆H₃-* | 1.84 | $C_{17}H_{18}Cl_2N_4O_5S$ | 461 |
| 44 | 3,5-(CF₃)₂-C₆H₃-* | 1.95 | $C_{19}H_{18}F_6N_4O_5S$ | 529 |
| 45 | 2,5-F₂-C₆H₃-* | 1.64 | $C_{17}H_{18}F_2N_4O_5S$ | 429 |
| 46 | 2-CF₃-C₆H₄-* | 1.78 | $C_{18}H_{19}F_3N_4O_5S$ | 461 |
| 47 | 3,5-F₂-C₆H₃-* | 1.67 | $C_{17}H_{18}F_2N_4O_5S$ | 429 |
| 48 | 3-F₃CO-C₆H₄-* | 1.81 | $C_{18}H_{19}F_3N_4O_6S$ | 477 |
| 49 | 1H-indol-3-yl-CH₂-* | 1.64 | $C_{20}H_{23}N_5O_5S$ | 446 |

Example 4

Compound 50A

5-Benzyloxy-2-(1,1-dioxo-1$\lambda^6$-[1,2]thiazinan-2-yl)-1-methyl-6-oxo-1,6-dihydro-pyrimidine-4-carboxylic acid

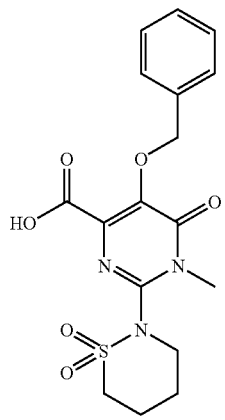

A solution of 5-benzyloxy-2-(1,1-dioxo-1$\lambda^6$-[1,2]thiazinan-2-yl)-1-methyl-6-oxo-1,6-dihydro-pyrimidine-4-carboxylic acid ethyl ester (1.02 g, 2.42 mmol) in 90% ethanol (30 ml) was treated with 1 N aqueous sodium hydroxide (5 ml) and stirred at 25° C. for 2 h. The ethanol was then evaporated in vacuo, the residue was acidified with 1 N hydrochloric acid (8 ml) and extracted with ethyl acetate. The organic phase was washed with brine, dried over anhydrous sodium sulfate and concentrated. Recrystallization of the solid residue from ethyl acetate gave 0.89 g (93% yield) of the title ester as a white crystals; mp 161–163° C. $^1$HNMR 400 MHz (CDCl$_3$) δ (ppm): 1.65 (1H, m, CH), 2.3–2.6 (3H, m, CH$_2$ and CH), 3.18–3.24 (1H, m, CH), 3.47–3.55 (1H, m, CH), 3.66 (3H, s, NCH$_3$), 3.6–3.7 (1H, m overlapping with NCH$_3$, CH), 3.96–4.03 (1H, m, CH), 5.56 (2H, AB system, J$_{AB}$=10.8 Hz, Δν=59.4 Hz, OCH$_2$), 7.35–7.5 (5H, m, aromatics). Anal. Calcd for C$_{17}$H$_{19}$N$_3$O$_6$S: C, 51.90; H, 4.86; N, 10.68. Found: C 51.76; H, 4.66; N, 10.69.

Compound 50B

5-Benzyloxy-2-(1,1-dioxo-1λ$^6$-[1,2]thiazinan-2-yl)-1-methyl-6-oxo-1,6-dihydro-pyrimidine-4-carboxylic acid (4-fluoro-phenyl)-amide

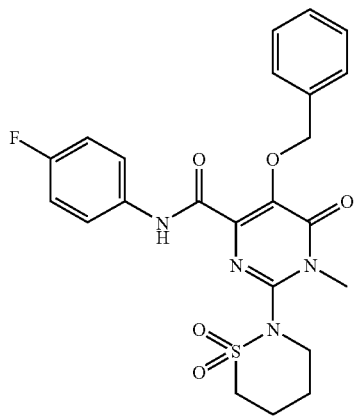

A solution of 5-benzyloxy-2-(1,1-dioxo-1λ$^6$-[1,2]thiazinan-2-yl)-1-methyl-6-oxo-1,6-dihydro-pyrimidine-4-carboxylic acid (0.200 g, 0.51 mmol) in dichloromethane (20 ml) was treated at 25° C. with (chloromethylene)dimethylammonium chloride (0.080 g, 0.62 mmol) and the resulting mixture was stirred for 15 min. Then a solution of 4-fluoroaniline (0.117 g, 1.06 mmol) and pyridine (0.1 ml, 1.2 mmol) in dichloromethane (2 ml) was added and the reaction mixture was stirred for another 45 min. The mixture was quenched by addition of ethyl acetate and pH 6 phosphate buffer. The organic phase was then washed with saturated sodium bicarbonate, brine and dried over anhydrous magnesium sulfate. Evaporation of the solvent and chromatography of the residue on silica gel (elution toluene-ethyl acetate 7:3) gave 0.270 g (88% yield) of the title amide as white crystals; mp 201–202° C.(ethyl acetate). $^1$HNMR 400 MHz (CDCl$_3$) δ (ppm): 1.65–1.69 and 2.35–2.7 (1H and 3H, 2 m, 2×CH$_2$), 3.2–3.25 (1H, m, CH), 3.59–3.73 (2H, m, CH$_2$), 3.68 (3H, s, NCH$_3$), 3.99–4.07 (1H, m, CH), 5.47 (2H, AB system, J$_{AB}$=10.8 Hz, Δν=49.8 Hz, OCH$_2$), 6.93 (2H, m, aromatics), 7.22 (2H, m, aromatics), 7.39–7.52 (5H, m, aromatics) Anal. Calcd for C$_{23}$H$_{23}$FN$_4$O$_5$S: C, 56.78; H, 4.77; N, 11.52. Found: C, 56.83; H, 4.58; N, 11.53.

Compound 50

2-(1,1-Dioxo-1λ$^6$-[1,2]thiazinan-2-yl)-5-hydroxy-1-methyl-6-oxo-1,6-dihydro-pyrimidine-4-carboxylic acid (4-fluoro-phenyl)-amide

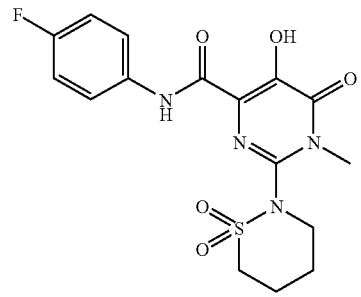

Hydrogenolysis of 5-benzyloxy-2-(1,1-dioxo-1λ$^6$-[1,2]thiazinan-2-yl)-1-methyl-6-oxo-1,6-dihydro-pyrimidine-4-carboxylic acid (4-fluoro-phenyl)-amide (0.177 g, 0.364 mmol) gave 0.111 g (77% yield) of the title amide as a white solid; mp 285–291° C. (dec.). $^1$HNMR 400 MHz (CDCl$_3$) δ (ppm): 1.83–1.92 and 2.14–2.25 (2×1H, 2 m, CH$_2$), 2.4–2.5 (2H, m, CH$_2$), 3.26–3.4 (2H, m, CH$_2$) 3.67 (3H, s, NCH$_3$), 3.7–3.9 (2H, m, CH$_2$), 7.11 (2H, m, aromatics), 7.58 (2H, m, aromatics), 9.0 (1H, broad s, NH). HRMS (FAB POS) calculated for C$_{16}$H$_{18}$FN$_4$O$_5$S [M+H$^+$]: 397.098195. found: 397.097570.

Example 4

Compound 51A

5-Benzyloxy-2-(1,1-dioxo-1λ$^6$-[1,2]thiazinan-2-yl)-1-methyl-6-oxo-1,6-dihydro-pyrimidine-4-carboxylic acid (1H-benzimidazol-2-ylmethyl)-amide

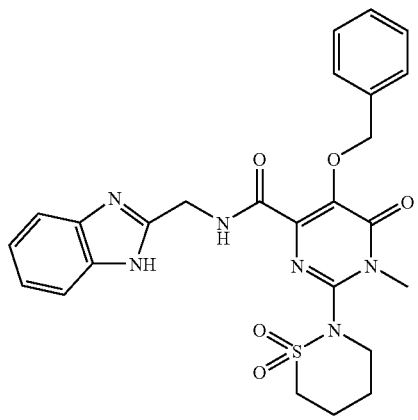

Coupling of 5-benzyloxy-2-(1,1-dioxo-1λ$^6$-[1,2]thiazinan-2-yl)-1-methyl-6-oxo-1,6-dihydro-pyrimidine-4-carboxylic acid (0.250 g, 0.63 mmol) with 2-(aminomethyl)benzimidazole dihydrochloride hydrate (0.30 g, 1.26 mmol) gave 0.090 g (27% yield) of the title amide as a white solid; mp 189–191° C. $^1$HNMR 400 MHz (CDCl$_3$) δ (ppm): 1.67 and 2.35–2.52 (1H and 3H, 2 m, 2×CH$_2$), 3.2–3.25 (1H, m, CH), 3.5–3.55 (1H, m, CH), 3.64 (3H, s, NCH$_3$), 3.69 (1H, m, CH), 3.94 (1H, m, CH), 4.67 (1H. d, J=6.0 Hz, NCH$_2$), 5.38 (2H, AB system, J$_{AB}$=11 Hz, Δν=48 Hz, OCH$_2$), 7.1–7.6 (9H, m, aromatics). HRMS (FAB POS) calculated for $C_{25}H_{27}N_6O_5S$ [M+H$^+$]: 523.176365. found: 523.176120, δ 0.5 ppm.

Compound 51

N-(1H-benzimidazol-2-ylmethyl)-1,6-dihydro-5-hydroxy-1-methyl-6-oxo-2-(tetrahydro-1,1-dioxido-2H-1,2-thiazin-2-yl)-4-pyrimidinecarboxamide

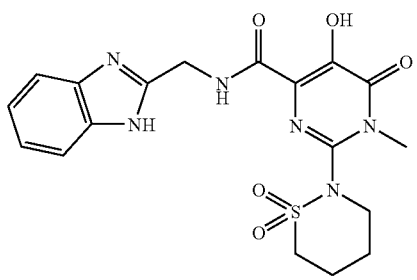

Hydrogenolysis of 5-benzyloxy-2-(1,1-dioxo-1λ$^6$-[1,2]thiazinan-2-yl)-1-methyl-6-oxo-1,6-dihydro-pyrimidine-4-carboxylic acid (1H-benzoimidazol-2-ylmethyl)-amide (0.078 g, 0.149 mmol) gave 0.030 g (46% yield) of the title amide as a white solid. $^1$HNMR 400 MHz (DMSO-d$_6$) δ (ppm): 1.56 and 2.15–2.19 (1H and 3H, 2 m, 2×CH$_2$), 3.41 (1H, m, CH), 3.45 (3H, s, NCH$_3$), 3.68 (1H, m, CH), 3.75 (2H, m, CH$_2$), 4.75 (2H, m, NCH$_2$), 7.15 (2H, m, aromatics), 7.51 (2H, m, aromatics). HRMS (FAB POS) calculated for $C_{18}H_{21}N_6O_5S$ [M+H$^+$]: 413.129415. found: 413.129071.

Example 5

Preparation of Compounds 52A–57

A Representative Procedure is Shown for Compound 52

Compound 52A

5-Benzyloxy-1-methyl-2-morpholin-4-yl-6-oxo-1,6-dihydro-pyrimidine-4-carboxylic acid ethyl ester

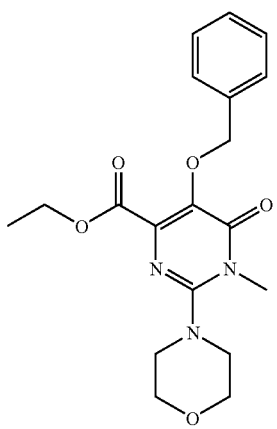

5-Benzyloxy-2-methanesulfonyl-1-methyl-6-oxo-1,6-dihydro-pyrimidine-4-carboxylic acid ethyl ester (0.215 g, 0.58 mmol) was reacted with morpholine as described in the preparation of compound 1J. Chromatography on silica gel (elution toluene-ethyl acetate 8:2 to 6:4) gave first 0.050 g (30% yield) of 5-benzyloxy-1-methyl-2,6-dioxo-1,2,3,6-tetrahydro-pyrimidine-4-carboxylic acid ethyl ester as white crystals; mp 184–187° C. (ethyl acetate). $^1$HNMR 400 MHz (CDCl$_3$) δ (ppm): 1.34 (3H, t, J=7.1 Hz, CH$_3$), 3.40 (3H, s, NCH$_3$), 4.39 (2H, q, J=7.1 Hz, OCH$_2$), 5.16 (3H, s, OCH$_2$), 7.35–7.5 (5H, m, aromatics), 8.12 (1H, broad s, NH). Anal. Calcd for $C_{15}H_{16}N_2O_5$: C, 59.20; H, 5.30; N, 9.20. Found: C, 59.20; H, 5.08, N 9.19 . The end fractions then gave 0.102 g (47% yield) of the title ester as a white syrup. $^1$HNMR 400 MHz (CDCl$_3$) δ (ppm): 1.29 (3H, t, J=7.1 Hz, CH$_3$), 3.20 (4H, m, NCH$_2$), 3.53 (3H, s, NCH$_3$), 3.82 (4H, m, OCH$_2$), 4.32 (2H, q, J=7.1 Hz, OCH$_2$), 5.17 (2H, s, OCH$_2$), 7.29–7.49 (5H, m, aromatics). HRMS (FAB POS) calculated for $C_{19}H_{24}N_3O_5$ [M+H$^+$]: 374.171596. found: 374.1709485

Compound 52B

5-Hydroxy-1-methyl-2-morpholin-4-yl-6-oxo-1,6-dihydro-pyrimidine-4-carboxylic acid ethyl ester

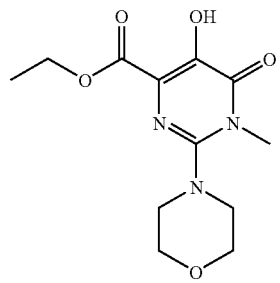

Hydrogenolysis of 5-benzyloxy-1-methyl-2-morpholin-4-yl-6-oxo-1,6-dihydro-pyrimidine-4-carboxylic acid ethyl ester (0.64 g, 1.71 mmol) gave 0.437 g (90% yield) of the title ester as white crystals; mp 175–176° C. (ethanol). $^1$HNMR 400 MHz (CDCl$_3$) δ (ppm): 1.43 (3H, t, J=7.1 Hz, CH$_3$), 3.13 (4H, m, NCH$_2$), 3.56 (3H, s, NCH$_3$), 3.83 (4H, m, OCH$_2$), 4.44 (2H, q, J=7.1 Hz, OCH$_2$), 10.32 (1H, s, OH). Anal. Calcd for $C_{12}H_{17}N_3O_5$: C 50.88; H, 6.04, N 14.83. Found: C, 50.79; H, 5.96, N 14.72.

Compound 52

N-[(4-fluorophenyl)methyl]-1,6-dihydro-5-hydroxy-1-methyl-2-(4-morpholinyl)-6-oxo-4-pyrimidinecarboxamide

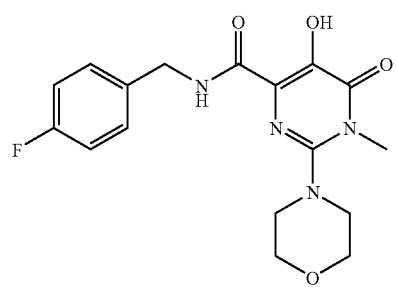

Reaction of 5-hydroxy-1-methyl-2-morpholin-4-yl-6-oxo-1,6-dihydro-pyrimidine-4-carboxylic acid ethyl ester (0.050 g, 0.176 mmol) with 4-fluorobenzylamine (0.07 g, 0.56 mmol) in ethyl alcohol (3 ml) gave 0.054 g (84% yield) of the title ester as white crystals; mp 197–199° C. (ethyl acetate). $^1$HNMR 400 MHz (CDCl$_3$) δ (ppm): 3.08 (4H, m, NCH$_2$), 3.58 (3H, s, NCH$_3$), 3.85 (4H, m, OCH$_2$), 4.61 (2H, d, J=6.0 Hz, NCH$_2$), 7.08 (2H, m, aromatics), 7.34 (2H, m, aromatics), 7.77 (1H, broad t, NH), 11.74 (1H, s, OH). Anal. Calcd for C$_{17}$H$_{19}$FN$_4$O$_4$: C 56.34; H, 5.28, N 15.46. Found: C, 56.39; H, 5.02, N 15.45.

Compound 53

N-[(3,4-dichlorophenyl)methyl]-1,6-dihydro-5-hydroxy-1-methyl-2-(4-morpholinyl)-6-oxo-4-pyrimidinecarboxamide

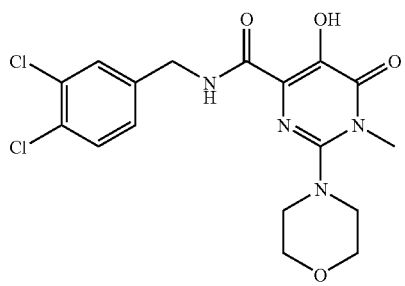

White crystals; mp 100–102° C. (ethyl acetate-hexane). $^1$HNMR 400 MHz (CDCl$_3$) δ (ppm): 3.07 (4H, m, NCH$_2$), 3.56 (3H, s, NCH$_3$), 3.83 (4H, m, OCH$_2$), 4.57 (2H, d, J=6.5 Hz, NCH$_2$), 7.18 (1H, dd, J=2.0 Hz and J=8.2 Hz, aromatic), 7.42 (1H, d, J=2.0 Hz, aromatic), 7.44 (1H, d, J=8.2 Hz, aromatic), 7.78 (1H, broad t, NH). HRMS (FAB POS) calculated for C$_{17}$H$_{19}$Cl$_2$N$_4$O$_4$ [M+H$^+$]: 413.078336. found: 413.076964.

Compound 54

N-[(4-fluoro-3-methylphenyl)methyl]-1,6-dihydro-5-hydroxy-1-methyl-2-(4-morpholinyl)-6-oxo-4-pyrimidinecarboxamide

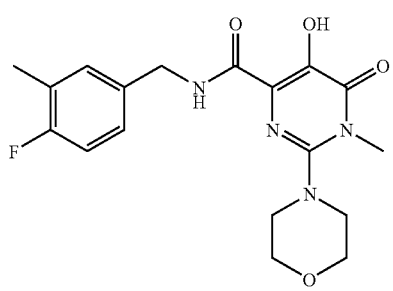

White crystals; mp 182–185° C. (ethyl acetate-hexane). $^1$HNMR 400 MHz (CDCl$_3$) δ (ppm): 2.28 (3H, d, J=2.0 Hz, CH$_3$), 3.05 (4H, m, NCH$_2$), 3.55 (3H, s, NCH$_3$), 3.82 (4H, m, OCH$_2$), 4.54 (2H, d, J=6.3 Hz, NCH$_2$), 6.99 (1H, m, aromatic), 7.1–7.16 (2H, m, aromatics), 7.72 (1H, broad t, NH). Anal. Calcd for C$_{18}$H$_{21}$FN$_4$O$_4$: C 57.44; H, 5.62, N 14.89. Found: C, 57.31; H, 5.46, N 14.79.

Compound 55

N-[(3-fluoro-4-methylphenyl)methyl]-1,6-dihydro-5-hydroxy-1-methyl-2-(4-morpholinyl)-6-oxo-4-pyrimidinecarboxamide

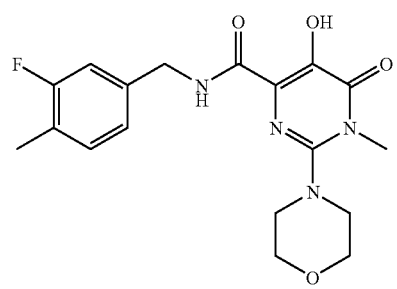

White crystals; mp 166–167° C. (ethyl acetate-hexane). $^1$HNMR 400 MHz (CDCl$_3$) δ (ppm): 2.27 (3H, d, J=1.8 Hz, CH$_3$), 3.06 (4H, m, NCH$_2$), 3.56 (3H, s, NCH$_3$), 3.83 (4H, m, OCH$_2$), 4.57 (2H, d, J=6.3 Hz, NCH$_2$), 6.99 (2H, m, aromatics), 7.17 (1H, m, aromatic), 7.75 (1H, broad t, NH). Anal. Calcd for C$_{18}$H$_{21}$FN$_4$O$_4$: C 57.44; H, 5.62, N 14.89. Found: C, 57.29; H, 5.62, N 14.82.

Compound 56

N-[(3-chloro-4-fluorophenyl)methyl]-1,6-dihydro-5-hydroxy-1-methyl-2-(4-morpholinyl)-6-oxo-4-pyrimidinecarboxamide

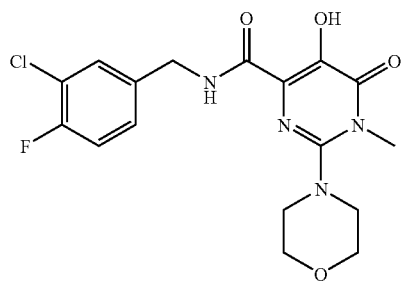

White crystals; mp 170–171° C. (ethyl acetate-hexane). $^1$HNMR 400 MHz (CDCl$_3$) δ (ppm): 3.07 (4H, m, NCH$_2$), 3.56 (3H, s, NCH$_3$), 3.83 (4H, m, OCH$_2$), 4.57 (2H, d, J=6.2

Hz, NCH$_2$), 7.13 (1H, m, aromatic), 7.22 (1H, m, aromatic), 7.37 (1H,dd, J=2.0 Hz and J=7.0 Hz, aromatic),7.78 (1H, broad t, NH). Anal. Calcd for C$_{17}$H$_{18}$ClFN$_4$O$_4$:C 51.45; H, 4.57, N 14.12. Found: C, 51.50; H 4.09, N 14.01. HRMS (FAB POS) calculated for C$_{17}$H$_{19}$ClFN$_4$O$_4$ [M+H $^+$]: 397.107866. found: 397.109213.

Compound 57

N-[(3,4-dimethylphenyl)methyl]-1,6-dihydro-5-hydroxy-1-methyl-2-(4-morpholinyl)-6-oxo-4-pyrimidinecarboxamide

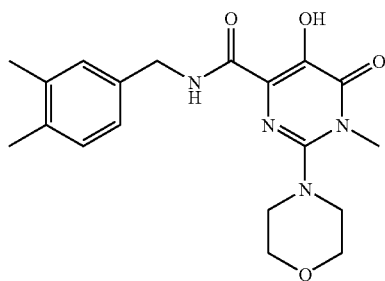

White crystals; mp 164–166° C. (ethyl acetate-hexane). $^1$HNMR 400 MHz (CDCl$_3$) δ (ppm): 2.26 (3H, s, CH$_3$), 2.27 (3H, s, CH$_3$), 3.04 (4H, m, NCH$_2$), 3.55 (3H, s, NCH$_3$), 3.82 (4H, m, OCH$_2$), 4.55 (2H, d, J=6.0 Hz, NCH$_2$), 7.06–7.24 (3H, m, aromatics), 7.72 (1H, broad t, NH). Anal. Calcd for C$_{19}$H$_{24}$N$_4$O$_4$: C 61.27; H, 6.49, N 15.04. Found: C, 61.07; H, 6.83, N 14.92.

Example 6

Preparation of Compounds 58A–62

A representative Procedure is Shown for Compound 58

Compounds 58A and 58B

5-Benzyloxy-1-methyl-2-(3-methyl-[1,2,4]triazol-1-yl)-6-oxo-1,6-dihydro-pyrimidine-4-carboxylic acid ethyl ester (58A) and 5-Benzyloxy-1-methyl-2-(5-methyl-[1,2,4]triazol-1-yl)-6-oxo-1,6-dihydro-pyrimidine-4-carboxylic acid ethyl ester (58B)

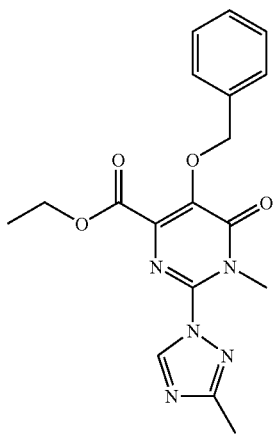

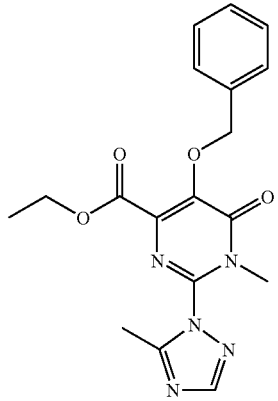

A solution of 5-benzyloxy-2-methanesulfonyl-1-methyl-6-oxo-1,6-dihydro-pyrimidine-4-carboxylic acid ethyl ester (1.00 g, 2.73 mmol) and 3-methyl-1H-[1,2,4]triazole (0.272 g, 3.27 mmol) in dry N,N-dimethylformamide (10 ml) at 0° C. was treated with sodium hydride (0.16 g of a 60% dispersion in mineral oil, 4.0 mmol) and the resulting mixture was stirred at 0° C. for 30 min and at 24° C. for another 30 min. The reaction mixture was then quenched with acetic acid (0.2 ml) and the solvent was evaporated in vacuo. The residue was dissolved in ethyl acetate, washed with saturated sodium bicarbonate, brine and dried over anhydrous magnesium sulfate. Evaporation of the solvent and chromatography on silica gel (elution toluene-acetone 90:10 to 85:15) first gave 0.358 g (35% yield) of 5-benzyloxy-1-methyl-2-(3-methyl-[1,2,4]triazol-1-yl)-6-oxo-1,6-dihydro-pyrimidine-4-carboxylic acid ethyl ester as a clear oil. $^1$HNMR 400 MHz (CDCl$_3$) δ (ppm): 1.34 (3H, t, J=7.1 Hz, CH$_3$), 2.51 (3H, s, CH$_3$), 3.73 (3H, s, NCH$_3$), 4.37 (2H, q, J=7.1 Hz, CH$_2$), 5.37 (2H, s, OCH$_2$), 7.40 (3H, m, aromatics), 7.50 (2H, m, aromatics), 8.71 (1H, s, CH). HRMS (FAB POS) calculated for C$_{18}$H$_{20}$N$_5$O$_4$ [M+H$^+$]: 370.14. found: 370.14. The following fractions then gave 0.395 g (39% yield) of 5-benzyloxy-1-methyl-2-(5-methyl-[1,2,4]triazol-1-yl)-6-oxo-1,6-dihydro-pyrimidine-4-carboxylic acid ethyl ester as a white solid. $^1$HNMR 400 MHz (CDCl$_3$) δ (ppm): 1.33 (3H, t, J=7.0 Hz, CH$_3$), 2.67 (3H, s, CH$_3$), 3.52 (3H, s, NCH$_3$), 4.37 (2H, q, J=7.0 Hz, CH$_2$), 5.41 (2H, s, OCH$_2$), 7.40 (3H, m, aromatics), 7.51 (2H, m, aromatics), 8.00 (1H, s, CH). HRMS (FAB POS) calculated for C$_{18}$H$_{20}$N$_5$O$_4$ [M+H$^+$]: 370.14. found: 370.14.

Compound 58C

5-Hydroxy-1-methyl-2-(3-methyl-[1,2,4]triazol-1-yl)-6-oxo-1,6-dihydro-pyrimidine-4-carboxylic acid ethyl ester

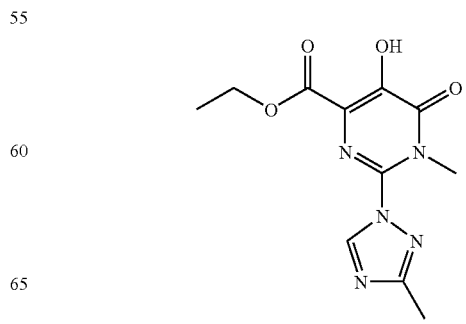

Hydrogenolysis of 5-benzyloxy-1-methyl-2-(3-methyl-[1,2,4]triazol-1-yl)-6-oxo-1,6-dihydro-pyrimidine-4-carboxylic acid ethyl ester (0.445 g, 1.20 mmol) in ethyl acetate) gave 0.286 g (85% yield) of the title ester as white crystals; mp 160–162° C. $^1$HNMR 400 MHz (CDCl$_3$) δ (ppm): 1.46 (3H, t, J=7.1 Hz, CH$_3$), 2.51 (3H, s, CH$_3$), 3.68 (3H, s, NCH$_3$), 4.52 (2H, q, J=7.1 Hz, CH$_2$), 8.63 (1H, s, CH), 10.91 (1H, s, OH). HRMS (FAB POS) calculated for $C_{11}H_{14}N_5O_4$ [M+H$^+$]: 280.10. found: 280.10.

Compound 58

N-[(4-fluorophenyl)methyl]-1,6-dihydro-5-hydroxy-1-methyl-2-(3-methyl-1H-1,2,4-triazol-1-yl)-6-oxo-4-pyrimidinecarboxamide

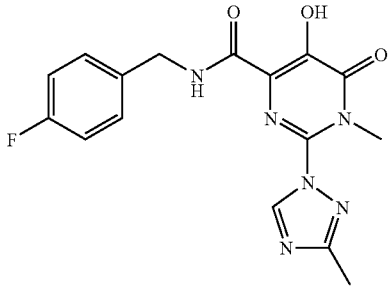

Reaction of 5-hydroxy-1-methyl-2-(3-methyl-[1,2,4]triazol-1-yl)-6-oxo-1,6-dihydro-pyrimidine-4-carboxylic acid ethyl ester (0.060 g, 0.21 mmol) with 4-fluorobenzylamine (0.16 g, 1.28 mmol) gave 0.037 g (49% yield) of the title ester as white crystals. $^1$HNMR 400 MHz (CDCl$_3$) δ (ppm): 2.51 (3H, s, CH$_3$), 3.63 (3H, s, NCH$_3$), 4.60 (2H, d, J=6.2 Hz, NCH$_2$), 7.07 (2H, m, aromatics), 7.33 (2H, m, aromatics), 7.60 (1H, broad t, NH), 8.50 (1H, s, CH), 12.45 (1H, s, OH). HRMS (FAB POS) calculated for $C_{16}H_{16}FN_6O_3$ [M+H$^+$]: 359.12. found: 359.12.

Compound 59

N-[(3,4-dichlorophenyl)methyl]-1,6-dihydro-5-hydroxy-1-methyl-2-(3-methyl-1H-1,2,4-triazol-1-yl)-6-oxo-4-pyrimidinecarboxamide

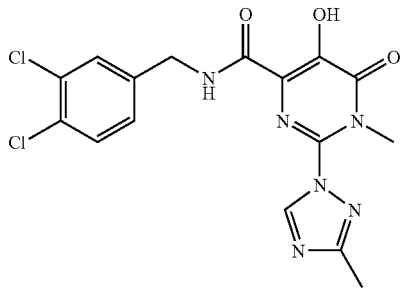

White crystals; mp 188–189° C. (dec.) (ethyl acetate-hexane). $^1$HNMR 400 MHz (CDCl$_3$) δ (ppm): 2.52 (3H, s, CH$_3$), 3.64 (3H, s, NCH$_3$), 4.59 (2H, d, J=6.3 Hz, NCH$_2$), 7.20 (1H, dd, J=2.0 Hz and J=8.7 Hz, aromatic), 7.43 (1H, d, J=2.0 Hz, aromatic), 7.46 (1H, dd, J=8.7 Hz, aromatic), 7.65 (1H, broad t, NH), 8.52 (1H, s, CH), 12.30 (1H, s, OH). HRMS (FAB POS) calculated for $C_{16}H_{15}Cl_2N_6O_3$ [M+H$^+$]: 409.05. found: 409.05.

Compound 60

N-[(4-fluoro-3-methylphenyl)methyl]-1,6-dihydro-5-hydroxy-1-methyl-2-(3-methyl-1H-1,2,4-triazol-1-yl)-6-oxo-4-pyrimidinecarboxamide

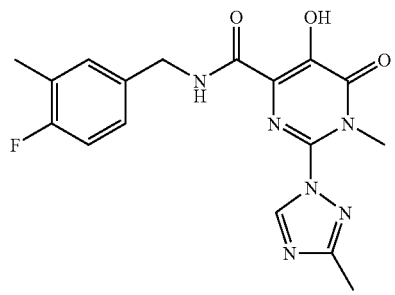

White crystals; mp 204–205° C. (ethyl acetate-hexane). $^1$HNMR 400 MHz (CDCl$_3$) δ (ppm): 2.29 (3H, d, J=1.9 Hz, CH$_3$), 2.51 (3H, s, CH$_3$), 3.63 (3H, s, NCH$_3$), 4.55 (2H, d, J=6.2 Hz, NCH$_2$), 7.0 (1H, m, aromatic), 7.1–7.16 (2H, m, aromatics), 7.57 (1H, broad t, NH), 8.50 (1H, s, CH), 12.48 (1H, s, OH). HRMS (FAB POS) calculated for $C_{17}H_{18}FN_6O_3$ [M+H$^+$]: 373.13. found: 373.13.

Compound 61

N-[(4-fluorophenyl)methyl]-1,6-dihydro-5-hydroxy-1-methyl-2-(5-methyl-1H-1,2,4-triazol-1-yl)-6-oxo-4-pyrimidinecarboxamide

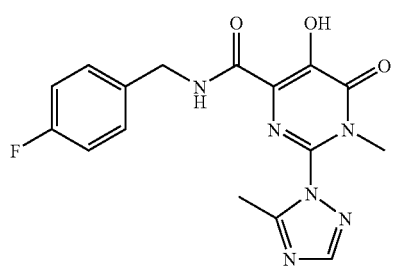

White crystals; mp 230° C. (ethyl acetate-ether). $^1$HNMR 400 MHz (CDCl$_3$) δ (ppm): 2.54 (3H, s, CH$_3$), 3.42 (3H, s, NCH$_3$), 4.59 (2H, d, J=6.2 Hz, NCH$_2$), 7.07 (2H, m, aromatics), 7.32 (2H, m, aromatics), 7.57 (1H, broad t, NH), 8.02 (1H, s, CH), 12.57 (1H, s, OH). HRMS (FAB POS) calculated for $C_{16}H_{16}FN_6O_3$ [M+H$^+$]: 359.126592. found: 359.125641.

Compound 62

N-[(3,4-dichlorophenyl)methyl]-1,6-dihydro-5-hydroxy-1-methyl-2-(5-methyl-1H-1,2,4-triazol-1-yl)-6-oxo-4-pyrimidinecarboxamide

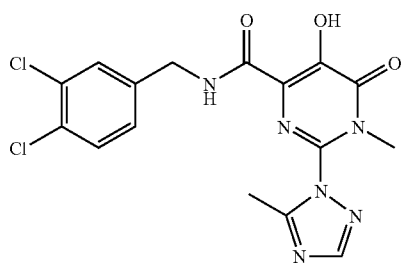

White crystals. $^1$HNMR 400 MHz (CDCl$_3$) δ (ppm): 2.56 (3H, s, CH$_3$), 3.42 (3H, s, NCH$_3$), 4.58 (2H, d, J=6.2 Hz, NCH$_2$), 7.18 (1H, dd, J=2.0 Hz and J=8.1 Hz, aromatic), 7.43 (1H, d, J=2.0 Hz, aromatic), 7.45 (1H, dd, J=8.1 Hz, aromatic), 7.64 (1H, broad t, NH), 8.03 (1H, s, CH), 12.42 (1H, s, OH). HRMS (FAB POS) calculated for C$_{16}$H$_{15}$Cl$_2$N$_6$O$_3$ [M+H$^+$]: 409.058269. found: 409.056702.

Example 7

Compound 63A

2-Amino-5-benzyloxy-1-methyl-6-oxo-1,6-dihydro-pyrimidine-4-carboxylic acid ethyl ester

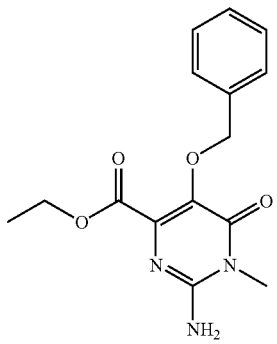

Gaseous ammonia was bubbled at 25° C. in a solution of 2-methanesulfonyl-5-benzyloxy-1-methyl-6-oxo-1,6-dihydro-pyrimidine-4-carboxylic acid ethyl ester (0.200 g, 0.55 mmol) in acetonitrile (4 ml). After 30 min, the solvent was evaporated in vacuo and the residue was chromatographed on silica gel (elution toluene-ethyl acetate, 6:4 to 1:1) to give 0.099 g (59% yield) of the title ester as a white solid. $^1$HNMR 400 MHz (DMSO-d$_6$) δ (ppm): 1.19 (3H, t, J=7.1 Hz, CH$_3$), 3.29 (3H, s, NCH$_3$), 4.18 (2H, q, J=7.1 Hz, OCH$_2$), 4.89 (2H, s, OCH$_2$), 7.21 (2H, broad s, NH$_2$), 7.31–7.37 (5H, m, aromatics). Anal. Calcd for C$_{15}$H$_{17}$N$_3$O$_4$: C 59.39; H, 5.64; N, 13.85. Found: C, 59.31; H, 5.46, N 13.72.

Compound 63B 2-amino-5-hydroxy-1-methyl-6-oxo-1,6-dihydro-pyrimidine-4-carboxylic acid ethyl ester

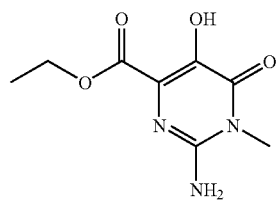

Hydrogenolysis of 2-amino-5-benzyloxy-1-methyl-6-oxo-1,6-dihydro-pyrimidine-4-carboxylic acid ethyl ester (0.069 g, 0.23 mmol) gave 0.049 g of the title ester as an amorphous solid which was used as such for the next step. MS (ESI$^+$) $^{m/z}$ 214 [M+H$^+$].

Compound 63

2-amino-5-hydroxy-1-methyl-6-oxo-1,6-dihydro-pyrimidine-4-carboxylic acid 4-fluorobenzylamine

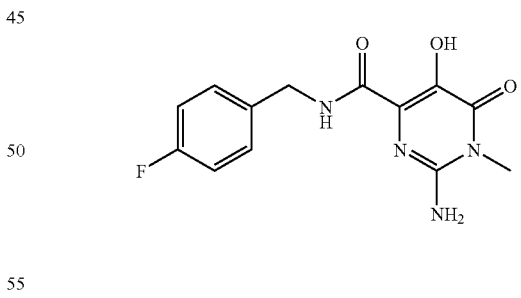

Reaction of 2-amino-5-hydroxy-1-methyl-6-oxo-1,6-dihydro-pyrimidine-4-carboxylic acid ethyl ester (0.049 g, 0.23 mmol) with 4-fluorobenzylamine (0.10 g, 0.81 mmol) gave 0.030 g (42% yield) of the title ester as a white solid. $^1$HNMR 400 MHz (DMSO-d$_6$) δ (ppm): 3.71 (3H, s, NCH$_3$), 4.45 (2H, d, J=6.2 Hz, NCH$_2$), 6.51 (2H, broad s, NH$_2$), 7.1–7.19 (2H, m, aromatics), 7.34–7.38 (2H, m, aromatics), 8.71 (1H, broad t, NH). HRMS (FAB POS) calculated for C$_{13}$H$_{14}$FN$_4$O$_3$ [M+H$^+$]: 293.104994. found: 293.104843.

Example 8

Compound 64A

5-Benzyloxy-1-methyl-2-methylamino-6-oxo-1,6-dihydro-pyrimidine-4-carboxylic acid ethyl ester

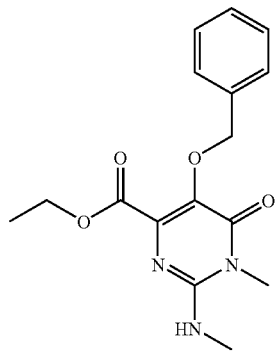

A solution of 2-methanesulfonyl-5-benzyloxy-1-methyl-6-oxo-1,6-dihydro-pyrimidine-4-carboxylic acid ethyl ester (1.180 g, 3.22 mmol) in acetonitrile (20 ml) was treated at 25° C. with N,N-diisopropylethylamine (1.5 ml, 0.87 mmol) followed by 4.8 ml (9.6 mmol) of a 2M solution of methylamine in tetrahydrofuran. After 30 min, the solvent was evaporated in vacuo and the residue was chromatographed on silica gel (elution toluene-ethyl acetate, 25:75) to give 0.838 g (82% yield) of the title ester as a clear syrup. $^1$HNMR 400 MHz (CDCl$_3$) δ (ppm): 1.30 (3H, t, J=7.1 Hz, CH$_3$), 3.04 (3H, d, J=5.1 Hz, NCH$_3$), 3.42 (3H, s, NCH$_3$), 4.32 (2H, q, J=7.1 Hz, OCH$_2$), 4.58 (1H, broad q, NH), 5.07 (2H, s, OCH$_2$), 7.3–7.37 (3H, m, aromatics), 7.47 (2H, m, aromatics). HRMS (FAB POS) calculated for C$_{16}$H$_{20}$N$_3$O$_4$ [M+H$^+$]: 318.145381. found: 318.144860.

Compound 64B

5-Hydroxy-1-methyl-2-methylamino-6-oxo-1,6-dihydro-pyrimidine-4-carboxylic acid ethyl ester

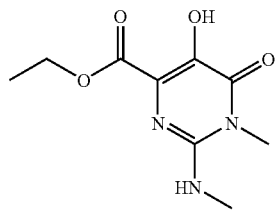

Hydrogenolysis of 5-benzyloxy-1-methyl-2-methylamino-6-oxo-1,6-dihydro-pyrimidine-4-carboxylic acid ethyl ester (0.200 g, 0.63 mmol) gave 0.106 g (74% yield) of the title ester as light yellow crystals; mp 226° C. (ethyl acetate). $^1$HNMR 400 MHz (DMSO-d$_6$+D$_2$O) δ (ppm): 1.26 (3H, t, J=7.1 Hz, CH$_3$), 2.75 (3H, s, NCH$_3$), 3.29 (3H, s, NCH$_3$), 4.26 (2H, q, J=7.1 Hz, OCH$_2$). HRMS (FAB POS) calculated for C$_9$H$_{14}$N$_3$O$_4$ [M+H$^+$]: 228.098431. found: 228.099099.

Compound 64

5-Hydroxy-1-methyl-2-methylamino-6-oxo-1,6-dihydro-pyrimidine-4-carboxylic acid 4-fluoro-benzylamine

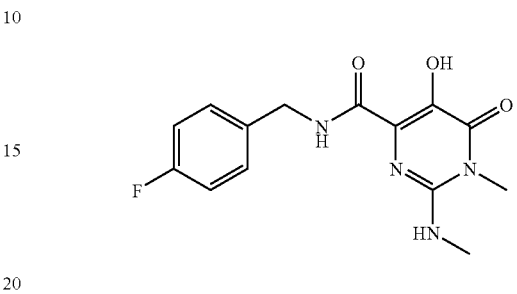

Reaction of 5-hydroxy-1-methyl-2-methylamino-6-oxo-1,6-dihydro-pyrimidine-4-carboxylic acid ethyl ester (0.071 g, 0.231 mmol) with 4-fluorobenzylamine (0.14 g, 1.12 mmol) gave 0.080 g (84% yield) of the title ester as a white solid. $^1$HNMR 400 MHz (DMSO-d$_6$+D$_2$O) δ (ppm): 2.86 (3H, s, NCH$_3$), 3.39 (3H, s, NCH$_3$), 4.46 (2H, d, J=6.1 Hz, NCH$_2$), 6.78 (1H exchanged D$_2$O, broad s, NH), 7.16 (2H, m, aromatics), 7.35 (2H, m, aromatics), 9.14 (1H, broad t, NH), 11.32 (1H exchanged D$_2$O, s, OH). HRMS (FAB POS) calculated for C$_{14}$H$_{16}$FN$_4$O$_3$ [M+H$^+$]: 307.120644. found: 307.119723.

Example 9

Preparation of Compounds 65A–66

Compound 65A

5-Benzyloxy-2-(4-hydroxypiperidine-1-yl)-1-methyl-6-oxo-1,6-dihydropyrimidine-4-carboxylic acid ethyl ester

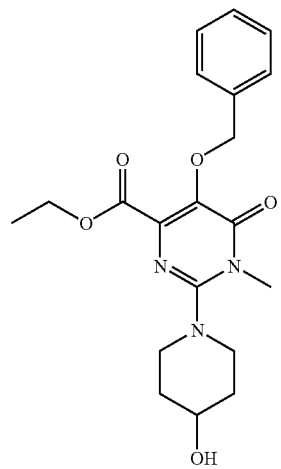

A solution of 5-Benzyloxy-2-methanesulfonyl-1-methyl-6-oxo-1,6-dihydro-pyrimidine-4-carboxylic acid ethyl ester (0.725 g, 2 mmol) and 4-hydroxypiperidine (1 g, 10 mmol) in THF (20 mL) was stirred for 16 h at ambient temperature. Then, the reaction mixture was taken up in EtOAC (100 mL), washed with 1N aq HCl (2×10 mL) and brine (10 mL). The organic phase was dried (Na$_2$SO$_4$), filtered and concentrated to give the desired product as a pale yellow paste (0.608 g, 79%) which was used in the subsequent reaction without further purification. $^1$H NMR (500 MHz, CDCl$_3$) δ: 7.46 (d, J=7.0 Hz, 2H), 7.36–7.28 (m, 3H), 5.14 (s, 2H), 4.30 (q, J=7.0 Hz, 2H), 3.92–3.87 (m, 1H), 3.50 (s, 3H), 3.44–3.39 (m, 2H), 3.01–2.95 (m, 2H), 2.79 (br s, 1H), 2.02–1.98 (m, 2H), 1.71–1.64 (m, 2H), 1.28 (t, J=7.0 Hz, 3H). LRMS (M+H) calcd for C$_{20}$H$_{26}$N$_3$O$_5$: 388.44. found: 388.20

Compound 65B

5-Hydroxy-1-methyl-6-oxo-2-[4-(2,2,2-trifluoroacetoxy)piperidin-1-yl]-1,6-dihydropyrimidine-4-carboxylic acid ethyl ester

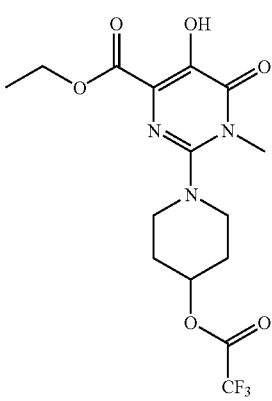

5-Benzyloxy-2-(4-hydroxypiperidin-1-yl)-1-methyl-6-oxo-1,6-dihydropyrimidine-4-carboxylic acid ethyl ester (0.760 g, 1.96 mmol) was treated with trifluroacetic acid (20 mL) at ambient temperature. After 10 h, the reaction mixture was concentrated and purified on silica gel column using 2–5% MeOH/CH2Cl2 to afford desired product as a brown paste (0.650 g, 84%). $^1$H NMR (500 MHz, CDCl$_3$) δ: 10.02 (br s, 1H), 5.23–5.19 (m, 1H), 4.44 (q, J=7.0 Hz, 2H), 3.57 (s, 3H), 3.36–3.31 (m, 2H), 3.15–3.10 (m, 2H), 2.17–2.11 (m, 2H), 2.02–1.95 (m, 2H), 1.42 (t, J=7.0 Hz, 3H). LRMS (M+H) calcd for C$_{15}$H$_{19}$F$_3$N$_3$O$_6$: 394.32. found: 394.09

Compound 65

N-[(4-fluorophenyl)methyl]-1,6-dihydro-5-hydroxy-2-(4-hydroxy-1-piperidinyl)-1-methyl-6-oxo-4-pyrimidinecarboxamide

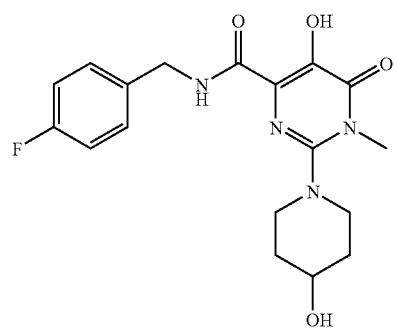

A solution of 4-fluorobenzylamine (156 mg, 1.25 mmol) and 5-hydroxy-1-methyl-6-oxo-2-[4-(2,2,2-trifluoroacetoxy)piperidin-1-yl]-1,6-dihydropyrimidine-4-carboxylic acid ethyl ester (100 mg, 0.254 mmol) in dimethylformamide (3 mL) was heated at 120° C. for 2 h. Then, cooled and purified by preparative HPLC using MeOH/Water containg 0.1% TFA as an eluent. The fractions containing the product were combined and concentrated to afford title compound as a off-white solid (46 mg, 48%). $^1$H NMR (500 MHz, CDCl$_3$) δ: 11.62 (s, 1H), 7.75 (br s, 1H), 7.31–7.28 (m, 2H), 7.04 (t, J=8.7 Hz, 2H), 4.56 (d, J=6.4 Hz, 2H), 3.95–3.89 (m, 1H), 3.52 (s, 3H), 3.28–3.23 (m, 2H), 2.88–2.83 (m, 2H), 2.02–1.96 (m, 2H), 1.73–1.66 (m, 2 H), 1.54 (br s, 1H). HRMS (M−H) calcd for C$_{18}$H$_{20}$FN$_4$O$_4$: 375.1469. found: 375.1472. Anal calcd for C$_{18}$H$_{21}$FN$_4$O$_4$: C, 57.44; H, 5.62; N, 14.88. Found: C, 57.19; H, 5.55; N, 14.82.

Compound 66

N-[(4-fluoro-3-methylphenyl)methyl]-1,6-dihydro-5-hydroxy-2-(4-hydroxy-1-piperidinyl)-1-methyl-6-oxo-4-pyrimidinecarboxamide

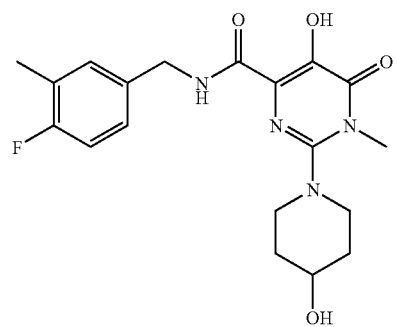

White solid. $^1$H NMR (500 MHz, CDCl$_3$) δ: 11.65 (s, 1H), 7.74 (br s, 1H), 7.14–7.09 (m, 2H), 6.97 (t, J=8.9 Hz, 1H), 4.52 (d, J=6.11 Hz, 1H), 3.95–3.89 (m, 1H), 3.52 (s, 3H), 3.28–3.22 (m, 2H), 2.89–2.84 (m, 2H), 2.27 (s, 3H), 2.02–1.96 (m, 2H), 1.73–1.66 (m, 2H), 1.52 (br s, 1H). HRMS (M–H) calcd for C$_{19}$H$_{22}$FN$_4$O$_4$: 389.1625. found: 389.1638. Anal calcd for C$_{19}$H$_{23}$FN$_4$O$_4$: C, 58.45; H, 5.93; N, 14.35. Found: C, 58.15; H, 5.84; N, 14.18.

Example 10

Preparation of Compounds 67A–82

A Representative Procedure is Shown for Compound 67

Compound 67A

5-Benzyloxy-2-[4-(2-hydroxy-ethyl)-piperazin-1-yl]-1-methyl-6-oxo-1,6-dihydro-pyrimidine-4-carboxylic acid ethyl ester

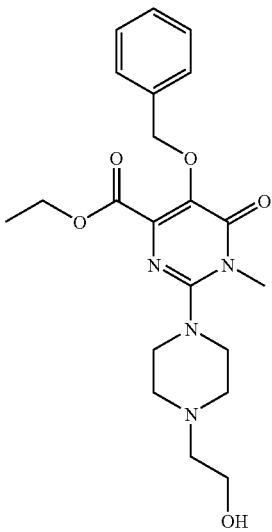

To a solution of 5-Benzyloxy-2-methanesulfonyl-1-methyl-6-oxo-1,6-dihydro-pyrimidine-4-carboxylic acid ethyl ester (0.10 g, 0.27 mmol) dissolved in THF (1 mL) was added 1-(2-hydroxyethyl)piperazine (0.05 mL, 0.41 mmol). The resulting mixture was stirred at 70° C. for 3 hours. The mixture was concentrated and the resulting residue was purified by flash chromatography, eluting with 2% MeOH/ CH$_2$Cl$_2$ to yield the title compound as a pale yellow oil (0.0423 g, 38% yield). $^1$H NMR (500 MHz, CDCl$_3$) δ: 7.45 (2H, d, J=7.0 Hz), 7.35–7.27 (3H, m), 5.14 (2H, s), 4.30 (2H, q, J=7.1 Hz), 3.63 (2H, t, J=5.3 Hz), 3.49 (3H, s), 3.21 (4H, t, J=4.7 Hz), 2.63 (4H, bs), 2.59 (2H, t, J=5.3 Hz), 1.27 (3H, t, J=7.2 Hz). HRMS (M+H) calcd for C$_{21}$H$_{29}$N$_4$O$_5$: 417.21381. found: 417.2147.

Compound 67B

5-Hydroxy-2-[4-(2-hydroxy-ethyl)-piperazin-1-yl]-1-methyl-6-oxo-1,6-dihydro-pyrimidine-4-carboxylic acid ethyl ester

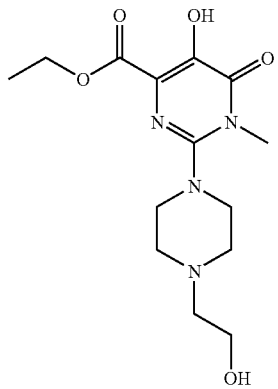

To a solution of 5-benzyloxy-2-[4-(2-hydroxy-ethyl)-piperazin-1-yl]-1-methyl-6-oxo-1,6-dihydro-pyrimidine-4-carboxylic acid ethyl ester (0.2058 g, 0.49 mmol) dissolved in EtOAc (20 mL) was added a small amount of palladium on carbon. The mixture was shaken under H$_2$ at 40 psi for 10 hours, filtered over celite and concentrated to yield the title compound as a yellow waxy solid (0.0483 g, 30% yield). $^1$H NMR (500 MHz, MeOD) δ: 4.44 (2H, q, J=7.1 Hz), 3.75 (2H, t, J=5.9 Hz), 3.56 (3H, s), 3.22–3.21 (4H, m), 2.78 (4H, bs), 2.68 (2H, t, J=5.9 Hz), 1.41 (3H, t, J=7.2 Hz). HRMS (M+H) calcd for C$_{14}$H$_{23}$N$_4$O$_5$: 327.16685. found: 327.1661.

Compound 67

N-[(4-fluorophenyl)methyl]-1,6-dihydro-5-hydroxy-2-[4-(2-hydroxyethyl)-1-piperazinyl]-1-methyl-6-oxo-4-pyrimidinecarboxamide

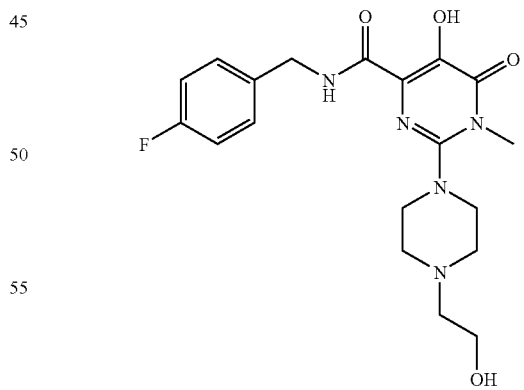

5-Hydroxy-2-[4-(2-hydroxy-ethyl)-piperazin-1-yl]-1-methyl-6-oxo-1,6-dihydro-pyrimidine-4-carboxylic acid ethyl ester (0.024 g, 0.074 mmol) was dissolved in DMF (1 mL) to which was added 4-fluoro-benzyl amine (0.047 mL, 0.37 mmol). The mixture was stirred at 70° C. for 2 hours. The resulting mixture was purified by chromatography (YMC Combiprep ODS-A, 30 mm×50 mm, MeOH/H2O/0.1%

TFA) to yield the title compound as a white powder (0.0149 g, 50% yield). $^1$H NMR (500 MHz, MeOD) δ: 8.81 (1H, bs), 7.40 (2H, dd, J=8.5, 5.5 Hz), 7.08 (2H, t, J=8.8 Hz), 4.59 (2H, d, J=6.1 Hz), 3.94 (2H, t, J=5.2 Hz), 3.70 (4H, d, J=11.3 Hz), 3.58 (3H, s), 3.47–3.35 (6H, m). HRMS (M+H) calcd for $C_{19}H_{25}FN_4O_5$: 406.18907. found: 406.1895.

Compound 68

N-[(4-fluoro-3-methylphenyl)methyl]-1,6-dihydro-5-hydroxy-2-[4-(2-hydroxyethyl)-1-piperazinyl]-1-methyl-6-oxo-4-pyrimidinecarboxamide

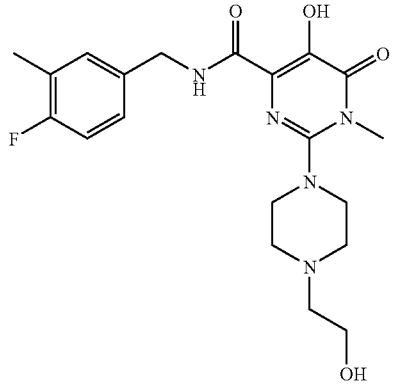

Colorless oil $^1$H NMR (500 MHz, MeOD) δ: 8.79 (1H, bs), 7.24 (1H, d, J=7.3 Hz), 7.20–7.18 (1H, m), 6.99 (1H, t, J=9.0 Hz), 4.54 (2H, s), 3.94 (2 H, s), 3.71–3.67 (4H, m), 3.58 (3H, s), 3.43–3.35 (6H, m), 2.26 (3H, d, J=1.5 Hz). HRMS (M+H) calcd for $C_{20}H_{27}FN_4O_5$: 420.20472. found: 420.2068.

Compound 69

N-[(4-fluorophenyl)methyl]-1,6-dihydro-5-hydroxy-1-methyl-6-oxo-2-(1-piperazinyl)-4-pyrimidinecarboxamide

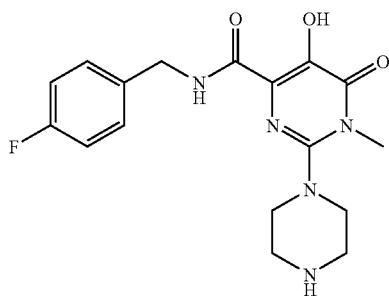

White solid, $^1$H NMR (300 MHz, DMSO) δ: 9.28 (1H, t, J=6.0 Hz), 7.35 (2H, dd, J=8.6, 5.7 Hz), 7.16 (2H, J=8.8 Hz), 4.46 (2H, d, J=6.2 Hz), 3.39 (3H, s), 3.00–2.98 (4H, m), 2.84–2.81 (4H, m). HRMS (M+H) calcd for $C_{17}H_{22}FN_5O_3$: 362.16285. found: 362.1619. CHN theoretical: C, 56.50; H, 5.57; N, 19.38; F, 5.25. found: C, 56.29; H, 5.52; N, 19.18; F, 5.54.

Compound 70

N-[(4-fluoro-3-methylphenyl)methyl]-1,6-dihydro-5-hydroxy-1-methyl-6-oxo-2-(1-piperazinyl)-4-pyrimidinecarboxamide

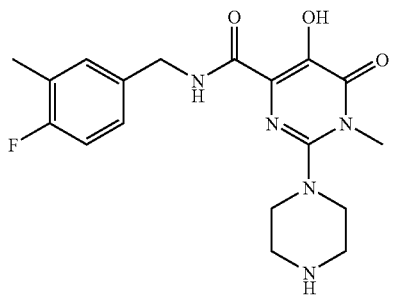

White solid $^1$H NMR (500 MHz, DMSO) δ: 9.26 (1H, t, J=5.0 Hz), 7.22 (1H, dd, J=7.6, 1.5 Hz), 7.18–7.15 (1H, m), 7.08 (1H, t, J=9.1 Hz), 4.42 (2H, d, J=6.4 Hz), 3.39 (3H, s), 3.00–2.98 (4H, m), 2.84–2.82 (4H, m), 2.21 (3H, d, J=1.5 Hz). HRMS (M+H) calcd for $C_{18}H_{22}FN_5O_3$: 376.17850. found: 376.1783.

Compound 71

2-(4-acetyl-1-piperazinyl)-N-[(4-fluorophenyl)methyl]-1,6-dihydro-5-hydroxy-1-methyl-6-oxo-4-pyrimidinecarboxamide

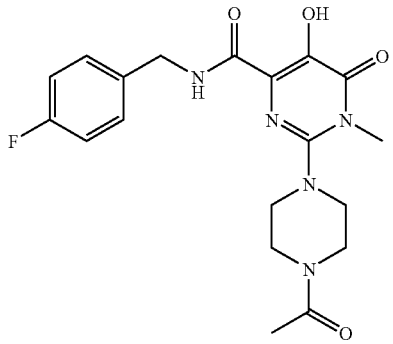

White solid $^1$H NMR (500 MHz, CDCl$_3$) δ: 11.75 (1H, s), 7.68 (1H, s), 7.29 (2H, dd, J=8.4, 5.3 Hz), 7.04 (2H, t, J=8.5 Hz), 4.56 (2H, d, J=6.1 Hz), 3.74 (2H, s), 3.59 (2H, s), 3.55 (3H, s), 3.02 (4H, d, J=17.7 Hz), 2.11 (2H, s). HRMS (M+H) calcd for $C_{19}H_{23}FN_5O_4$: 404.17342. found: 404.1753. CHN theoretical 0.8 mol H$_2$O: C, 54.62; H, 5.69; N, 16.76; F, 4.55. found: C, 54.62; H, 5.50; N, 16.41; F, 4.50.

Compound 72

2-(4-acetyl-1-piperazinyl)-N-[(4-fluoro-3-methylphenyl)methyl]-1,6-dihydro-5-hydroxy-1-methyl-6-oxo-4-pyrimidinecarboxamide

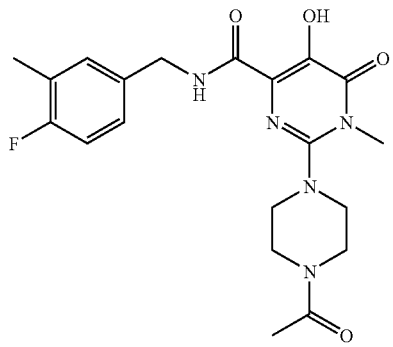

White solid $^1$H NMR (500 MHz, CDCl$_3$) δ: 11.78 (1H, s), 7.66 (1H, s), 7.13 (1H, d, J=7.0 Hz), 7.11–7.08 (1H, m), 6.97 (1H, t, J=8.8 Hz), 4.52 (2H, d, J=6.1 Hz), 3.74 (2H, s), 3.60 (2H, s), 3.55 (3H, s), 3.02 (4H, d, J=18.6 Hz), 2.26 (3 H, d, J=1.8 Hz), 2.12 (3H, s). HRMS (M+H) calcd for C$_{20}$H$_{25}$FN$_5$O$_4$: 418.18907. found: 418.1885. CHN theoretical 0.5 mol H$_2$O: C, 56.33; H, 5.91; N, 16.42; F, 4.46. found: C, 56.41; H, 5.68; N, 16.55; F, 4.64.

Compound 73

N-[(4-fluorophenyl)methyl]-1,6-dihydro-5-hydroxy-1-methyl-6-oxo-2-(4-propyl-1-piperazinyl)-4-pyrimidinecarboxamide

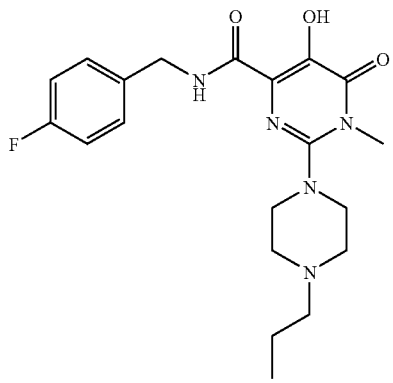

Brown oil $^1$H NMR (500 MHz, CDCl$_3$) δ: 12.0 (1H, bs), 7.82 (1H, t, J=6.1 Hz), 7.29 (2H, dd, J=8.4, 5.3 Hz), 7.01 (3H, t, J=8.5 Hz), 4.54 (2H, d, J=6.4 Hz), 3.72 (2H, d, J=11.6 Hz), 3.49 (3H, s), 3.43–3.39 (4H, m), 3.04–2.97 (4H, m), 1.84–1.76 (2H, m), 1.01 (3H, t, J=7.3 Hz). HRMS (M+H) calcd for C$_{20}$H$_{27}$FN$_5$O$_3$: 404.20980. found: 404.2095.

Compound 74

N-[(4-fluoro-3-methylphenyl)methyl]-1,6-dihydro-5-hydroxy-1-methyl-6-oxo-2-(4-propyl-1-piperazinyl)-4-pyrimidinecarboxamide

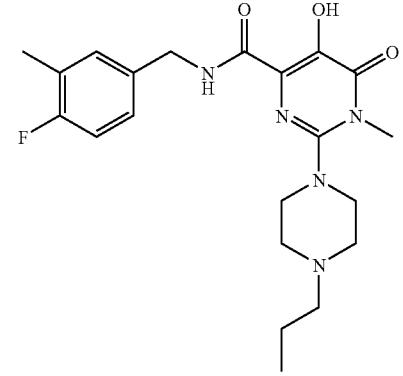

Brown oil $^1$H NMR (500 MHz, CDCl$_3$) δ: 12.0 (1H, bs), 7.86 (1H, t, J=5.8 Hz), 7.12–7.07 (2H, m), 6.92 (1H, t, J=8.8 Hz), 4.48 (2H, d, J=6.1 Hz), 3.68 (2H, d, J=10.7 Hz), 3.46–3.40 (4H, m), 3.04–0.01 (4H, m), 2.22 (3H, d, J=1.5 Hz), 1.81–1.74 (2H, m), 0.99 (3H, t, J=7.3 Hz). HRMS (M+H) calcd for C$_{21}$H$_{28}$FN$_5$O$_3$: 418.22545. found: 418.2247.

Compound 75

N-[(4-fluorophenyl)methyl]-1,6-dihydro-5-hydroxy-1-methyl-6-oxo-2-[4-(2-pyridinyl)-1-piperazinyl]-4-pyrimidinecarboxamide

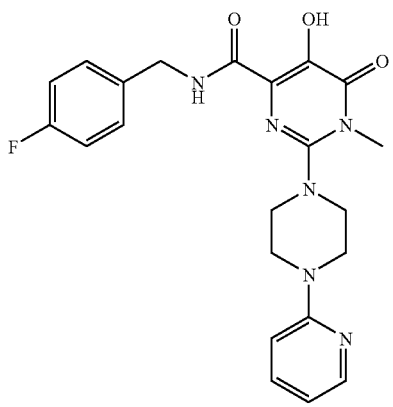

Pale pink foam $^1$H NMR (500 MHz, CDCl$_3$) δ: 8.14 (1H, d, J=5.8 Hz), 7.93 (1H, t, J=8.8 Hz), 7.85 (1H, t, J=6.2 Hz), 7.31 (2H, dd, J=8.5, 5.5 Hz), 7.04–6.99 (3H, m), 6.95 (1H, t, J=6.6 Hz), 4.45 (2H, d, J=6.4 Hz), 3.90–3.88 (4H, m), 3.56 (3H, s), 3.30–3.28 (4H, m). HRMS (M–H) calcd for C$_{22}$H$_{22}$FN$_6$O$_3$: 437.17374. found: 437.1716.

Compound 76

N-[(4-fluoro-3-methylphenyl)methyl]-1,6-dihydro-5-hydroxy-1-methyl-6-oxo-2-[4-(2-pyridinyl)-1-piperazinyl]-4-pyrimidinecarboxamide

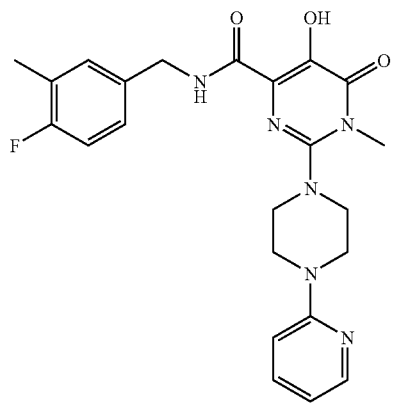

Pale pink foam $^1$H NMR (500 MHz, CDCl$_3$) δ: 8.18 (1H, d, J=5.8 Hz), 7.93 (1H, t, J=7.8 Hz), 7.78 (1H, t, J=6.1 Hz), 7.15–7.10 (2H, m), 7.01 (1H, d, J=9.1 Hz), 6.97–6.94 (2H, m), 4.52 (2H, d, J=6.4 Hz), 3.91–3.89 (4H, m), 3.57 (3H, s), 3.30–3.28 (4H, m), 2.25 (3H, m). HRMS (M−H) calcd for C$_{23}$H$_{24}$FN$_6$O$_3$: 451.18939. found: 451.1894.

Compound 77

N-[(4-fluorophenyl)methyl]-1,6-dihydro-5-hydroxy-1-methyl-6-oxo-2-[4-(2-pyrimidinyl)-1-piperazinyl]-4-pyrimidinecarboxamide

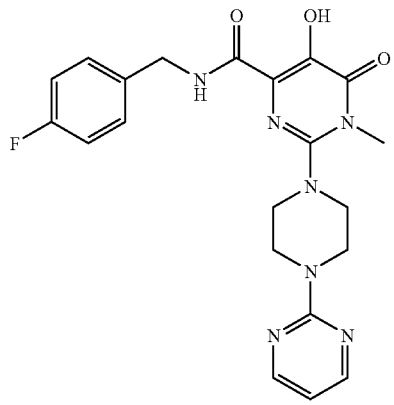

White solid $^1$H NMR (300 MHz, CDCl$_3$) δ: 11.70 (bs), 8.33 (2H, d, J=4.7 Hz), 7.73 (1H, t, J=6.2 Hz), 7.29 (2H, dd, J=8.6, 5.3 Hz), 7.04 (2H, t, J=8.6 Hz), 6.56 (1H, t, J=4.7 Hz), 4.56 (2H, d, J=6.2 Hz), 3.97 (4H, t, J=4.8 Hz), 3.60 (3 H, s), 3.10 (4H, s, J=5.1 Hz). HRMS (M+H) calcd for C$_{21}$H$_{23}$FN$_7$O$_3$: 440.18465. found: 440.1847. CHN theoretical: C, 57.39; H, 5.04; N, 22.31; F, 4.32. found: C, 57.19; H, 5.03; N, 22.52; F, 4.42.

Compound 78

N-[(4-fluoro-3-methylphenyl)methyl]-1,6-dihydro-5-hydroxy-1-methyl-6-oxo-2-[4-(2-pyrimidinyl)-1-piperazinyl]-4-pyrimidinecarboxamide

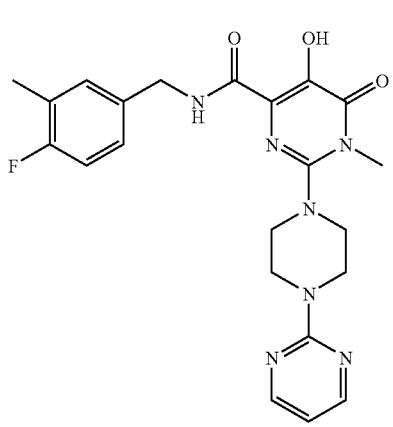

Lavender solid $^1$H NMR (300 MHz, CDCl$_3$) δ: 11.92 (bs), 8.54 (2H, d, J=4.8 Hz), 7.72 (1H, t, J=5.8 Hz), 7.14–7.08 (2H, m), 6.95 (1H, t, J=8.8 Hz), 6.80 (1H, t, J=3.6 Hz), 4.51 (2H, d, J=6.2 Hz), 4.60 (4H, bs), 3.60 (3H, s), 3.20 (4H, bs), 2.24 (3H, s). HRMS (M+H) calcd for C$_{22}$H$_{25}$FN$_7$O$_3$: 454.20030. found: 454.1989.

Compound 79

N-[(4-fluorophenyl)methyl]-1,6-dihydro-5-hydroxy-1-methyl-6-oxo-2-(4-phenyl-1-piperazinyl)-4-pyrimidinecarboxamide

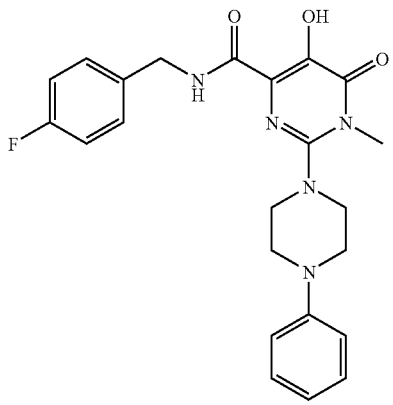

White solid $^1$H NMR (300 MHz, CDCl$_3$) δ: 11.46 (1H, s), 7.77 (1H, t, J=6.0 Hz), 7.33–7.27 (4H, m), 7.05 (3H, t, J=8.6 Hz), 7.01–6.91 (3H, m), 4.58 (2H, d, J=6.2 Hz), 3.58 (3H, s), 3.33–3.30 (4H, m), 3.24–3.21 (4H, m). HRMS (M+H) calcd for C$_{23}$H$_{25}$FN$_5$O$_3$: 438.19415. found: 438.1955. CHN theoretical: C, 63.14; H, 5.52; N, 16.00; F, 4.34. found: C, 63.11; H, 5.47; N, 15.79; F, 4.36.

Compound 80

N-[(4-fluoro-3-methylphenyl)methyl]-1,6-dihydro-5-hydroxy-1-methyl-6-oxo-2-(4-phenyl-1-piperazinyl)-4-pyrimidinecarboxamide

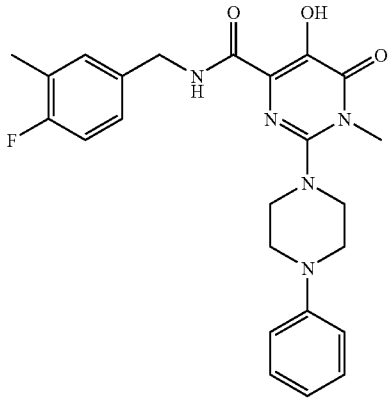

White solid $^1$H NMR (300 MHz, CDCl$_3$) δ: 11.73 (1H, bs), 7.32–7.27 (3H, m), 7.15–7.05 (2H, m), 7.01–6.91 (3H, m), 4.54 (2H, d, J=6.2 Hz), 3.58 (3H, s), 3.33–3.31 (4H, m), 3.24–3.21 (4H, m), 2.26 (3H, s). HRMS (M+H) calcd for C$_{24}$H$_{27}$FN$_5$O$_1$: 452.20980. found: 452.2104.

Compound 81

N-[(4-fluorophenyl)methyl]-1,6-dihydro-5-hydroxy-2-[4-[2-(2-hydroxyethoxy)ethyl]-1-piperazinyl]-1-methyl-6-oxo-4-pyrimidinecarboxamide

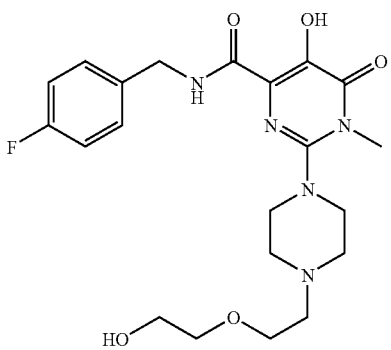

Colorless oil $^1$H NMR (300 MHz, MeOD) δ: 8.83–8.79 (1H, m), 7.36 (2H, dd, J=8.4, 5.5 Hz), 7.04 (2H, t, J=8.8 Hz), 4.55 (2H, s), 3.90–3.84 (2H, m), 3.73–3.60 (6H, m), 3.55 (3H, s), 3.47–3.45 (2H, m), 3.40–3.34 (2H, m), 3.31–3.29 (4H, m). HRMS (M–H) calcd for C$_{21}$H$_{27}$N$_5$O$_5$F: 448.19962. found: 448.2015.

Compound 82

N-[(4-fluoro-3-methylphenyl)methyl]-1,6-dihydro-5-hydroxy-2-[4-[2-(2-hydroxyethoxy)ethyl]-1-piperazinyl]-1-methyl-6-oxo-4-pyrimidinecarboxamide

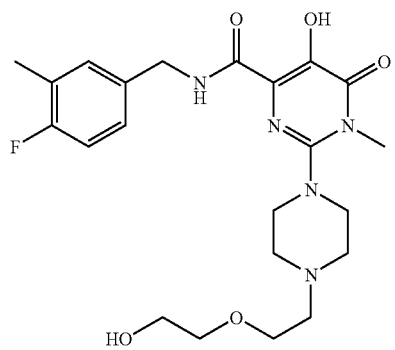

Colorless oil $^1$H NMR (300 MHz, MeOD) δ: 8.77 (1H, bs), 8.12 (1H, s), 7.22–7.08 (2H, m), 6.95 (1H, t, J=9.0 Hz), 4.41 (2H, d, J=51.2 Hz), 3.91–3.84 (2H, m), 3.73–3.60 (6H, m), 3.54 (3H, s), 3.64 (2H, d, J=4.4 Hz), 3.39–3.23 (6H, m), 2.23 (3H, s). HRMS (M–H) calcd for C$_{22}$H$_{29}$N$_5$O$_5$F: 462.21527. found: 462.2147.

Example 11

Preparation of Compounds 83A–90

A Representative Procedure is Given for Compound 83

Compound 83A

5-Benzyloxy-1-methyl-6-oxo-2-piperazin-1-yl-1,6-dihydro-pyrimidine-4-carboxylic acid ethyl ester

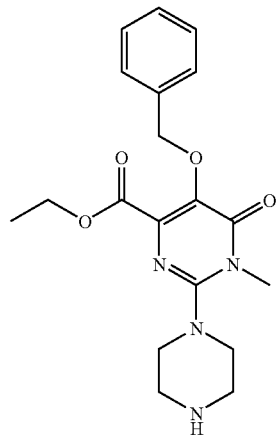

Following the procedure described for the synthesis of compound 67A 5-Benzyloxy-2-methanesulfonyl-1-methyl-6-oxo-1,6-dihydro-pyrimidine-4-carboxylic acid ethyl ester (7.0 g, 19.2 mmol) was reacted with piperazine (17.0 g, 192 mmol) and to yield the title compound as a pale yellow oil (0.0418 g, 42% yield). $^1$H NMR (500 MHz, CDCl$_3$) δ: 7.45 (2H, d, J=6.7 Hz), 7.34–7.27 (3H, m), 5.13 (2H, s), 4.30 (2H, q, J=7.2 Hz), 3.49 (3H, s), 3.15–3.13 (4H, m), 2.98–2.96 (4H, m), 1.89 (1H, bs), 1.27 (3H, J=7.2 Hz). HRMS (M+H) calcd for C$_{19}$H$_{25}$N$_4$O$_4$: 373.21414. found: 373.1866.

Compound 83B

5-Benzyloxy-2-(4-methanesulfonyl-pinerazin-1-yl)-1-methyl-6-oxo-1,6-dihydro-pyrimidine-4-carboxylic acid ethyl ester

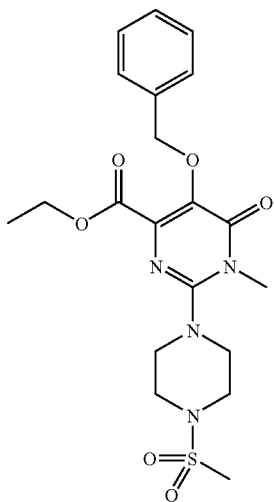

To a solution of ethyl 5-(benzyloxy)-1-methyl-6-oxo-2-(piperazin-1-yl)-1,6-dihydropyrimidine-4-carboxylate (0.145 g, 0.39 mmol) dissolved in pyridine (2 mL) was added methane sulfonyl chloride (0.31 mL, 0.39 mmol) and the resulting mixture was stirred at room temp for 2 hours. The mixture was diluted with EtOAc and the solids were removed by filtration and the solution was concentrated. The residue was purified by flash chromatography eluting with 0% to 50% to 100% EtOAc/hexane to give the title compound as a white foam (0.1364 g, 78% yield). $^1$H NMR (300 MHz, CDCl$_3$) δ: 7.46 (2H, dd, J=7.9, 1.6 Hz), 7.37–7.27 (3H, m), 5.16 (2H, s), 4.30 (2H, q, J=7.2 Hz), 3.50 (3H, s,), 3.34 (8H, d, J=6.2 Hz), 2.82 (3H, s), 1.28 (3H, t, J=7.1 Hz). HRMS (M+H) calcd for C$_{20}$H$_{27}$N$_4$O$_6$S: 451.16514. found: 451.1663.

Compound 83C

5-Hydroxy-2-(4-methanesulfonyl-piperazin-1-yl)-1-methyl-6-oxo-1,6-dihydro-pyrimidine-4-carboxylic acid ethyl ester

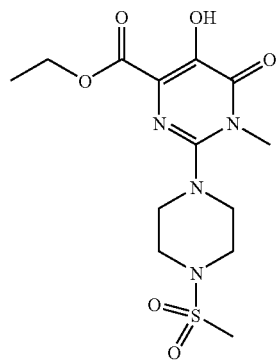

5-Benzyloxy-2-(4-methanesulfonyl-piperazin-1-yl)-1-methyl-6-oxo-1,6-dihydro-pyrimidine-4-carboxylic acid ethyl ester (0.22 g, 0.49 mmol) was treated with TFA to yield the title compound as a brown oily TFA salt (0.1564 g). $^1$H NMR (500 MHz, CDCl$_3$) δ: 4.45 (2H, q, J=7.1 Hz), 3.59 (3H, s), 3.42–3.39 (4H, m), 3.28–3.26 (4H, m), 2.86 (3H, s), 1.42 (3H, t, J=7.0 Hz). HRMS (M–H) calcd for C$_{13}$H$_{19}$N$_4$O$_6$S: 359.10253. found: 359.1039.

Compound 83

N-[(4-fluorophenyl)methyl]-1,6-dihydro-5-hydroxy-1-methyl-2-[4-(methylsulfonyl)-1-piperazinyl]-6-oxo-4-pyrimidinecarboxamide

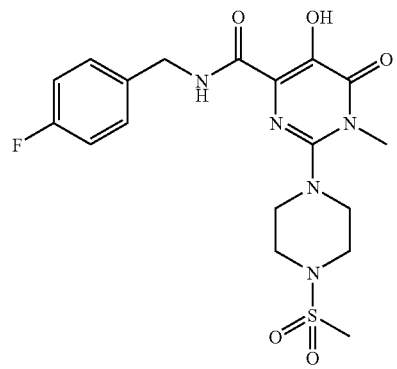

N-[(4-fluorophenyl)methyl]-1,6-dihydro-5-hydroxy-1-methyl-2-[4-(methylsulfonyl)-1-piperazinyl]-6-oxo-4-pyrimidinecarboxamide was synthesized from 5-hydroxy-2-(4-methanesulfonyl-piperazin-1-yl)-1-methyl-6-oxo-1,6-dihydro-pyrimidine-4-carboxylic acid ethyl ester and 4-fluorobenzylamine as described in example to yield the title compound as a white solid $^1$H NMR (300 MHz, MeOD) δ: 8.88 (1H, t, J=5.9 Hz), 7.37 (2H, dd, J=8.6, 5.3 Hz), 7.05 (2H, t, J=8.8 Hz), 4.55 (2H, d, J=6.2 Hz), 3.55 (3H, s), 3.39–3.36 (4H, m), 3.26–3.23 (4H, m), 2.88 (3H, s). HRMS (M+H) calcd for C$_{18}$H$_{23}$FN$_5$O$_5$S: 440.14040. found: 440.1386.

Compound 84

N-[(4-fluoro-3-methylphenyl)methyl]-1,6-dihydro-5-hydroxy-1-methyl-2-[4-(methylsulfonyl)-1-piperazinyl]-6-oxo-4-pyrimidinecarboxamide

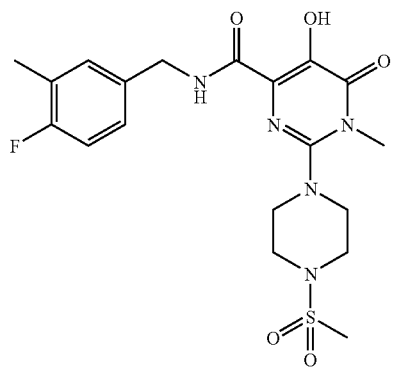

Pale lavender solid $^1$H NMR (300 MHz, MeOD) δ: 8.83 (1H, bs), 7.21 (1H, d, J=7.7 Hz), 7.18–7.16 (1H, m), 6.96 (1H, t, J=9.0 Hz), 4.51 (2H, d, J=4.0 Hz), 3.55 (3H, s), 3.39–3.36 (4H, m), 3.26–3.23 (4H, m), 2.88 (3H, s), 2.24 (3H, d, J=1.8 Hz). HRMS (M+H) calcd for $C_{19}H_{25}FN_5O_5S$: 454.15605. found: 454.1570.

Compound 85

N-[(4-fluorophenyl)methyl]-1,6-dihydro-5-hydroxy-1-methyl-6-oxo-2-[4-[(2-oxo-1-imidazolidinyl)carbonyl]-1-piperazinyl]-4-pyrimidinecarboxamide

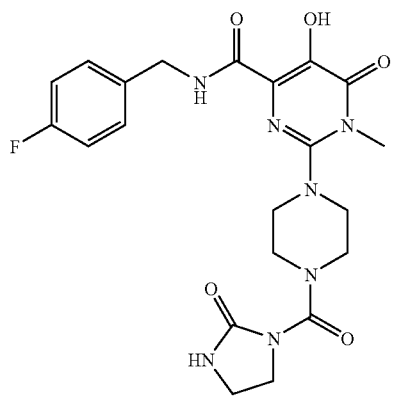

White solid $^1$H NMR (300 MHz, CDCl$_3$) δ: 11.74 (1H, s), 7.75 (1H, t, J=5.7 Hz), 7.32–7.27 (2H, m), 7.04 (2H, t, J=8.6 Hz), 4.82 (1H, s), 4.56 (2H, d, J=6.2 Hz), 3.87 (2H, t, J=7.7 Hz), 3.66–3.63 (4H, m), 3.55 (3H, s), 3.48 (2H, t, J=7.7 Hz), 3.12–3.09 (4H, m). HRMS (M+H) calcd for $C_{21}H_{25}FN_7O_5$: 474.19013. found: 474.1908.

Compound 86

N-[(4-fluoro-3-methylphenyl)methyl]-1,6-dihydro-5-hydroxy-1-methyl-6-oxo-2-[4-[(2-oxo-1-imidazolidinyl)carbonyl]-1-piperazinyl]-4-pyrimidinecarboxamide

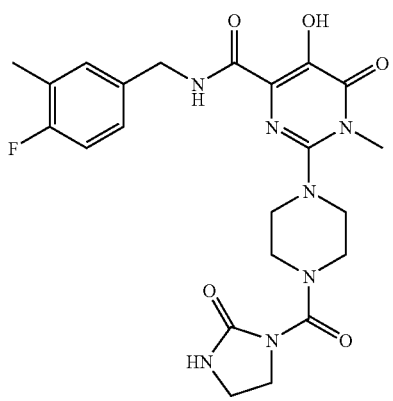

White solid $^1$H NMR (300 MHz, CDCl$_3$) δ: 11.71 (1H, bs), 7.73 (1H, t, J=6.0 Hz), 7.14–7.02 (2H, m), 6.96 (1H, t, J=8.8 Hz), 5.50 (1H, bs), 4.51 (2H, d, J=6.2 Hz), 3.88 (2H, t, J=7.9 Hz), 3.66–3.64 (4H, m), 3.54 (3H, s), 3.51 (2H, t, J=7.9 Hz), 3.12–3.09 (4H, m). HRMS (M+H) calcd for $C_{22}H_{27}FN_7O_5Na$: 510.18772. found: 510.1884.

Compound 87

N-[(4-fluorophenyl)methyl]-1,6-dihydro-5-hydroxy-1-methyl-2-[4-[(methylamino)carbonyl]-1-piperazinyl]-6-oxo-4-pyrimidinecarboxamide

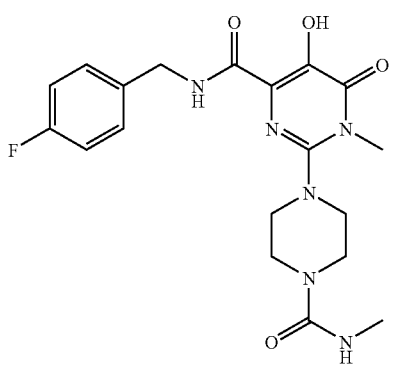

White solid $^1$H NMR (300 MHz, MeOD) δ: 7.36 (2H, dd, J=8.6, 5.3 Hz), 7.05 (2H, t, J=8.8 Hz), 4.54 (2H, s), 3.56 (3H, s), 3.52 (4H, t, J=4.9 Hz), 3.11 (4H, t, J=5.1 Hz), 2.73 (3H, s). HRMS (M+H) calcd for $C_{19}H_{24}FN_6O_4$: 419.18432. found: 419.1858. CHN theoretical 1.0 mol H$_2$O: C, 52.29; H, 5.77; N, 19.26; F, 4.35. found: C, 52.02; H, 5.72; N, 19.12; F, 4.13.

Compound 88

N-[(4-fluoro-3-methylphenyl)methyl]-1,6-dihydro-5-hydroxy-1-methyl-2-[4-[(methylamino)carbonyl]-1-piperazinyl]-6-oxo-4-pyrimidinecarboxamide

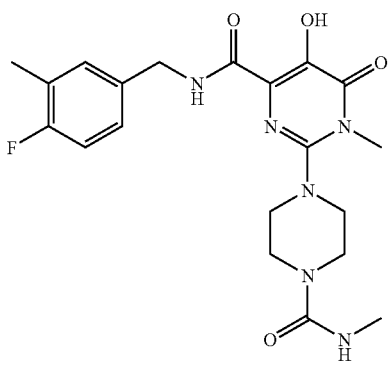

White solid ¹H NMR (300 MHz, MeOD) δ: 8.78 (1H, t, J=5.8 Hz), 7.20 (1H, d, J=7.7 Hz), 7.18–7.13 (1H, m), 6.96 (1H, t, J=9.0 Hz), 4.50 (2H, d, J=4.0 Hz), 3.55 (3H, s), 3.52 (4H, t, J=4.9 Hz), 3.11 (4H, t, J=4.9 Hz), 2.73 (3H, s), 2.23 (3H, d, J=1.8 Hz). HRMS (M+H) calcd for $C_{20}H_{26}FN_6O_4$: 433.19997. found: 433.1990. CHN theoretical 0.8 mol $H_2O$: C, 53.76; H, 6.00; N, 18.81; F, 4.25. found: C, 53.72; H, 5.61; N, 18.81; F, 4.19.

Compound 89

N-[(4-fluorophenyl)methyl]-1,6-dihydro-5-hydroxy-1-methyl-2-[4-(4-morpholinylcarbonyl)-1-piperazinyl]-6-oxo-4-pyrimidinecarboxamide

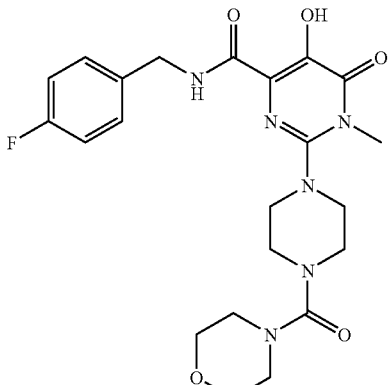

White solid (0.064 g, 39% yield). ¹H NMR (300 MHz, CDCl₃) δ: 7.72 (1H, t, J=6.0 Hz), 7.29 (2H, dd, J=8.4, 5.5 Hz), 7.04 (2H, t, J=8.8 Hz), 4.57 (2H, d, J=6.2 Hz), 3.71–3.67 (4H, m), 3.55 (3H, s), 3.45–3.42 (4H, m), 3.34–3.32 (4H, m), 3.06–3.03 (4H, m). HRMS (M–H) calcd for $C_{22}H_{26}N_6O_5F$: 473.19487. found: 473.1952.

Compound 90

N-[(4-fluoro-3-methylphenyl)methyl]-1,6-dihydro-5-hydroxy-1-methyl-2-[4-(4-morpholinylcarbonyl)-1-piperazinyl]-6-oxo-4-pyrimidinecarboxamide

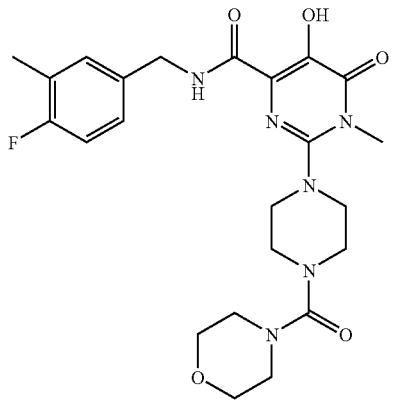

White solid (0.0648 g, 38% yield). ¹H NMR (300 MHz, CDCl₃) δ: 7.69 (1H, t, J=5.8 Hz), 7.14–7.08 (2H, m), 6.97 (1H, t, J=8.8 Hz), 4.52 (2H, d, J=6.2 Hz), 3.71–3.68 (4H, m), 3.56 (3H, s), 3.45–3.42 (4H, m), 3.34–3.31 (4H, m), 3.06–3.04 (4 H, m), 2.27 (3H, s). HRMS (M–H) calcd for $C_{23}H_{28}N_6O_5F$: 487.21052. found: 487.2094. CHN theoretical 0.4 mol $H_2O$, 1.0 mol TFA: C, 49.25; H, 5.09; N, 13.78; F, 12.46. found: C, 49.08; H, 5.08; N, 13.61; F, 12.23.

Example 12

Preparation of Compounds 91–101

Compounds 91–101 were prepared according to the methods described above.

Compound 91

N-[(4-fluorophenyl)methyl]-1,6-dihydro-5-hydroxy-1-methyl-6-oxo-2-(1-pyrrolidinyl)-4-pyrimidinecarboxamide

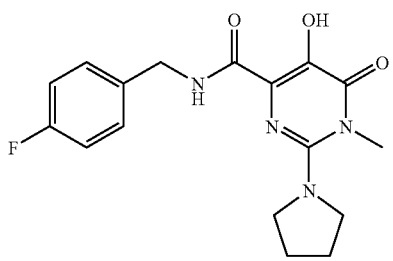

HPLC 100% AP (RT, 2.44 min); MS (ESI) m/z 347 (M+H), 345 (M–H); HRMS (ESI) calcd for for $C_{17}H_{20}N_4O_3F$ (M+H) 347.1519. found 347.1520 (δ+0.2 ppm); ¹H NMR (CDCl₃, 300 MHz) δ ppm 1.91 (4H, m), 3.45 (4H, t, J=6.6 Hz), 3.49 (3H, s), 4.56 (2H, d, J=6 Hz), 7.04 (2H, m), 7.30 (2H, m), 7.80 (1H, br), 11.34 (1H, s)

Compound 92

2-(1-azetidinyl)-N-[(4-fluorophenyl)methyl]-1,6-dihydro-5-hydroxy-1-methyl-6-oxo-4-pyrimidinecarboxamide

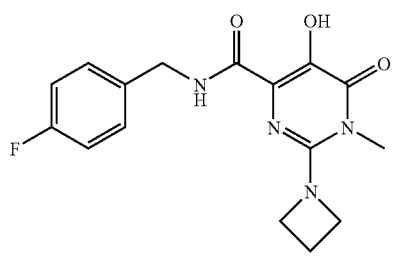

HPLC 98% AP (RT, 2.23 min); HRMS (ESI) calcd for for $C_{16}H_{18}N_4O_3F$ (M+H) 333.1363. found 333.1360 (δ–0.6 ppm); $^1$H NMR (CDCl$_3$, 500 MHz) δ ppm 2.30 (2H, qi, J=7.5 Hz), 3.37 (3H, s), 4.05 (4H, t, J=7.5 Hz), 4.55; (2H, q, J=6.5 Hz), 7.02 (2H, td, J=7, 2 Hz), 7.29 (2H, m), 7.82 (1H, br), 11.35 (1H, s); $^{13}$C NMR (CDCl$_3$, 125.8 MHz) δ ppm 16.2, 31.1, 42.3, 52.6, 115.7, 115.8, 125.3, 125.8, 129.3, 129.4, 133.4, 133.4, 142.4, 149.7, 159.5, 161.4, 163.4, 168.6; UV (MeOH) λmax 245 nm (ε1.03×10$^4$), 337 (ε5.0× 10$^3$); Elemental Analysis calcd for $C_{16}H_{17}N_4O_3F.1/5H_2O$, C, 57.20; H, 5.22; N, 16.68. found C, 57.43; H, 5.77; N, 16.86.

Compound 93

2-(1-azetidinyl)-N-[(4-fluoro-3-methylphenyl)methyl]-1,6-dihydro-5-hydroxy-1-methyl-6-oxo-4-pyrimidinecarboxamide

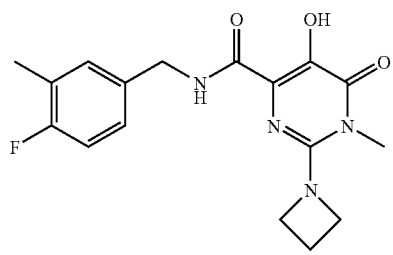

HPLC 96% AP (RT, 2.44 min); HRMS (ESI) calcd for for $C_{17}H_{20}N_4O_3F$ (M+H) 347.1519. found 347.1515 (δ–1.3 ppm); $^1$H NMR (CDCl$_3$, 500 MHz) δ ppm 2.25 (3H, s), 2.30 (2H, qi, J=7.5 Hz), 3.37 (3H, s), 4.05 (4H, t, J=7.5 Hz), 4.50; (2H, q, J=6.5 Hz), 6.95 (1H, t, J=9 Hz), 7.07–7.13 (2H, m), 7.81 (1H, br), ~11 (1 H, br); $^{13}$C NMR (CDCl$_3$, 125.8 MHz) δ ppm 14.5, 14.5, 16.2, 31.1, 42.4, 52.7, 115.2, 115.4, 125.3, 125.4, 125.5, 126.5, 126.5, 130.8, 130.9, 133.0, 133.1, 142.3, 149.7, 159.6, 159.9, 161.9, 168.5; UV (MeOH) λmax 245 nm (ε8.95×10$^3$), 336 (ε4.43×10$^3$); Elemental Analysis calcd for $C_{17}H_{19}N_4O_3F.1/2H_2O$, C, 57.46; H, 5.67; N, 15.77. found C, 57.87; H, 5.62; N, 15.46.

Compound 94

2-[4-(aminocarbonyl)-1-piperidinyl]-N-[(4-fluorophenyl)methyl]-1,6-dihydro-5-hydroxy-1-methyl-6-oxo-4-pyrimidinecarboxamide

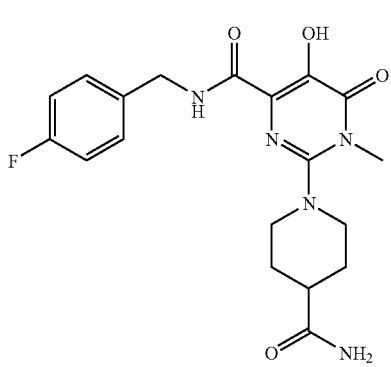

HPLC 96% AP (RT, 2.44 min); HRMS (ESI) calcd for for $C_{17}H_{20}N_4O_3F$ (M+H) 347.1519. found 347.1515 (δ–1.3 ppm); $^1$H NMR (CDCl$_3$, 500 MHz) δ ppm 2.25 (3H, s), 2.30 (2H, qi, J=7.5 Hz), 3.37 (3H, s), 4.05 (4H, t, J=7.5 Hz), 4.50, (2H, q, J=6.5 Hz), 6.95 (1H, t, J=9 Hz), 7.07–7.13 (2H, m), 7.81 (1H, br), ~11 (1H, br); $^{13}$C NMR (CDCl$_3$, 125.8 MHz) δ ppm 14.5, 14.5, 16.2, 31.1, 42.4, 52.7, 115.2, 115.4, 125.3, 125.4, 125.5, 126.5, 126.5, 130.8, 130.9, 133.0, 133.1, 142.3, 149.7, 159.6, 159.9, 161.9, 168.5; UV (MeOH) λmax 245 nm (ε8.95×10$^3$), 336 (ε4.43×10$^3$); Elemental Analysis calcd for $C_{17}H_{19}N_4O_3F.1/2H_2O$, C, 57.46; H, 5.67; N, 15.77. found C, 57.87; H, 5.62; N, 15.46.

Compound 95

2-[(2S)-2-(aminocarbonyl)-1-pyrrolidinyl]-N-[(4-fluorophenyl)methyl]-1,6-dihydro-5-hydroxy-1-methyl-6-oxo-4-pyrimidinecarboxamide

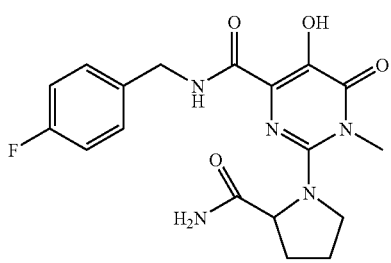

Yield 67% (white solid, trituration with Et$_2$O); HPLC ~95% AP (RT, 1.80 min); HRMS (ESI) calcd for for $C_{18}H_{21}N_5O_4F$ (M+H) 390.1578. found 390.1570 (δ–1.9 ppm); $^1$H NMR (CDCl$_3$, 300 MHz) δ ppm 1.97 (2H, m), 2.21 (1H, m), 2.40 (1H, m), 3.26 (1H, br.t, J=~9 Hz)), 3.56 (3H, s), 3.76 (1H, m), 4.46–4.60 (3H, m), 5.19 (1H, br.s), 5.91 (1H, br.s), 7.02 (2H, t, J=8.4 Hz), 7.30 (2H, m), 7.86 (1H, br), 11.47 (1H, s).

Compound 96

4-pyrimidineN-[(4-fluorophenyl)methyl]-1,6-dihydro-5-hydroxy-2-[2-(hydroxymethyl)-1-piperidinyl]-1-methyl-6-oxo-carboxamide

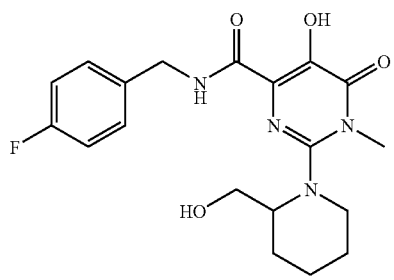

¹H NMR (300 MHz, MeOD) δ: 8.90 (1H, bs), 7.39–7.35 (2H, m), 7.05 (2H, t, J=8.8 Hz), 4.72 (1H, dd, J=12.6, 2.7 Hz), 4.56 (2H, s), 4.57–4.49 (1H, m), 3.65–3.57 (1H, m), 3.49 (3H, s), 3.49–3.43 (1H, m), 3.11–3.02 (1H, m), 2.04–1.92 (3H, m), 1.72–1.58 (3H, m). HRMS (M+H) calcd for $C_{19}H_{24}FN_4O_4$: 391.17817. found: 391.1783. CHN theoretical for 1.3 mol TFA and 0.55 mol $H_2O$: C, 47.29; H, 4.67; N, 10.21; F, 16.97. found: C, 47.69; H, 4.36; N, 10.23; F, 16.86.

Compound 97

N-[(4-fluoro-3-methylphenyl)methyl]-1,6-dihydro-5-hydroxy-2-[2-(hydroxymethyl)-1-piperidinyl]-1-methyl-6-oxo-4-pyrimidinecarboxamide

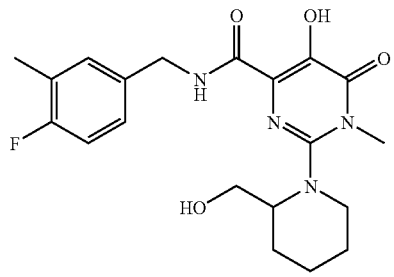

¹H NMR (300 MHz, MeOD) δ: 8.90 (1H, bs), 7.22–7.14 (2H, m), 6.96 (1H, t, J=9.0 Hz), 4.75 (1H, dd, J=12.8, 2.9 Hz), 4.51 (2H, s), 3.65–3.57 (1H, m), 3.48 (3H, s), 3.48–3.44 (1H, m), 3.11–3.03 (1H, m), 2.23 (3H, s), 2.04–1.91 (3H, m), 1.73–1.57 (3H, m). HRMS (M+H) calcd for $C_{20}H_{26}FN_4O_4$: 405.19382. found: 405.1958. CHN theoretical for 1.4 mol TFA and 0.3 mol $H_2O$: C, 48.09; H, 4.78; N, 9.84; F, 17.35. found: C, 48.41; H, 4.47; N, 9.63; F, 17.18.

Compound 98

N-[(4-fluorophenyl)methyl]-1,6-dihydro-5-hydroxy-2-[2-(2-hydroxyethyl)-1-piperidinyl]-1-methyl-6-oxo-4-pyrimidinecarboxamide

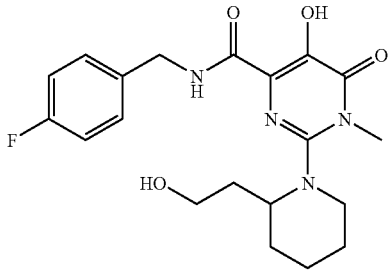

¹H NMR (300 MHz, CDCl₃) δ: 9.18–9.10 (1H, m), 8.65–8.60 (1H, m), 8.27 (1H, t, J=6.4 Hz), 7.31 (2H, dd, J=8.6, 5.3 Hz), 6.99 (2H, t, J=8.6 Hz), 4.75–4.67 (1H, m), 4.52–4.49 (2H, m), 4.41–4.34 (1H, m), 3.32 (3H, s), 3.36–3.22 (2H, m,), 2.95–2.83 (1H, m), 2.35–2.25 (1H, m), 2.16–2.07 (1H, m), 1.94–1.90 (2H, d, J=11.71 Hz), 1.80–1.66 (3H, m), 1.56–1.46 (1H, m). HRMS (M–H) calcd for $C_{20}H_{24}FN_4O_4$: 403.17816. found: 403.1780. CHN theoretical for 1.4 mol TFA and 0.4 mol $H_2O$: C, 47.94; H, 4.80; N, 9.81; F, 17.29. found: C, 47.87; H, 4.62; N, 9.61; F, 17.58.

Compound 99

N-[(4-fluoro-3-methylphenyl)methyl]-1,6-dihydro-5-hydroxy-2-[2-(2-hydroxyethyl)-1-piperidinyl]-1-methyl-6-oxo-4-pyrimidinecarboxamide

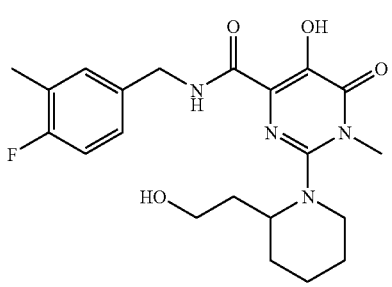

¹H NMR (300 MHz, CDCl₃) δ: 9.14–9.09 (1H, m), 8.57–8.53 (1H, m), 8.24 (1H, t, J=6.4 Hz), 7.16–7.11 (2H, m), 6.92 (1H, t, J=8.8 Hz), 4.78–4.70 (1H, m), 4.47 (2H, t, J=5.1 Hz), 4.42–4.36 (1H, m), 3.34 (3H, s), 3.34–3.19 (2H, m), 2.92–2.84 (1H, m), 2.35–2.25 (1H, m), 2.23 (3H, s), 2.18–2.09 (1H, m), 1.92 (2H, d, J=12.1 Hz), 1.82–1.67 (3H, m), 1.57–1.46 (1H, m). HRMS (M–H) calcd for $C_{21}H_{26}FN_4O_4$: 417.19381. found: 417.1930. CHN theoretical for 1.5 mol TFA and 0.5 mol $H_2O$: C, 48.16; H, 4.97; N, 9.36; F, 17.46. found: C, 48.43; H, 4.81; N, 9.34; F, 17.46.

Compound 100

N-[(4-fluorophenyl)methyl]-1,6-dihydro-5-hydroxy-1-methyl-6-oxo-2-(6-oxo-1(6H)-pyridazinyl)-4-pyrimidinecarboxamide

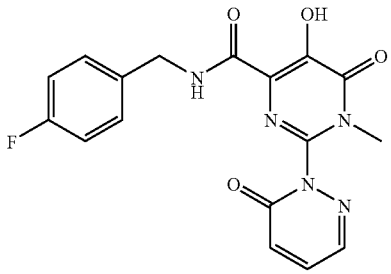

HPLC 98% AP (RT, 1.98 min); HRMS (ESI) calcd for for $C_{17}H_{13}N_5O_4F$ (M–H) 370.0952. found 370.0937 (δ–3.9 ppm); $^1H$ NMR (CDCl$_3$, 500 MHz) δ ppm 3.37 (3H, s), 4.52, (2H, q, J=6 Hz), 6.99–7.03 (2H, m), 7.06 (1H, dd, J=10, 1.5 Hz), 7.25–7.28 (2H, m), 7.36 (1H, dd, J=10, 4 Hz), 7.66 (1H, br.t, J=6 Hz), 7.93 (1H, dd, J=4, 1.5 Hz), 12.49 (1H, s); $^{13}C$ NMR (CDCl$_3$, 125.8 MHz) δ ppm 31.1, 42.6, 115.71, 115.87, 124.6, 129.81, 129.87, 131.6, 132.7, 133.1, 138.1, 140.1, 149.2, 158.2, 159.1, 161.47, 163.43, 167.6; UV (MeOH) λmax 251 nm (ε1.01×10$^4$), 297 (ε1.13×10$^4$); Elemental Analysis calcd for $C_{17}H_{14}N_5O_4F$, C, 54.98; H, 3.80; N, 18.86. found C, 54.72, H, 3.64; N, 18.86.

Compound 101

N-[(4-fluoro-3-methylphenyl)methyl]-1,6-dihydro-5-hydroxy-1-methyl-6-oxo-2-(6-oxo-1(6H)-pyridazinyl)-4-pyrimidinecarboxamide

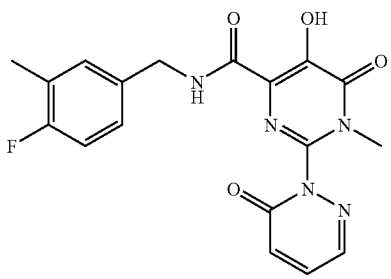

HPLC 96% AP (RT, 2.16 min); HRMS (ESI) calcd for for $C_{18}H_{15}N_5O_4F$ (M–H) 384.1108. found 384.1112 (δ+1.0 ppm). $^1H$ NMR (CDCl$_3$, 500 MHz) δ ppm 2.23 (3H, s), 3.37. (3H, s), 4.48; (2H, q, J=6 Hz), 6.94 (1H, t, J=9 Hz), 7.06 ( 1H, dd, J=9.5, 1.5 Hz), 7.07 (1H, m), 7.11 (1H, m), 7.37 (1H, dd, J=9.5, 3.5 Hz), 7.63 (1H, br.t, J=6 Hz), 7.94 (1H, dd, J=3.5, 1.5 Hz), 12.53 (1H, s); $^{13}C$ NMR (CDCl$_3$, 125.8 MHz) δ ppm 14.58, 14.61, 31.1, 42.7, 115.2, 115.4, 124.6, 125.4, 125.5, 127.0, 127.1, 131.31, 131.35, 131.5, 132.3, 132.4,133.1, 138.1, 140.1, 149.2, 158.2, 159.1, 160.02, 161.98, 167.6; UV (MeOH) λmax 251 nm (ε8.75×10$^3$), 297 (ε9.80×10$^3$); Elemental Analysis calcd for $C_{18}H_{16}N_5O_4F$, C, 56.10; H, 4.18; N, 18.17. found C, 55.17; H, 3.72; N, 17.91.

Compound 102

2-(6-fluoro-1,3-dihydro-1-oxo-2H-isoindol-2-yl)-N-[(4-fluorophenyl)methyl]-1,6-dihydro-5-hydroxy-1-methyl-6-oxo-4-pyrimidinecarboxamide

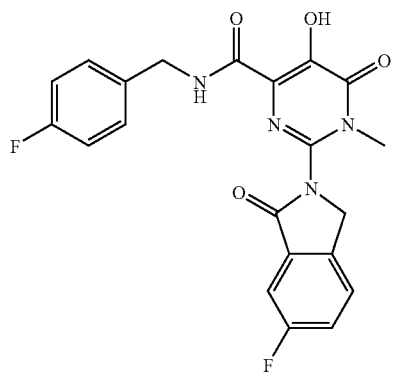

HPLC 100% AP (RT, 2.51 min); HRMS (ESI) calcd for for $C_{21}H_{17}N_4O_4F_2$ (M+H) 427.1218. found 427.1212 (δ–0.6 ppm). $^1H$ NMR (CDCl$_3$, 300 MHz) δ ppm 3.59 (3H, s), 4.59 (2H, q, J=6.2 Hz), 4.91 (2H, s), 7.02 (2H, t, J=8.7 Hz), 7.27–7.59 (5H, m), 12.17 (1H, s)

Biological Activity

HIV-Integrase Inhibition Activity

To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, J. Virol. 69, 5908–5911 (1995). The sequences of substrate and target DNA were described in Nucleic Acid Research 22, 1121–1122 (1994). Results are shown in the table. Activity equal to A refers to a compound having IC$_{50}$=0.003 to 0.10 μM while B and C denote compounds the following IC$_{50}$=0.1 to 1.0 μM and IC$_{50}$≧1.0 μM respectively.

| Compound | Activity |
| --- | --- |
| 1 | A |
| 2 | A |
| 3 | B |
| 4 | A |
| 5 | A |
| 6 | A |
| 7 | C |
| 8 | A |
| 9 | A |
| 10 | A |
| 11 | B |
| 12 | A |

| Compound | Activity |
|---|---|
| 13 | A |
| 14 | A |
| 15 | A |
| 16 | C |
| 17 | A |
| 18 | A |
| 19 | A |
| 20 | A |
| 21 | C |
| 22 | A |
| 23 | A |
| 24 | A |
| 25 | C |
| 26 | C |
| 27 | C |
| 28 | B |
| 29 | A |
| 30 | B |
| 31 | C |
| 32 | B |
| 33 | B |
| 34 | B |
| 35 | B |
| 36 | B |
| 37 | B |
| 38 | C |
| 39 | C |
| 40 | C |
| 41 | C |
| 42 | B |
| 43 | B |
| 44 | C |
| 45 | B |
| 46 | B |
| 47 | B |
| 48 | B |
| 49 | C |
| 50 | C |
| 52 | A |
| 53 | A |
| 54 | A |
| 55 | A |
| 56 | A |
| 57 | A |
| 58 | B |
| 59 | A |
| 60 | A |
| 61 | B |
| 62 | A |
| 63 | A |
| 64 | A |
| 65 | A |
| 66 | A |
| 67 | A |
| 68 | A |
| 69 | B |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 84 | |
| 85 | A |
| 86 | A |
| 87 | A |
| 88 | A |
| 91 | A |
| 92 | A |
| 93 | A |
| 94 | A |
| 95 | A |
| 96 | B |
| 97 | A |
| 98 | A |
| 99 | A |
| 100 | B |
| 101 | A |
| 102 | A |

Inhibition of HIV Replication

A recombinant NL-Rluc virus was construcuted in which a section of the nef gene from NL4–3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research*. ed. Aldovini A, Walker B D. 71–76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the table. Activity equal to A refers to a compound having $EC_{50}$=0.003 to 0.10 μM while B and C denote compounds the following $EC_{50}$=0.1 to 1.0 μM and $EC_{50} \geq 1.0$ μM respectively.

| Compound | Activity |
|---|---|
| 1 | B |
| 2 | A |
| 3 | C |
| 4 | B |
| 5 | B |
| 6 | B |
| 8 | B |
| 9 | A |
| 10 | B |
| 11 | B |
| 12 | A |
| 13 | A |
| 14 | B |
| 15 | B |
| 17 | C |
| 18 | A |
| 19 | A |
| 20 | B |
| 22 | B |
| 23 | B |
| 24 | B |
| 28 | C |
| 29 | B |
| 32 | C |

-continued

| Compound | Activity |
|---|---|
| 35 | C |
| 36 | C |
| 37 | C |
| 42 | C |
| 43 | C |
| 45 | C |
| 46 | C |
| 47 | C |
| 48 | C |
| 52 | B |
| 53 | A |
| 54 | A |
| 55 | A |
| 56 | A |
| 57 | A |
| 58 | C |
| 59 | C |
| 60 | C |
| 61 | B |
| 62 | B |
| 63 | B |
| 65 | A |
| 66 | A |
| 67 | B |
| 68 | B |
| 69 | C |
| 70 | B |
| 71 | B |
| 72 | A |
| 73 | B |
| 74 | A |
| 75 | A |
| 76 | A |
| 77 | A |
| 78 | A |
| 79 | A |
| 80 | B |
| 85 | B |
| 86 | A |
| 87 | B |
| 88 | A |
| 91 | A |
| 92 | A |
| 94 | B |

Although the invention has been described with respect to specific aspects, those skilled in the art will recognize that other aspects not specifically described herein are intended to be within the scope of the claims which follow.

What is claimed is:

1. A compound having the formula $$R^1\text{—}CH_2\text{—}N(R^2)\text{—}B \quad (I)$$

wherein:
$R^1$ is —$C_1$–$C_6$ alkyl, $C_3$–$C_6$ cycloalkyl, -aryl, —$C_1$–$C_6$ alkyl-aryl, or —$C_1$–$C_6$ alkyl-diaryl;
$R^2$ is —H, —OH, —$C_1$–$C_6$ alkyl unsubstituted or substituted with 1–3 $R^3$, or —$OR^4$;
Each $R^3$ is independently selected from the group consisting of —H, -halo, —CN, —$C_1$–$C_2$ perfluoroalkyl, —$C_1$–$C_6$ alkyl, —$C_1$–$C_2$ perfluoroalkoxy, and —$C_1$–$C_6$ alkoxy;
$R^4$ is —$C_{1-C6}$ alkyl or —$C_3$–$C_6$ cycloalkyl;
B is selected from the group consisting of

[structures shown with $R^5$, $R^6$]

$R^5$ is —$NR^7R^8$; or Het where Het is selected from the group consisting of fluorooxindole, methyltriazole, [1,2]thiazinane-1,1-dioxide, azetidinyl, and

[piperazine structure with X]

wherein X is a bond, O, S, NH, N-methyl, N-propyl, N-acetyl, N-(2-hydroxyethyl), N-pyridinyl, N-pyrazinyl, N-pyrimidinyl, N-(N-morpholinyl)carbonyl, N—$SO_2$Me, N-phenyl, CH($CONH_2$), $CH_2$, and CHOH, and wherein the bond attaching $R^5$ is made to a nitrogen atom in said Het;
$R^6$ is —H, —$C_1$–$C_6$ alkyl unsubstituted or substituted with 1–3 $R^3$; and
$R^7$ and $R^8$ are independently —H or —$C_1$–$C_6$ alkyl;
or pharmaceutically acceptable enantiomer, diastereomer, or salt, thereof.

2. The compound of claim 1 wherein the aryl is substituted with 1–3 $R^3$.

3. The compound of claim 1 wherein $R^1$ is -aryl, —$C_1$–$C_6$ alkyl-aryl, or —$C_1$–$C_6$ alkyl diaryl.

4. The compound of claim 3 wherein $R^1$ is -aryl, —$C_1$–$C_6$ alkyl-phenyl, or —$C_1$–$C_6$ alkyl-diphenyl.

5. The compound of claim 4 wherein the aryl is selected from the group consisting of phenyl, naphthyl, furanyl, thienyl, indolyl, and benzimidazolyl, and aryl and phenyl are unsubstituted or substituted with 1–3 $R^3$.

6. A compound of claim 4 wherein $R^1$ is aryl selected from the group consisting of naphthyl, 2-methyl-5-furanyl, 2-thienyl, 3-indolyl, and 2-benzimidazolyl.

7. A compound of claim 4 wherein $R^1$ is phenyl unsubstituted or substituted with 1–3 $R^3$.

8. A compound of claim 7 wherein $R^1$ is 3-fluorophenyl, 4-fluorophenyl, 2,4-diflourophenyl, 3,4-diflourophenyl, 3-methyl-4-fluorophenyl, 3-chloro-4-fluorophenyl, 3-chlorophenyl, 4-chlorophenyl, 3,4-dichlorophenyl, 3,5-dichlorophenyl, 3-methylphenyl, 4-methylphenyl, or 3,4-dimethylphenyl.

9. A compound of claim 1 where $R^2$ is —H, methyl, —OH or methoxy.

10. A compound of claim 9 where $R^2$ is —H.

11. A compound of claim 1 wherein $R^6$ is —$C_1$–$C_6$ alkyl.

12. A compound of claim 11 wherein $R^6$ is methyl.

13. A compound of claim 1 wherein $R^5$ is selected from the group consisting of fluorooxindole and methyltriazole.

14. A compound of claim 1 wherein $R^5$ is selected from the group consisting of [1,2]thiazinane-1,1-dioxide, and

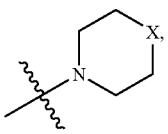

wherein X is a bond, O, S, NH, N-methyl, N-propyl, N-acetyl, N-(2-hydroxyethyl), N-pyridinyl, N-pyrazinyl, N—SO₂Me, CH₂, and CHOH.

15. A compound selected from the group consisting of
N-[(4-fluorophenyl)methyl]-1,6-dihydro-5-hydroxy-1-methyl1-6-oxo-2-(tetrahydro-1,1-dioxido-2H-1,2-thiazin-2-yl)-4-pyrimidinecarboxamide;
N-[(3,4-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(4-chlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3-chlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[3-(4-fluorophenyl)propyl]-1,6-dihydro-5-hydroxy-1-methyl-6-oxo-2-(tetrahydro-1,1-dioxido-2H-1,2-thiazin-2-yl)-4-pyrimidinecarboxamide;
N-[3-(3,4-dichlorophenyl)propyl]-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-N-[(4-methylphenyl)methyl]-6-oxo-2-(tetrahydro-1,1-dioxido-2H-1,2-thiazin-2-yl)-4-pyrimidinecarboxamide;
1,6-dihydro-5-hydroxy-1-methyl-N-[(3-methylphenyl)methyl]-6-oxo-2-(tetrahydro-1,1-dioxido-2H-1,2-thiazin-2-yl)-4-pyrimidinecarboxamide;
1,6-dihydro-5-hydroxy-N-[(4-methoxyphenyl)methyl]-1-methyl-6-oxo-2-(tetrahydro-1,1-dioxido-2H-1,2-thiazin-2-yl)-4-pyrimidinecarboxamide;
1,6-dihydro-5-hydroxy-N-[(3-methoxyphenyl)methyl]-1-methyl-6-oxo-2-(tetrahydro-1,1-dioxido-2H-1,2-thiazin-2-yl)-4-pyrimidinecarboxamide;
N-[(3,5-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(4-fluoro-3-methylphenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3-fluoro4-methylphenyl)methyl]-1,6-dihydro-5-hydroxy-1-methyl1-6-oxo-2-(tetrahydro-1,1-dioxido-2H-1,2-thiazin-2-yl)-4-pyrimidinecarboxamide;
N-[(3,4-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[2-(4-fluorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(2,4-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3-chloro-4-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(3,4-dimethylphenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-6-oxo-N-(1-phenylethyl)-2-(tetrahydro-1,1-dioxido-2H-1,2-thiazin-2-yl)-4-pyrimidinecarboxamide;
N-[(4-fluorophenyl)methyl]-1,6-dihydro-5-hydroxy-1-methyl-2-(4-morpholinyl)-6-oxo-4-pyrimidinecarboxamide;
N-[[4-fluoro-3-(trifluoromethyl)phenyl]methyl]-1,6-dihydro-5-hydroxy-1-methyl-6-oxo-2-(tetrahydro-1,1-dioxido-2H-1,2-thiazin-2-yl)-4-pyrimidinecarboxamide;
N-[2-(3-fluorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;
N-[(2,4-dimethoxyphenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-N-[(5-methyl-2-furanyl)methyl]-6-oxo-2-(tetrahydro-1,1-dioxido-2H-1,2-thiazin-2-yl)-4-pyrimidinecarboxamide;
1,6-dihydro-5-hydroxy-N-[(2-methoxyphenyl)methyl]-1-methyl-6-oxo-2-(tetrahydro-1,1-dioxido-2H-1,2-thiazin-2-yl)-4-pyrimidinecarboxamide;
N-(2,2-diphenylethyl)-1,6-dihydro-5-hydroxy-1-methyl-6-oxo-2-(tetrahydro-1,1-dioxido-2H-1,2-thiazin-2-yl)-4-pyrimidinecarboxamide;
N-[2-(4-chlorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-N-[2-(4-methoxyphenyl)ethyl]-1-methyl-6-oxo-2-(tetrahydro-1,1-dioxido-2H-1,2-thiazin-2-yl)-4-pyrimidinecarboxamide;
N-[(2-fluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-6-oxo-2-(tetrahydro-1,1-dioxido-2H-1,2-thiazin-2-yl)-N-[[3-(trifluoromethyl)phenyl]methyl]-4-pyrimidinecarboxamide;
N-[2-(3-chlorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-6-oxo-N-(2-phenylethyl)-2-(tetrahydro-1,1-dioxido-2H-1,2-thiazin-2-yl)-4-pyrimidinecarboxamide;
1,6-dihydro-5-hydroxy-1-methyl-6-oxo-N-[(1S)-1-phenylethyl]-2-(tetrahydro-1,1-dioxido-2H-1,2-thiazin-2-yl)-4-pyrimidinecarboxamide;
1,6-dihydro-5-hydroxy-1-methyl-6-oxo-2-(tetrahydro-1,1-dioxido-2H-1,2-thiazin-2-yl)-N-[[4-(trifluoromethyl)phenyl]methyl ]-4-pyrimidinecarboxamide;
N-[1-(4-fluorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;
N-(2-furanylmethyl)-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-6-oxo-2-(tetrahydro-1,1-dioxido-2H-1,2-thiazin-2-yl)N-(2-thienylmethyl)-4-pyrimidinecarboxamide;
N-(1,2-diphenylethyl)-1,6-dihydro-5-hydroxy-1-methyl-6-oxo-2-(tetrahydro-1,1-dioxido-2H-1,2-thiazin-2-yl)-4-pyrimidinecarboxamide;
1,6-dihydro-5-hydroxy-1-methyl-6-oxo-N-(phenylmethyl)-2-(tetrahydro-1,1-dioxido-2H-1,2-thiazin-2-yl)-4-pyrimidinecarboxamide;

N-[(2-chlorophenyl)methyl]-1,6-dihydro-5-hydroxy-1-methyl-6-oxo-2-tetrahydro-1,1-dioxido-2H-1,2-thiazin-2-yl)-4-pyrimidinecarboxamide;

1,6-dihydro-5-hydroxy-1-methyl-N-[(2-methylphenyl)methyl]-6-oxo-2-(tetrahydro-1,1-dioxido-2H-1,2-thiazin-2-yl)-4-pyrimidinecarboxamide;

1,6-dihydro-5-hydroxy-N-[2-(2-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-N-[2-(3-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-1-methyl-N-[2-(4-methylphenyl)ethyl]-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[(3,4,5-trimethoxyphenyl)methyl]-4-pyrimidinecarboxamide;

N-[(2,5-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-N-[(1R,2S)-2-hydroxy-1,2-diphenylethyl]-1-methyl-6-oxo-2-(tetrahydro-1,1-dioxido-2H-1,2-thiazin-2-yl)-4-pyrimidinecarboxamide;

N-[(2,4-dichlorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

N-[[3,5-bis(trifluoromethyl)phenyl]methyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(2,5-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[[2-(trifluoromethyl)phenyl]methyl]-4-pyrimidinecarboxamide;

1,6-dihydro-5-hydroxy-1-methyl-6-oxo-N-(1-phenylpropyl)-2-(tetrahydro-1,1-dioxido-2H-1,2-thiazin-2-yl)-4-pyrimidinecarboxamide;

4-pyrimidinecarboxamide, N-[1-(4-chlorophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

N-[(3,5-difluorophenyl)methyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-2-(tetrahydro-1,1-dioxido-2H-1,2-thiazin-2-yl)-N-[[3-(trifluoromethoxy)phenyl]methyl]-4-pyrimidinecarboxamide;

1,6-dihydro-5-hydroxy-1-methyl-N-[1-(1-naphthalenyl)ethyl]-6-oxo-2-(tetrahydro-1,1-dioxido-2H-1,2-thiazin-2-yl)-4-pyrimidinecarboxamide;

N-[1-(4-bromophenyl)ethyl]-1,6-dihydro-5-hydroxy-1-methyl-6-oxo-2-(tetrahydro-1,1-dioxido-2H-1,2-thiazin-2-yl)-4-pyrimidinecarboxamide;

1,6-dihydro-5-hydroxy-1-methyl-N-[1-(2-naphthalenyl)ethyl]-6-oxo-2-(tetrahydro-1,1-dioxido-2H-1,2-thiazin-2-yl)-4-pyrimidinecarboxamide;

1,6-dihydro-5-hydroxy-1-methyl-N-[1-(4-methylphenyl)ethyl]-6-oxo-2-(tetrahydro-1,1-dioxido-2H-1,2-thiazin-2-yl)-4-pyrimidinecarboxamide;

1,6-dihydro-5-hydroxy-N-[1-(3-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-N-[1-(4-methoxyphenyl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-N-[2-(1H-indol-3-yl)ethyl]-1-methyl-6-oxo-2-(tetrahydro-1,1-dioxido-2H-1,2-thiazin-2-yl)-4-pyrimidinecarboxamide;

1,6-dihydro-5-hydroxy-1-methyl-6-oxo-N-[(1S)-1-phenylpropyl]-2-(tetrahydro-1,1-dioxido-2H-1,2-thiazin-2-yl)-4-pyrimidinecarboxamide;

N-(1H-benzimidazol-2-ylmethyl)-1,6-dihydro-5-hydroxy-1-methyl-6-oxo-2-(tetrahydro-1,1-dioxido-2H-1,2-thiazin-2-yl)-4-pyrimidinecarboxamide;

N-[(4-fluorophenyl)methyl]-1,6-dihydro-5-hydroxy-1-methyl-2-(3-methyl-1H-1,2,4-triazol-1-yl)-6-oxo-4-pyrimidinecarboxamide;

N-[(3,4-dichlorophenyl)methyl]-1,6-dihydro-5-hydroxy-1-methyl-2-(3-methyl-1H-1,2,4-triazol-1-yl)-6-oxo-4-pyrimidinecarboxamide;

N-[(4-fluoro-3-methylphenyl)methyl]-1,6-dihydro-5-hydroxy-1-methyl-2-(3-methyl-1H-1,2,4-triazol-1-yl)-6-oxo-4-pyrimidinecarboxamide;

N-[(3,4-dichlorophenyl)methyl]-1,6-dihydro-5-hydroxy-1-methyl-2-(4-morpholinyl)-6-oxo-4-pyrimidinecarboxamide;

N-[(3-fluoro-4-methylphenyl)methyl]-1,6-dihydro-5-hydroxy-1-methyl-2-(4-morpholinyl)-6-oxo-4-pyrimidinecarboxamide;

N-[(4-fluoro-3-methylphenyl)methyl]-1,6-dihydro-5-hydroxy-1-methyl-2-(4-morpholinyl)-6-oxo-4-pyrimidinecarboxamide;

N-[(3-chloro-4-fluorophenyl)methyl]-1,6-dihydro-5-hydroxy-1-methyl-2-(4-morpholinyl)-6-oxo-4-pyrimidinecarboxamide;

N-[(3,4-dimethylphenyl)methyl]-1,6-dihydro-5-hydroxy-1-methyl-2-(4-morpholinyl)-6-oxo-4-pyrimidinecarboxamide;

N-[(4-fluorophenyl)methyl]-1,6-dihydro-5-hydroxy-1-methyl-2-(5-methyl-1H-1,2,4-triazol-1-yl)-6-oxo-4-pyrimidinecarboxamide;

N-[(3,4-dichlorophenyl)methyl]-1,6-dihydro-5-hydroxy-1-methyl-2-(5-methyl-1H-1,2,4-triazol-1-yl)-6-oxo-4-pyrimidinecarboxamide;

N-[(4-fluorophenyl)methyl]-1,6-dihydro-5-hydroxy-2-[4-(2-hydroxyethyl)-1-piperazinyl]-1-methyl-6-oxo-4-pyrimidinecarboxamide;

N-[(4-fluoro-3-methylphenyl)methyl]-1,6-dihydro-5-hydroxy-2-[4-(2-hydroxyethyl)-1-piperazinyl]-1-methyl-6-oxo-4-pyrimidinecarboxamide;

2-(4-acetyl-1-piperazinyl)-N-[(4-fluorophenyl)methyl]-1,6-dihydro-5-hydroxy-1-methyl-6-oxo-4-pyrimidinecarboxamide;

2-(4-acetyl-1-piperazinyl)-N-[(4-fluoro-3-methylphenyl)methyl]-1,6-dihydro-5-hydroxy-1-methyl-6-oxo-4-pyrimidinecarboxamide;

N-[(4-fluorophenyl)methyl]-1,6-dihydro-5-hydroxy-1-methyl-6-oxo-2-(4-propyl-1-piperazinyl)-4-pyrimidinecarboxamide;

N-[(4-fluoro-3-methylphenyl)methyl]-1,6-dihydro-5-hydroxy-1-methyl-6-oxo-2-(4-propyl-1-piperazinyl)-4-pyrimidinecarboxamide;

N-[(4-fluorophenyl)methyl]-1,6-dihydro-5-hydroxy-1-methyl-6-oxo-2-(1-piperazinyl)-4-pyrimidinecarboxamide;

N-[(4-fluoro-3-methylphenyl)methyl]-1,6-dihydro-5-hydroxy-1-methyl1-6-oxo-2-(1-piperazinyl)-4-pyrimidinecarboxamide;

N-[(4-fluorophenyl)methyl]-1,6-dihydro-5-hydroxy-2-(4-hydroxy-1-piperidinyl)-1-methyl-6-oxo-4-pyrimidinecarboxamide;

N-[(4-fluoro-3-methylphenyl)methyl]-1,6-dihydro-5-hydroxy-2-(4-hydroxy-1-piperidinyl)-1-methyl-6-oxo-4-pyrimidinecarboxamide;
2-(6-fluoro-1,3-dihydro-1-oxo-2H-isoindol-2-yl)-N-[(4-fluorophenyl)methyl]-1,6-dihydro-5-hydroxy-1-methyl-6-oxo-4-pyrimidinecarboxamide;
N-[(4-fluorophenyl)methyl]-1,6-dihydro-5-hydroxy-1-methyl-6-oxo-2-[4-(2-pyridinyl)-1-piperazinyl]-4-pyrimidinecarboxamide;
N-[(4-fluoro-3-methylphenyl)methyl]-1,6-dihydro-5-hydroxy-1-methyl-6-oxo-2-[4-(2-pyridinyl)-1-piperazinyl]-4-pyrimidinecarboxamide;
N-[(4-fluorophenyl)methyl]-1,6-dihydro-5-hydroxy-1-methyl-6-oxo-2-[4-(2-pyrimidinyl)-1-piperazinyl]-4-pyrimidinecarboxamide;
N-[(4fluoro-3-methylphenyl)methyl]-1,6-dihydro-5-hydroxy-1-methyl-6-oxo-2-[4-2-pyrimidinyl)-1-piperazinyl]-4-pyrimidinecarboxamide;
N-[(4-fluorophenyl)methyl]-1,6-dihydro-5-hydroxy-1-methyl-2-[4-(methylsulfonyl)-1-piperazinyl]-6-oxo-4-pyrimidinecarboxamide;
N-[(4-fluoro-3-methylphenyl)methyl]-1,6-dihydro-5-hydroxy-1-methyl-2-[4-(methylsulfonyl)-1-piperazinyl]-6-oxo-4-pyrimidinecarboxamide;
N-[(4-fluorophenyl)methyl]-1,6-dihydro-5-hydroxy-1-methyl-6-oxo-2-(1-pyrrolidinyl)-4-pyrimidinecarboxamide;
N-[(4-fluoro-3-methylphenyl)methyl]-1,6-dihydro-5-hydroxy-1-methyl-6-oxo-2-[2-(tetrahydro-1,1-dioxido-2H-1,2-thiazin-2-yl)ethyl]-4-pyrimidinecarboxamide;
N-[(4-fluorophenyl)methyl]-1,6-dihydro-5-hydroxy-1-methyl-6-oxo-2-[3-(tetrahydro-1,1-dioxido-2H-1,2-thiazin-2-yl)propyl]-4-pyrimidinecarboxamide;
N-[(4-fluorophenyl)methyl]-1,6-dihydro-5-hydroxy-1-methyl-6-oxo-2-[2-(tetrahydro-1,1-dioxido-2H-1,2-thiazin-2-yl)ethyl]-4-pyrimidinecarboxamide; and
N-[(3,4-dichlorophenyl)methyl]-1,6-dihydro-5-hydroxy-1-methyl-6-oxo-2-[2-(tetrahydro-1,1-dioxido-2H-1,2-thiazin-2-yl)ethyl]-4-pyrimidinecarboxamide.

16. A compound having the formula:

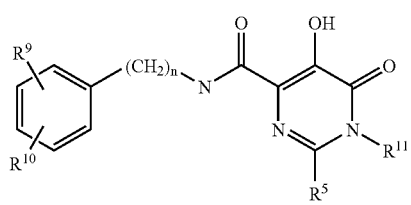

(II)

wherein, n is 1 to 4;

$R^5$ is Het where Het is selected from the group consisting of [1,2]thiazinane-1,1-dioxide, azetidinyl, and

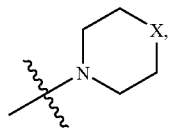

wherein X is a bond, O, NH, N-methyl, N-propyl, N-acetyl, N-(2-hydroxyethyl), N-pyridinyl, N-pyrimidinyl, N-(N-morpholinyl)carbonyl, N—SO$_2$Me, N-phenyl, CH(CONH$_2$), and CHOH, and wherein the bond attaching $R^5$ is made to a nitrogen atom in said Het;

$R^9$ and $R^{10}$ are each independently H, halo, $C_{1-6}$ alkyl, $C_{1-6}$ alkoxy or $CF_3$; and $R^{11}$ is $C_{1-6}$ alkyl;

or a pharmaceutically acceptable enantiomer, diastereomer, or salt thereof.

17. The compound of claim 16 having one of the following structures;

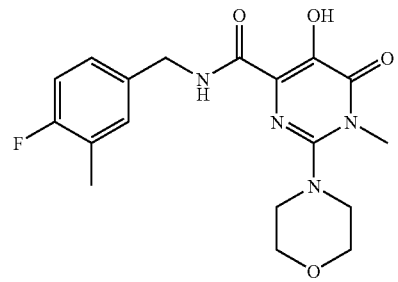

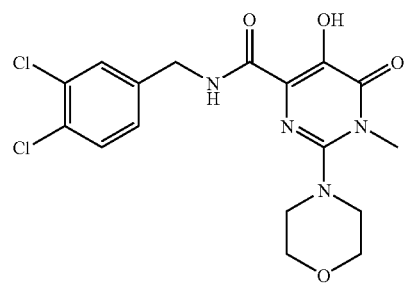

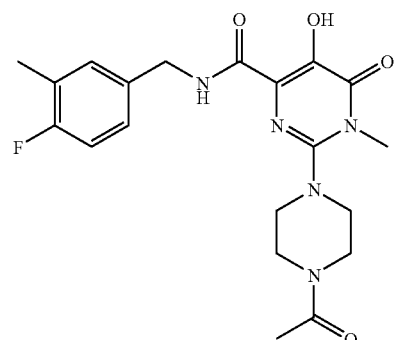

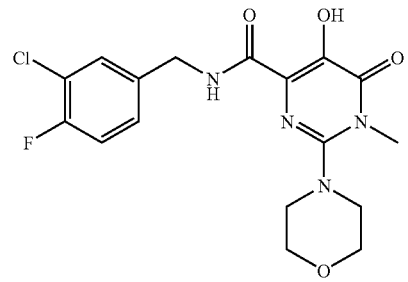

-continued

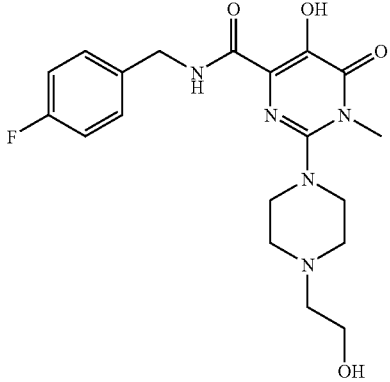

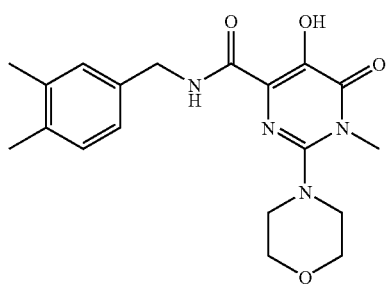

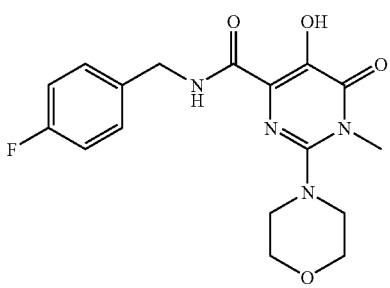

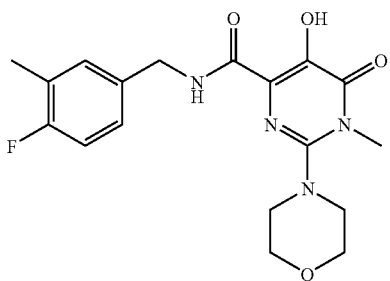

-continued

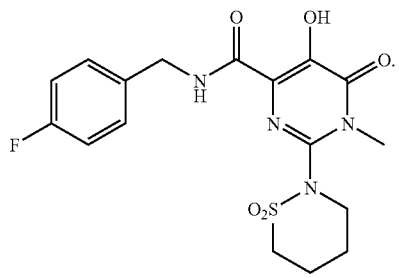

18. A compound having the formula:

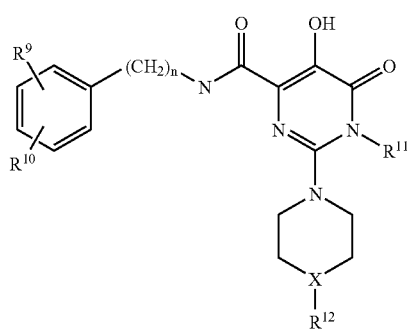

wherein n is 1 to 4;
$R^9$ and $R^{10}$ are each independently H, halo, $C_{1-6}$ alkyl, $C_{1-6}$ alkoxy or $CF_3$;
X is C, O or N;
$R^{11}$ is $C_{1-6}$ alkyl; and
$R^{12}$ is H, $C_{1-6}$ alkyl, $C_{1-6}$ alkoxy, $C_{1-6}$ hydroxyalkyl, $C_{1-6}$ alkyl carbonyl, $C_{6-10}$ aryl, $C_{7-14}$ alkyl; aryl, $C_{1-6}$ alkylsulfonyl, $C_{6-10}$ arylsulfonyl, $C_{1-6}$ alkylurea, $C_{3-7}$ cycloalkylurea, carbonyl, carboxamide or hydroxyl;
said $R^{12}$ being present only when X is C or N;
or a pharmaceutically acceptable enantiomer, diastereomer, or salt thereof.

19. The compound of claim 18 wherein m is 1.

20. The compound of claim 18 wherein $R_9$ is halo.

21. The compound of claim 20 wherein $R_9$ is fluoro or chloro.

22. The compound of claim 20 wherein $R_{10}$ is methyl.

23. The compound of claim 21 wherein $R_{10}$ is chloro.

24. The compound of claim 18 wherein $R_9$ is methyl.

25. The compound of claim 18 wherein $R_9$ and $R_{10}$ are not both H.

26. The compound of claim 18 wherein X is O.

27. The compound of claim 18 wherein X is N.

28. A composition comprising the compound of claim 1 and a pharmaceutically acceptable carrier.

29. A method of treating an HIV-1 infection in a patient, comprising administering to the patient a therapeutically effective amount of the compound of claim 1, or a pharmaceutically acceptable enantiomer, diastereomer, or salt thereof.

* * * * *

UNITED STATES PATENT AND TRADEMARK OFFICE
CERTIFICATE OF CORRECTION

PATENT NO. : 7,135,467 B2
APPLICATION NO. : 10/755642
DATED : November 14, 2006
INVENTOR(S) : Michael A. Walker et al.

Page 1 of 1

It is certified that error appears in the above-identified patent and that said Letters Patent is hereby corrected as shown below:

On the title page, in the inventor section (75): Narasimhulu B. Naidu should read --B. Narasimhulu Naidu--.

Signed and Sealed this

Sixth Day of March, 2007

JON W. DUDAS
*Director of the United States Patent and Trademark Office*